US011806162B2

(12) United States Patent
Hashkes et al.

(10) Patent No.: US 11,806,162 B2
(45) Date of Patent: Nov. 7, 2023

(54) METHODS AND SYSTEMS FOR THE USE OF 3D HUMAN MOVEMENT DATA

(71) Applicant: Radix Motion Inc., Leander, TX (US)

(72) Inventors: Sarah Hashkes, Seattle, WA (US); Matthew Hoe, Honolulu, HI (US)

( * ) Notice: Subject to any disclaimer, the term of this patent is extended or adjusted under 35 U.S.C. 154(b) by 0 days.

(21) Appl. No.: 18/102,665

(22) Filed: Jan. 27, 2023

(65) Prior Publication Data

US 2023/0172536 A1 Jun. 8, 2023

Related U.S. Application Data

(63) Continuation-in-part of application No. PCT/US2021/043580, filed on Jul. 28, 2021.
(Continued)

(51) Int. Cl.
*A61B 5/00* (2006.01)
*A61B 5/11* (2006.01)
(Continued)

(52) U.S. Cl.
CPC .............. *A61B 5/4848* (2013.01); *A61B 5/11* (2013.01); *G06T 13/20* (2013.01); *G06T 13/40* (2013.01); *G16H 20/10* (2018.01); *G16H 20/70* (2018.01)

(58) Field of Classification Search
CPC ....... G06T 13/00; G06T 13/20; G06T 13/305; G06T 13/40; A61B 5/11; A61B 5/4848; G16H 20/10; G16H 20/70
See application file for complete search history.

(56) References Cited

U.S. PATENT DOCUMENTS 6,611,278 B2 8/2003 Rosenfeld
8,407,756 B2 3/2013 Morris et al.
(Continued)

FOREIGN PATENT DOCUMENTS

CN 111443619 A 7/2020

OTHER PUBLICATIONS

Dolan, David, et al. "The improvisational state of mind: A multidisciplinary study of an improvisatory approach to classical music repertoire performance." Frontiers in psychology 9 (2018): 1341. (Year: 2018).*

(Continued)

*Primary Examiner* — Daniel F Hajnik
(74) *Attorney, Agent, or Firm* — Calyx Law; Graham Pechenik; Chris Byrnes

(57) ABSTRACT

Described herein are methods and systems for using three-dimensional (3D) human movement data as an interactive and synesthetic means of communication that allows body language to be shared between and among individuals and groups, permitting never-before-seen means of expressivity and sharing, and forming the basis for a novel type of media having numerous applications, for example as part of or to enhance the application of psychedelic-assisted therapy, especially where such therapy incorporates augmented or virtual reality. Further described are methods and systems for biomarker-augmented mental health therapies, including psychedelic-assisted and body-image therapies, where such therapies are personalized for a particular user through the creation of personalized sets of diagnostic and therapeutic biomarkers and protocols, customized based on a variety of biometric and other data, including 3D human movement data and a user's mental health history, and in some aspects where such methods and systems promote and protect privacy and consent.

20 Claims, 21 Drawing Sheets

Related U.S. Application Data

(60) Provisional application No. 63/303,622, filed on Jan. 27, 2022, provisional application No. 63/057,873, filed on Jul. 28, 2020.

(51) Int. Cl.
*G16H 20/70* (2018.01)
*G16H 20/10* (2018.01)
*G06T 13/40* (2011.01)
*G06T 13/20* (2011.01)

(56) References Cited

U.S. PATENT DOCUMENTS

| | | | |
|---|---|---|---|
| 9,325,936 | B2 | 4/2016 | Cullen |
| 9,974,478 | B1 | 5/2018 | Brokaw et al. |
| 2008/0170777 | A1* | 7/2008 | Sullivan .......... G06T 7/33 345/475 |
| 2013/0065711 | A1 | 3/2013 | Ueda |
| 2017/0000388 | A1 | 1/2017 | Jessen et al. |
| 2018/0336714 | A1 | 11/2018 | Stoyles et al. |
| 2020/0098166 | A1 | 3/2020 | Ni et al. |
| 2020/0147038 | A1* | 5/2020 | Russ .......... A61K 31/65 |
| 2020/0184701 | A1 | 6/2020 | Chand et al. |

OTHER PUBLICATIONS

Hachaj, Tomasz, et al. "Advanced human motion analysis and visualization: Comparison of mawashi-geri kick of two elite karate athletes." 2017 IEEE Symposium Series on Computational Intelligence (SSCI) IEEE, 2017.
Kurihara, Kazutaka, et al. "Optical motion capture system with pan-tilt camera tracking and real time data processing." Proceedings 2002 IEEE international conference on robotics and automation (Cat. No. 02CH37292). vol. 2. IEEE, 2002.
PCT/US2021/043580, International Preliminary Report on Patentability (Chapter II, PCT), IPEA/US, dated Nov. 14, 2022.
PCT/US2021/043580, Written Opinion of the International Searching Authority (ISA/US), dated Nov. 29, 2021.
PCT/US2021/043580, International Search Report (ISA/US), dated Nov. 29, 2021.
Hashkes, S., How, M., Cohen, I., Korolog, N. (2019) MEU-Communicating Human Movement with Data. SIGGRAPH '19, Virtual, Augmented, and Mixed Reality.
Trewartha, G. (2001). Video-based automatic tracking of three-dimensional human movement (Doctoral dissertation, Loughborough University).
Rushkoff, D. (2019) "Most VR is Total Bullshit: How tech companies turned an instrument of human potential into one of exploitation" https://gen.medium.com/most-vr-is-total-bullshit-81a08431df38.
Pink-Hashkes, S., Selen, L. P. J., & Kwisthout, J. H. P. (2017). One Self, Too Many Tasks: Bimanual Interference from a Predictive Coding Framework.
Miller, M. R., Herrera, F., Jun, H., Landay, J. A., & Bailenson, J. N. (2020). Personal identifiability of user tracking data during observation of 360-degree VR video. Scientific Reports, 10(1), 1-10.
Herrera, F., Bailenson, J., Weisz, E., Ogle, E., & Zaki, J. (2018). Building long-term empathy: A large-scale comparison of traditional and virtual reality perspective-taking. PloS one, 13(10), e0204494.
Hashkes, S., Van Rooij, I., & Kwisthout, J. (2017). Perception is in the details: A predictive coding account of the psychedelic phenomenon. In Proceedings of the 39th Annual Meeting of the Cognitive Science Society (CogSci 2017) (pp. 2907-2912).
Falconer, C. J., Rovira, A., King, J. A., Gilbert, P., Antley, A., Fearon, P., . . . & Brewin, C. R. (2016). Embodying self-compassion within virtual reality and its effects on patients with depression. BJPsych open, 2(1), 74-80.
Spitzer, R. L., Kroenke, K., Williams, J. B., & Löwe, B. (2006). A brief measure for assessing generalized anxiety disorder: the GAD-7. Archives of internal medicine, 166(10), 1092-1097.
Kroenke, K., Spitzer, R. L., & Williams, J. B. (2001). The PHQ-9: validity of a brief depression severity measure. Journal of general internal medicine, 16(9), 606-613.
Mundt, JC, Greist, J. H., Jefferson, J. W., Fedrico, M., Mann, J. J., & Posner, K. (2013). Prediction of suicidal behavior in clinical research by lifetime suicidal ideation and behavior ascertained by the electronic Columbia-Suicide Severity Rating Scale. The Journal of clinical psychiatry, 74(9), 15045.
Sheehan, D. V., Lecrubier, Y., Sheehan, K. H., Amorim, P., Janavs, J., Weiller, E., . . . & Dunbar, G. C. (1998). The Mini-International Neuropsychiatric Interview (MINI): the development and validation of a structured diagnostic psychiatric interview for DSM-IV and ICD-10. Journal of clinical psychiatry, 59(20), 22-33.
Do Rosario, J. L. P., Diógenes, M. S. B., Mattei, R., & Leite, J. R. (2013). Can sadness alter posture ?. Journal of bodywork and movement therapies, 17(3), 328-331.
Kim, Y., Cheon, S. M., Youm, C., Son, M., & Kim, J. W. (2018). Depression and posture in patients with Parkinson's disease. Gait & posture, 61, 81-85.
Alghowine, S., Goecke, R., Wagner, M., Parkerx, G., & Breakspear, M. (Sep. 2013). Head pose and movement analysis as an indicator of depression. In 2013 Humane Association Conference on Affective Computing and Intelligent Interaction (pp. 283-288). IEEE.
Giannakakis, G. et al. (2018), Evaluation of head pose features for stress detection and classification. 2018 IEEE EMBS, 406-409.
Canales J. Z., Fiquer, J. T., Campos, R. N., Soeiro-De-Souza, M. G., & Moreno, R. A. (2017). Investigation of associations between recurrence of major depressive disorder and spinal posture alignment: A quantitative cross-sectional study. Gait & posture, 52, 258-264.
Asadi-Melerdi, S., Rajabi-Shamli E., Sheikhoseini, R., & Piri, H. (2020). Association of upper quarter posture with depression, anxiety, and level of physical activity in sixth grade elementary school students of Karaj city, Iran. International Journal of School Health, 7(1), 48-55.
Stephan, K. E., Binder, E. B., Breakspear, M., Dayan, P., Johnstone, E. C., Meyer-Lindenberg, A., . . . & Friston, K. J. (2016). Charting the landscape of priority problems in psychiatry, part 2: pathogenesis and aetiology. The Lancet Psychiatry, 3(1), 84-90.
Stephan K. E., Bach, D. R., Fletcher, P. C., Flint, J., Frank, M. J., Friston, K. J., . . . Breakspear, M. (2016). Charting the landscape of priority problems in psychiatry, part 1: classification and diagnosis. The Lancet Psychiatry, 3(1), 77-83.
Bedi, G., Carrillo, F., Cecchi, G. A., Slezak, D. F., Sigman, M., Mota, N. B., . . . & Corcoran, C. M. (2015). Automated analysis of free speech predicts psychosis onset in high-risk youths. npj Schizophrenia, 1(1), 1-7.
Tai, S. J., Nielson, E. M., Lennard-Jones, M., Johanna Ajantaival, R. L., Winzer, R., Richards, W. A., Reinholdt, F., Richards, B. D., Gasser, P., & Malievskaia, E. (2021). Development and Evaluation of a Therapist Training Program for Psilocybin Therapy for Treatment-Resistant Depression in Clinical Research. Frontiers in psychiatry, 12, 586682.
Guss, J., Krause, R., & Sloshower, J. (Aug. 13, 2020). The Yale Manual for Psilocybin-Assisted Therapy of Depression (using Acceptance and Commitment Therapy as a Therapeutic Frame).
Mithoefer, M.; Mithoefer, A.; Jerome, L.; Ruse, J.; Doblin, R.; Gibson, E.; Ot'alora M. (2015). A Manual for MDMA-Assisted Psychotherapy in the Treatment of Posttraumatic Stress Disorder. Published by the Multidisciplinary Association for Psychedelic Studies (MAPS).
Johnson, M.; Richards, W.; and Griffiths, R. (2008). Human hallucinogen research: guidelines for safety, J. Psychopharmacol. 22, 603-620.
Olson, D. E. (2021). The promise of psychedelic science. ACS Pharmacology & Translational Science, 4(2), 413-415.
Tullis, P. (2021). The rise of psychedelic psychiatry. Nature, 589(7843), 506-509.
Schenberg E.E. (Jan. 28, 2021). Psychedelic-Assisted Psychotherapy: A Paradigm Shift in Psychiatric Research and Development. Frontiers Pharmacol., 9, 733, 2018; Tullis, P.

(56) References Cited

OTHER PUBLICATIONS

Hosseini, S. A., & Padhy, R. K. (2021). Body image distortion. StatPearls. Treasure Island (FL).

Thrasher et al. (2011). Affective Computing and Intelligent Interaction: 4th International Conference, ACII 2011, Memphis, TN, USA, Oct. 9-12, 2011, Part I 4 (pp. 377-386). Springer Berlin Heidelberg.

Veenstra, L., Schneider, I. K., & Koole, S. L. (2017). Embodied mood regulation: the impact of body posture on mood recovery, negative thoughts, and mood-congruent recall. Cognition and Emotion, 31(7), 1361-1376.

Lewis-Smith, H., Diedrichs, P. C., & Halliwell, E. (2019). Cognitive behavioral roots of body image therapy and prevention. Body Image, 31, 309-320.

Feldman, R., Schreiber S., Pick, C. G., & Been, E. (2020). Gait, balance and posture in major mental illnesses: depression, anxiety and schizophrenia. Austin Medical Sciences, 5(1), 1-6.

Grant & Philips. (2004). Harvard Review of Psychiatry, 12(2): 123-126.

Spreckelsen, P. V., Glashouwer, K. A., Bennik, E. C., Wessel, I., & De Jong, P. J. (2018). Negative body image: Relationships with heightened disgust propensity, disgust sensitivity, and self-directed disgust. PloS one, 13(6), e0198532.

Silva D., Ferriani, L., & Viana, M. C. (2019). Depression, anthropometric parameters, and body image in adults: a systematic review. Revista da Associação Médica Brasileira, 65, 731-738.

Newell, R. J. (1999). Altered body image: a fear-avoidance model of psycho-social difficulties following disfigurement. Journal of Advanced Nursing, 30(5), 1230-1238.

Sadibolova R., Ferre, E. R., Linkenauger, S. A., & Longo, M. R. (2019). Distortions of perceived volume and length of body parts. Cortex, 111, 74-86.

Gaudio, S., et al., (2014). Nonvisual Multisensory Impairment of Body Perception in Anorexia Nervosa: A Systematic Review of Neuropsychological Studies. PloS one, 9(10).

Aday, J., S., et al., (2021). Predicting Reactions to Psychedelic Drugs: A Systematic Review of States and Traits Related to Acute Drug Effects ACS Pharmacology & Translational Science, 4(2), 424.

Carhart-Harris, R., L., et al. (2017). Psychopharmacology Carhart-Harris, R. L., et al. Psilocybin with Psychological Support for Treatment-Resistant Depression: Six-Month Follow-Up. Psychopharmacology, 235, 399-408.

MAPS. MDMA-Assisted Therapy Code of Ethics. MAPS Bulletin Spring 2019: 29(1).

Lindsay, B. "As psychedelic therapy goes mainstream, former patient warns of danger of sexual abuse." CBC/Radio-Canada. Published Mar. 18, 2021. Accessed Jan. 25, 2023.

Liang, Y., Zheng, X., & Zeng, D. D. (2019). A survey on big data-driven digital phenotyping of mental health. Information Fusion, 52, 290-307.

\* cited by examiner

METHODS AND SYSTEMS FOR THE USE OF 3D HUMAN MOVEMENT DATA

CROSS REFERENCE

This is a continuation-in-part application with priority to PCT/US2021/043580, filed Jul. 28, 2021, with priority under PCT Art. 8(1) and Rule 4.10 to U.S. Prov. Appl. No. 63/057,873, filed Jul. 28, 2020; priority is also claimed under § 119(e) to U.S. Prov. Appl. No. 63/303,622, filed Jan. 27, 2022; each of the above are incorporated by reference as if fully set forth herein.

FIELD OF THE INVENTION

Described herein are methods and systems for using three-dimensional (3D) human movement data, for example as an interactive and synesthetic means of communication, and to inform and improve mental health therapies, such as psychedelic-assisted therapy (PAT).

BACKGROUND OF THE INVENTION

Human beings are inherently social animals, for whom communication is both a fundamental feature and a fundamental need. Communication forms the foundation for human interaction, connection, and bonding.

Communication, generally defined, is the act of conveying meaning, through the use of mutually understood signs, symbols, and semiotic rules. While sometimes narrowly understood to refer to verbal and written language specifically, communication also includes non-linguistic modes of meaning transfer, such as eye movements, facial expressions, hand gestures, body postures, and the use of common physical space (taken together, "body language"). Indeed, the word communication comes from the Latin verb "communicare," meaning broadly "to share."

Body language in fact plays an outsize role in human communication. Studies have demonstrated that as much as 55 percent of human communication is based on body language. From the earliest age, humans mimic their parents, learn skills by copying others, and respond behaviorally and emotionally to the body language of others around them, even before they are able to understand and use verbal language.

In multiple areas of the brain responsible for processing movement and touch, humans have "mirror neurons" that fire both when a person acts and when a person observes the same action performed by another. Mirror neurons have been demonstrated to underpin the ability to understand that others have beliefs, desires, intentions, and perspectives that are different from one's own ("theory of mind"), and to contribute to the human capacity for empathy. Empathy, the ability to understand and share someone else's emotions, is an imperative ingredient of individual well-being, and a critical component of successful social interaction. According to the theory of "embodied cognition," it also has been shown that physical experience is an irreducible aspect of human cognition, and that bodily movement and interaction in the context of a task or environment will impact an individual's perceptions, emotions, and behaviors. Given such teachings, it is therefore believed that, in large part, the ability to use and observe body language in communication with others is necessary for individual and social flourishing.

Generally, advances in communication technology have focused only on addressing spatial and temporal limitations. For instance, from the first smoke signals, through the telegraph and telephone, to wireless and satellite technologies, advances have allowed communication with more and more recipients who are distant in space. And from the first cave paintings, through print, radio, and television, to the internet and social media, advances have allowed communication with more and more recipients who are also distant in time.

Despite these advances, human communication technologies remain substantially incomplete. For instance, while such advances permit widespread communication of verbal and written language, no current technologies allow communication of each aspect of body language. Thus, the ability for humans to fully express themselves—and to fully share their thoughts, feelings, emotions, and beliefs—remains unrealized. As increasing numbers of humans retreat behind screens, both at work and at home, there is especially great need for a further advance.

Several attempts to bridge this divide have been made. Video chat applications (e.g., Skype, FaceTime, Zoom) introduced a visual modality to communications that might otherwise have involved only voice or text. Messaging platforms allow sharing of emoticons and emojis as well as "animoji," "bitmoji," "memoji," and the like, that permit some sharing of expressions, emotions, and other non-linguistic information. Social media platforms (e.g., Snapchat, Facebook, Instagram, TikTok) provide the ability to share videos and "stories" that combine visual communication with the expressive aspects of bitmoji and various "filters," i.e., effects that augment facial or bodily movements, overlaid onto a video clip. It also has become common to share visual content and "memes" (e.g., image macros and animated gifs) to communicate emotions and other information that may not be easily conveyed linguistically.

However, none of these attempts solve all of the problems of prior communication technologies. Video chat applications, for example, generally are for synchronous communication, are used in ways that only exchange facial information, and even there have latency and bandwidth issues that make conveying emotional signals with facial expressions less robust and reliable. While facial expressions and some additional body language can be shared asynchronously (and even modified or enhanced) on messaging and social media platforms, these only can be shared as two-dimensional video files that are not interactive. And while some expressive visual information can be shared through "reaction gifs" and other memes, these rely on (and are in fact used because of) a predetermined vocabulary of symbolic meaning, rather than the unique and personal meaning of the sender.

Overcoming many of the limitations in the prior art, the inventors disclose novel communication methods that utilize three-dimensional (3D) human movement data. These novel communication methods permit body language to be shared, deepening human connections through the emotion and empathy that such sharing represents and engenders. Although prior art systems exist to record 3D human movement data, the use of such data is typically for animation (e.g., movies, video games), and its purpose is ultimately to generate two-dimensional (2D) video. 3D movement data has not been used as a medium of communication, as a basis for a social communication platform, or in ways that allow the types of interactivity taught herein.

The inventors also disclose novel methods for synesthetic communication, which permit never-before-seen forms of expressivity and sharing, further intensifying human connections in new ways. While prior art virtual reality (VR)

systems allow users to try on various "avatars," some with different features or capabilities than humans (e.g., wings, tails, tentacles), such technologies never have been used in ways that connect VR systems with technology available on smartphones (e.g., mobile augmented reality (AR)), or that create experiences solely with mobile AR systems, involving communication with 3D human movement data, and multiple forms of interactivity with such data.

These novel methods for synesthetic communication are believed to increase neural prediction error in a way analogous to the increase in prediction error caused by consuming psychedelic substances, increasing the level of surprise in the brain, and resulting in greater neuroplasticity and learning.

The disclosed methods accordingly not only can be used as part of psychedelic experiences (including PAT), and to improve and enhance such psychedelic experiences, but they also can teach individuals about psychedelic experiences without the individual having to consume a psychedelic substance, by demonstrating to an individual (including to a psychedelic naïve individual) multiple aspects of what a psychedelic experience may be like.

Additionally, the inventors disclose multiple novel methods and systems for using the 3D human movement data collected in the described communication methods, in fields such as artificial intelligence (AI), social, gaming, education, fitness, health, entertainment, research, and robotics. Through these methods and systems, inventors disclose how the 3D movement data itself forms a new resource and a new type of media with numerous significant applications.

Further, the inventors disclose methods and systems for mental health therapies, including PAT, such as psychedelic-assisted psychotherapy, as well as body-image therapy (BIT), such as psychotherapy or cognitive behavioral therapy for eating disorders such as anorexia, through the analysis and integration of a patient's biometric and movement data ("biomarkers"), including but not limited to pose, sway, balance, rhythm, body asymmetries, smoothness, jerkiness, body motion towards or away from a cue, kinetic energy of body parts, reaction time, and/or total amount of body movement, which can be used to inform therapeutic treatment, and thereby enhance individual patient outcomes in such treatment and the overall efficacy of such therapies.

Mental health is the leading cause of disability worldwide and, as of 2019, has a societal cost of approximately $2.5 trillion in the U.S. alone (see, e.g., Liang et al., Inf. Fusion, 52, 290-307, 2019). Mental health therapy is a relatively new field, emerging out of the mental hygiene movement initiated in 1908 by consumers of psychiatric services and professionals interested in improving the conditions and the quality of treatment of people with mental disorders (see, e.g., Bertolote, World Psychiatry, 7(2): 113-116, 2008). In 1908, Clifford Beers published *A Mind That Found Itself*, a book based on Beers's personal experience of admissions to three mental hospitals. The term "mental hygiene" had been suggested to Beers by Adolf Meyer and the book led to the creation in 1909 of the National Commission of Mental Hygiene. The Commission quickly grew, internationalizing its activities, and between 1919 and 1924 had led to the establishment of national associations concerned with mental hygiene in France, South Africa, Italy, and Hungary. These national associations ultimately led to the formation of the International Committee on Mental Hygiene, which was later superseded by the World Federation for Mental Health (WFMH), founded in 1948.

Around the same time that the WFMH was founded, psychedelic substances were attracting new interest and research among psychiatrists. A psychedelic substance is loosely defined as a substance which produces certain "psychedelic" effects at particular dosages, e.g., vivid visual and auditory perceptual changes, often accompanied by intense emotional, mystical, or "spiritual" experiences. The term "psychedelic" was coined in 1953 by the psychiatrist Humphrey Osmond, during written correspondence with author Aldous Huxley. Psychedelic derives from two Ancient Greek words, psyche meaning "mind" or "soul," and delos meaning "reveal" or "manifest," with the two together thus meaning "mind manifesting."

Traditionally, "psychedelics" are understood as chemical compounds that are agonists of serotonin 2A ($5-HT_{2A}$) receptors, including tryptamines (e.g., N,N-dimethyltryptamine (DMT), found in the traditional brew "ayahuasca," and psilocybin and psilocin found in "magic" mushrooms), phenethylamines (e.g., mescaline, from the peyote and San Pedro cacti), and lysergamides (most notably lysergic acid diethylamide (LSD)); however, substances besides these "classic psychedelics," such as 5-MeO-DMT, 3,4-methylenedioxymethamphetamine (MDMA), 2C-B and other "2C-x" compounds, ibogaine, ketamine, salvinorin A, nitrous oxide, and numerous others, which have hallucinogenic, "entheogenic," "entactogenic" or "empathogenic," dissociative, and other effects, and which are also used in "psychedelic"-assisted therapy, will be appreciated to be "psychedelics" in the context herein, as will single enantiomers and enantiomeric mixtures; salts and solid forms such as polymorphs, hydrates, solvates, and co-crystals; deuterated and halogenated versions; and prodrugs, metabolites, analogs, and derivatives of any of the above, including combinations thereof, and further including novel chemical compounds or NCEs having similar structures, effects, and/or uses.

Increasingly, psychedelics are being accepted and utilized as effective tools in the diagnosis and treatment of a wide variety of mental health conditions. See, e.g., Tullis, Nature, v. 598, 506-509, 2021; Olson, ACS Pharmacol. Transl. Sci, v. 4, issue 2, 413-45, 2021 (from an entire issue of *ACS Pharmacology & Translational Science* directed to psychedelic research).

Although optimism exists across the field, clinical research studies on PAT up to this point are few and have been done on relatively small populations, meaning there are still questions concerning scalability, applicability amongst patient groups of different backgrounds, the potential for adverse events, and different patient-specific needs, such as optimal dosage based on age, weight, physical condition, emotional condition, etc. (see, e.g., Aday et al., ACS Pharmacol. Transl. Sci., v. 4, issue 2, 2021 at 424).

Furthermore, because of the lack of rigorous scientifically-based standardization, clinical trials involving PAT usually have overly-conservative protocols, for example safety tolerances and margins which far exceed standards for other medical therapies, requiring many more resources than conventional medical therapies. However, the lack of scientifically-based standardization means there is no universally recognized list of factors/markers for whether a subject would be more or less likely to have a good outcome.

Further still, the screening interviews and preparation sessions for PAT require the collection and documentation of data concerning the psychological state/mood of the patient, but the process is relatively subjective, and often different assessment scales are used (e.g., Hamilton Rating Scale for Depression (HAM-D); the Mini International Neuropsychiatric Interview 5 (MINI 5) (see, e.g., Sheehan et al., J. Clinical Psych, 59 Supple. 20: 22-33, 1998); the Columbia Suicide Severity Rating Scale (C-SSRS) (see, e.g., Mundt, J C et al., J. of Clinical Psychiatry, 74(9): 887-93, 2013); the Patient Health Questionnaire (PHQ-9) (see, e.g., Kroenke et al., J. Gen. Intern. Med., v. 16(9), 2001); the Generalized Anxiety Disorder 7 (GAD-7) (see, e.g., Spitzer et al., Arch. Intern. Med., 166(10): 1092-97, 2006); etc.), once again making it difficult to aggregate or compare data.

Body image distortion and body dissatisfaction are common in both clinical and nonclinical populations (see, e.g., Hosseini et al., StatPearls, 2021). Body image is the subjective picture of individuals of their own body, irrespective of how their body actually looks. As a complex construct comprising thoughts, feelings, emotions, and behaviors, body-image distortion is a core component of several serious diseases, including body dysmorphic disorder, anorexia nervosa, and bulimia nervosa (see, e.g., Gaudio et al., PLoS One, 9(10), 2014; Sadibolova et al., Cortex, 111: 74-86, 2019). Body-image disorders can have drastic effects on physical and psychological health and can influence self-esteem, mood, competence, social functioning, and occupational functioning.

Beginning in the early 1900s, neurologists have made considerable efforts to understand atypical forms of body perception reported by patients with brain injuries and phantom limb experiences reported by amputees. Such efforts have been largely rooted in neuropathology, though more recent neurologists have theorized body image as dynamic, changing with age, mood, or even clothing (Newell, J. Adv. Nurs., 30: 1230-1238, 1999), while others define body image as the representation of identity derived from both external and internal body experiences (Krueger, Brunner/Mazel, 1989). Today, a variety of different but related terms are often used interchangeably in the literature to describe altered body image perceptions, including body-image distortion, body-image misperception, body-image disturbance, negative body image, altered body image, and body dissatisfaction. Generally speaking, negative body image typically entails a dissatisfaction with one's body or body parts, a preoccupation with appearance, and engagement in behaviors such a frequent mirror checking, self-weighing, avoidance of public situations, and generally perceived discrepancies between the perception of one's body image and an idealized image (see, e.g., Silva et al., Rev. Assoc. Med. Bras., 65(5): 731-738, 2019; Spreckelsen et al., PLoS One, 13(6), 2018).

Body-image therapy has evolved significantly over the past two decades through the pioneering work of Thomas Cash and his cognitive-behavioral approach to addressing body image (see, e.g., Lewis-Smith et al., Body Image, 31: 309-320, 2019). Cash conceptualized a theoretical cognitive-behavioral model of body image, comprising "body image evaluation" and "body image investment," which distinguishes an individual's beliefs and appraisals regarding their body from the cognitive, behavioral, and emotional importance of an individual's body in relation to their sense of self-worth. Following Cash's work, cognitive behavioral therapy (CBT) has become one of the most researched and empirically supported interventions to address body image concerns. CBT aims to modify irrational and dysfunctional thoughts, emotions, and behaviors through self-monitoring, self-assessment, cognitive restructuring, psychoeducation, desensitization, and exposure and response prevention.

Although body-image therapy, and especially that done through CBT, has been widely supported by mental health professionals, comprehensive evaluations of leading therapeutic interventions (such as Cash's CBT program) have not been widely done. Numerous studies have suffered from high attrition rates and randomized controlled trials evaluating body image disorders and the efficacy of body-image therapy have struggled to achieve sample sizes that can support statistically significant conclusions for therapeutic efficacy. Given the complexity of body image disorders and myriad psychological and socially/culturally interdependent factors that can generate such disorders, it has been historically difficult to isolate therapeutic treatment that can be individually tailored to the unique needs of any given patient.

Furthermore, individuals with body image disorders often have multiple forms of disorders that appear to be comorbid with one another (e.g., body dysmorphic disorder (BDD) being correlated with both eating disorders and obsessive-compulsive disorder (see, e.g., Grant & Phillips, Harvard Review of Psychiatry, 12(2): 123-126, 2004)), but the relationship between these disorders is largely unstudied. Where studies have been attempted, they are often built around simple, qualitative comparisons between similarities of the disorders and are relegated to the self-reported symptoms of patients.

The lack of objective, standardized criteria for studying individuals suffering from body image disorders, as well as other mental health disorders and conditions, means there are no scientifically-agreed-upon measurements that can be made to guide therapeutic interventions or to indicate likelihood of success for any given patient. Additionally, the lack of objective, standardized criteria for case studies means that cross-study analysis is relatively futile in deducing new and more efficient means of therapeutic intervention.

Overcoming the many limitations in the art and solving these and other problems, the inventors herein additionally describe novel ways of integrating biometric and movement data, including 3D movement data, into mental health therapies like PAT and BIT, which will thereby inform more effective patient treatment, and result in improved patient outcomes.

INCORPORATION BY REFERENCE

Each patent, publication, and non-patent literature cited herein is hereby incorporated by reference in its entirety as if each was incorporated by reference individually. However, where such reference is made, and whether to patents, publications, non-patent literature, or other sources of information, it is for the general purpose of providing context for discussing features of the invention. Accordingly, unless specifically stated otherwise, reference is not to be construed as an admission that the document or underlying information, in any jurisdiction, is prior art, or forms part of the common general knowledge in the art.

BRIEF SUMMARY OF THE INVENTION

The following presents a simplified summary of some embodiments of the invention in order to provide a basic understanding of the invention. This summary is not an extensive overview of the invention. It is not intended to identify key or critical elements of the invention or to delineate the scope of the invention. Its sole purpose is to present some embodiments of the invention in a simplified form as a prelude to the more detailed description that is presented later.

In a first aspect, provided is a method for psychedelic-assisted therapy (PAT) using 3D human movement data, the method comprising the steps of: (a) capturing a first 3D human movement input from a patient during a preparation session for PAT; (b) creating a first 3D movement data package from the first 3D human movement input; (c) saving a first 3D movement data file to permanent storage, comprising the first 3D movement data package; (d) capturing a second 3D human movement input from a patient during a psychedelic dosing session; (e) creating a second 3D movement data package from the second 3D human movement input; (f) saving a second 3D movement data file to permanent storage, comprising the second 3D movement data package; and (g) comparing the first 3D movement data file and the second 3D movement data file during an integration session.

In another aspect, provided is a method for psychedelic-assisted therapy (PAT) using 3D human movement data, the method comprising the steps of: (a) capturing a first 3D human movement input from a patient during a first PAT session, which may include any of a preparation, dosing, or integration session; (b) creating a first 3D movement data package from the first 3D human movement input; (c) saving a first 3D movement data file to permanent storage, comprising the first 3D movement data package; (d) capturing a second 3D human movement input from a patient during a during a second PAT session, which may include any of a preparation, dosing, or integration session; (e) creating a second 3D movement data package from the second 3D human movement input; (f) saving a second 3D movement data file to permanent storage, comprising the second 3D movement data package; and (g) comparing the first 3D movement data file and the second 3D movement data file during a third PAT session, which may include any of a preparation, dosing, or integration session.

In some embodiments, the permanent storage contains a searchable movement database indexed based on the metadata of 3D movement files. In some embodiments, the searchable movement database contains metadata based on protocols developed for the standardization of procedures used with PAT. In some embodiments, the method further comprises determining characteristic movement markers associated with a positive or negative patient experience in the first or second 3D movement data file (in other embodiments, characteristic movement markers associated with a positive or negative patient experience may be determined in the first or second 3D human movement input or the first or second 3D movement data package).

In some embodiments, the characteristic movement markers are associated with a positive patient experience. In some embodiments, the characteristic movement markers are used to predict or promote a positive patient experience. In some embodiments, the characteristic movement markers are associated with a negative patient experience. In some embodiments, the characteristic movement markers are used to predict or prevent a negative patient experience.

In some embodiments, comparing the first 3D movement data file and the second 3D movement data file is used to predict or promote a positive patient experience, to predict or prevent a negative patient experience, or to evaluate the efficacy of the therapy.

In another aspect, provided is a method for PAT using 3D human movement data, the method comprising the steps of: (a) capturing a first 3D human movement input from a therapist during a preparation session for PAT; (b) creating a first 3D movement data package from the first 3D human movement input; (c) saving a first 3D movement data file to permanent storage, comprising the first 3D movement data package; (d) capturing a second 3D human movement input from a patient during a psychedelic dosing session; (e) creating a second 3D movement data package from the second 3D human movement input; (f) sending the second 3D movement data package to a first recipient device; (g) rendering a 3D movement object on the first recipient device, from the second 3D movement data package; (h) sending the first 3D movement data package to a second recipient device; and (i) rendering a 3D movement object on the second recipient device, from the first 3D movement data package.

In another aspect, provided is a method for PAT using 3D human movement data, the method comprising the steps of: (a) capturing a first 3D human movement input from a therapist during a first PAT session, which may include any of a preparation, dosing, or integration session; (b) creating a first 3D movement data package from the first 3D human movement input; (c) saving a first 3D movement data file to permanent storage, comprising the first 3D movement data package; (d) capturing a second 3D human movement input from a patient during a second PAT session, which may include any of a preparation, dosing, or integration session; (e) creating a second 3D movement data package from the second 3D human movement input; (f) sending the second 3D movement data package to a first recipient device; (g) rendering a 3D movement object on the first recipient device, from the second 3D movement data package; (h) sending the first 3D movement data package to a second recipient device; and (i) rendering a 3D movement object on the second recipient device, from the first 3D movement data package.

In some embodiments, the methods further comprise the step of saving a second 3D movement data file to permanent storage, comprising the second 3D movement data package. In some embodiments, the permanent storage contains a searchable movement database indexed based on the metadata of 3D movement files. In some embodiments, the second 3D movement data package created from the second 3D human movement input contains additional input from one or more additional input means.

In some embodiments, the disclosed methods further comprise determining characteristic movement markers associated with a positive or negative patient experience from the second 3D human movement input or the second 3D movement data package.

In some embodiments, the characteristic movement markers are associated with a positive patient experience. In some embodiments, the characteristic movement markers are used to predict or promote a positive patient experience. In some embodiments, the characteristic movement markers are associated with a negative patient experience. In some embodiments, the characteristic movement markers are used to predict or prevent a negative patient experience.

In some embodiments, the disclosed methods further comprise evaluating the efficacy of the therapy by comparing the first 3D movement data package and the second 3D movement data package. In some embodiments, evaluating the efficacy comprises comparing characteristic movement markers of the therapist in the first 3D movement data package and characteristic movement markers of the patient in the second 3D movement data package.

In a further aspect, provided is a method for PAT using 3D movement data, the method comprising the steps of: (a) capturing a first 3D human movement input from a patient during PAT; (b) creating a first 3D movement data package from the first 3D human movement input; and (c) determining characteristic movement markers associated with a positive or negative patient experience; wherein the characteristic movement markers can be used to inform the PAT.

In some embodiments, the characteristic movement markers are associated with a positive patient experience. In some such embodiments, the method further comprises utilizing the characteristic movement markers to predict or promote a positive patient experience. In some embodiments, the characteristic movement markers are associated with a negative patient experience. In some such embodiments, the method further comprises utilizing the characteristic movement markers to predict or prevent a negative patient experience.

In some embodiments, the first 3D human movement input is captured during a PAT session, which may include any of a preparation, dosing, or integration session. In some embodiments, the first 3D human movement input is captured during a preparation session for PAT. In other embodiments, the first 3D human movement input is captured during a psychedelic dosing (drug administration) session. In other embodiments, the first 3D human movement input is captured during an integration session for PAT.

In some embodiments, the method further comprises capturing a second 3D human movement input from a patient, and creating a second 3D movement data package from the second 3D human movement input. In some embodiments, the second 3D human movement input is captured during a PAT session, which may include any of a preparation, dosing, or integration session. In some embodiments, the second 3D human movement input is captured during a psychedelic dosing session. In other embodiments, the second 3D human movement input is captured before a psychedelic dosing session. In other embodiments, the second 3D human movement input is captured after a psychedelic dosing session.

In some embodiments, the method further comprises evaluating the efficacy of the therapy by comparing the first 3D movement data package and the second 3D movement data package. In some such embodiments, evaluating the efficacy comprises comparing the characteristic movement markers in the first 3D movement data package and the characteristic movement markers in the second 3D movement data package.

In some aspects are disclosed non-transitory computer-readable storage media storing executable instructions that, when executed by a processor, cause the processor to perform steps comprising the disclosed methods, as well as systems for performing the steps of such methods.

The foregoing has outlined broadly and in summary certain pertinent features of the disclosure so that the detailed description of the invention that follows may be better understood, and so that the present contribution to the art can be more fully appreciated. Hence, this summary is to be considered as a brief and general synopsis of only some of the objects and embodiments disclosed herein, is provided solely for the benefit and convenience of the reader, and is not intended to limit in any manner the scope, or range of equivalents, to which the claims are lawfully entitled. Additional features of the invention are described hereinafter. It should be appreciated by those in the art that all disclosed specific compositions and methods are only exemplary, and may be readily utilized as a basis for modifying or designing other compositions and methods for carrying out the same purposes. Such equivalent compositions and methods will be appreciated to be also within the scope and spirit of the invention as set forth in the claims.

BRIEF SUMMARY OF THE DRAWINGS

To further clarify various aspects of some embodiments of the invention, a more particular description of the invention will be rendered by reference to the embodiments which are illustrated in the included figures. It will be understood and appreciated that the figures depict only certain exemplary implementations of the invention and are not to be considered limiting of its scope. As the figures are generally illustrated diagrammatically, or otherwise representationally, they are simply provided to help illuminate various concepts of the invention. Additional aspects of the invention are further elucidated and explained with greater specificity, but still by way of example only, in the detailed description, which shall be read with reference to the accompanying figures in which.

DETAILED DESCRIPTION OF THE INVENTION

Figure 1:
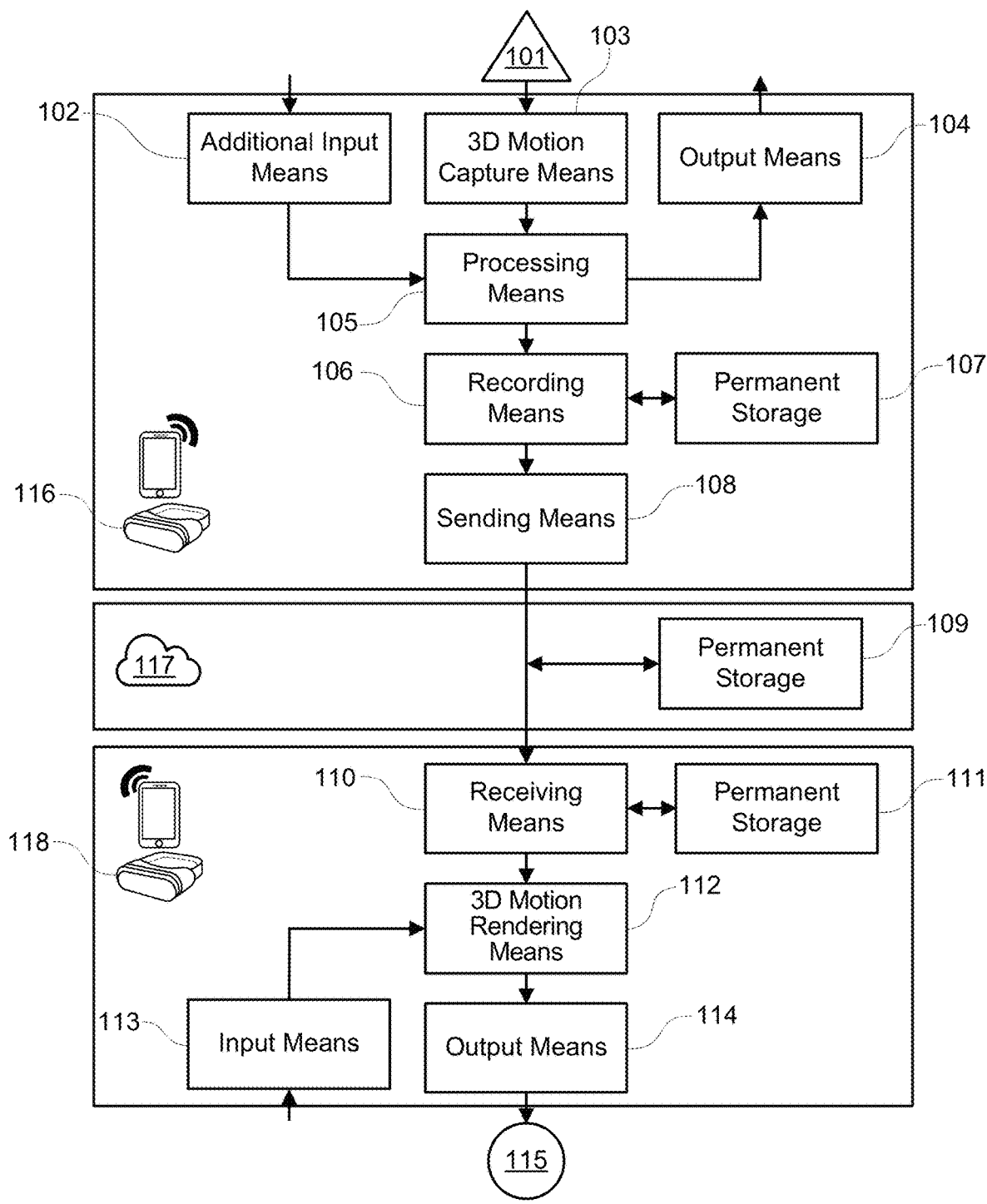
FIG. 1 is a block diagram illustrating an exemplary system architecture in which embodiments of the invention may be implemented, and illustrating an exemplary flow from a sender to a recipient, according to an implementation. Where modules or steps are connected with arrows using dashed lines, they shall be considered optional to the exemplary implementation of the illustrated embodiment.

While the present invention is now further described in terms of particular embodiments, examples, and applications, and by reference to the exemplary embodiments that are depicted in the accompanying figures, this description it is not intended to in any way limit its scope to any such embodiments, examples, and applications, and it will be understood that many modifications, substitutions, alternatives, changes, and variations in the described embodiments, examples, applications, and other details of the invention illustrated herein can be made by those skilled in the art without departing from the spirit of the invention, or the scope of the invention as described in the appended claims, including all equivalents to which they are lawfully entitled.

Various modifications, as well as a variety of uses in different applications, will be readily apparent to those skilled in the art, and the general principles defined herein may be applied to a wide range of aspects. Thus, the invention is not intended to be limited to the aspects presented, but is to be accorded the widest scope consistent with the principles and novel features disclosed herein. This description is designed to make such embodiments apparent to one of ordinary skill, in that they will be both readily cognizable and readily creatable without undue experimentation.

When introducing elements of the invention or the embodiments thereof, the articles "a," "an," "the," and "said" are intended to mean that there are one or more of the elements. Any reference to an element in the singular is therefore not intended to mean "one and only one" unless specifically so stated, but rather "one or more"; therefore, the term "or" standing alone, unless context demands otherwise, shall mean the same as "and/or." The terms "comprising," "including," "such as," and "having" are also intended to be inclusive and not exclusive (i.e., there may be other elements in addition to the recited elements). Thus, for example, the terms "including," "may include," and "include," as used herein mean, and are used interchangeably with, the phrase "including but not limited to." The word "exemplary" is used herein to mean "serving as an example, instance, or illustration." Any aspect, embodiment, process, or implementation described herein as "exemplary" is therefore not to be construed as necessarily preferred or advantageous over others.

It will be appreciated that headings herein are being utilized only to expedite review of this document by a reader. They should not be construed as limiting the invention in any manner.

Among these various aspects and embodiments of the invention are methods and systems for communication using 3D human movement data, and for using 3D human movement data as part of the disclosed biomarker-augmented mental health therapies, including PAT and BIT. Such methods and systems may be better understood by reference to the following examples.

Example 1: Communication of 3D Movement Data from a Sender to a Recipient

Through this Example, it will be evident how in aspects of the invention, a sender can communicate with a recipient by sending the recipient 3D human movement data generated by the sender. Compared to prior technologies that have allowed a sender to communicate various other messages—e.g., text, voice, images, 2D video—embodiments of the invention allow, for the first time, a sender to communicate a message that consists of 3D human movement data.

For example, a sender can share a hug, blow a kiss, or show off a dance move. A parent can also share their child's dance move, and thus it will be readily appreciated that for this Example, and in the other embodiments described and claimed, a "sender" is the human from whose movements the 3D movement data is generated. The sender, in other words, is the human who provides the 3D human movement input. The sender however need not also be the person operating the device to capture or transmit the 3D movement data.

Because an improvement of the invention is the ability to communicate using 3D human movement data, it will be understood that the sender is human. For convenience, the terms "3D movement data" and "3D human movement data" are thus used interchangeably herein. Elsewhere, the word "human" also may be left out for convenience, without changing the meaning of a term. "3D movement data" includes data representing any form of human body language, such as eye movements, facial expressions, hand gestures, body postures, and the use of physical space. In some disclosed embodiments, "3D movement data" means non-facial data.

It will be readily appreciated that "3D movement data" and "3D human movement data" also need not in all embodiments be the movement data of a "whole" human, but in some embodiments may be data captured from part of a human, such as a human torso, a human down to (and either including or not) the knee joints, a human down to (and either including or not) the ankle joints, a human all but the feet, and so forth, as will be easily understood. In some embodiments, facial expressions and/or other facial data is captured. In other embodiments, including in certain preferred embodiments, facial expressions and/or other facial data is not captured. In some embodiments, facial expressions and/or other facial data is not captured because the embodiment is intended to capture only or otherwise captures only certain human body movement data (e.g., body language, body posture, body movements, body gestures, body modifications, movement input, body-tracking, physiological or physiometric data based on the human body, and other movement data relating to the body or parts of the body moving in or through three-dimensional space), or is intended to capture only non-facial movement data. In some embodiments, facial expressions and/or other facial data is not captured in order or in part to promote privacy. In some embodiments, as would be understood by those of ordinary skill, only 3D non-facial movement input, 3D non-facial movement data (including as a data package, data message, data file, or data package), and/or 3D non-facial movement objects will therefore be captured, created, sent, received, rendered, saved, compared, or like actions described herein.

Critically, the 3D movement data is not simply a 2D video capture of a 3D movement or series of movements; nor is it a 2D video conversion of 3D movement data that was captured. Instead, it is comprised of 3D movement data itself, as the following description will make clear.

FIG. 1 is a block diagram illustrating an exemplary system architecture in which embodiments of the invention may be implemented, and further illustrating an exemplary flow from a sender to a recipient, according to this Example. Where modules or steps are connected with patterned arrows illustrated using dashed lines, they shall be considered optional; however, even where modules or steps are connected using solid arrows, they also may be considered optional, depending on the particular embodiment claimed, as will be readily appreciated by the fact that all figures are merely exemplary and not limiting.

In some embodiments taught by FIG. 1, a sender 101 desires to send a 3D movement data message to a recipient 115. In other embodiments, a sender 101 may send a 3D movement data message to multiple recipients; however, for sake of simplicity, reference generally shall be made to a single recipient, although it will be readily appreciated that an embodiment can be adapted to allow messages to be sent to multiple recipients, by reference to the teachings herein combined with the ordinary skill of the art.

It also will be appreciated that, besides teaching the communication of 3D movement data messages between a sender and a recipient, or between a sender and multiple recipients, among the improvements of the invention is its novel disclosure of a social platform based on 3D movement data, wherein many senders and recipients may share 3D movement data and interact with each other's data. The invention further discloses the use of 3D movement data as a part of interactive asynchronous multiplayer movement games.

In preferred embodiments, 3D movement data is combined with or accompanied by computer-generated or sender-defined metadata or additional sender-defined data (such as an accompanying text message). Examples of computer-generated metadata include a unique message identifier, a sender identifier, a recipient identifier, and a time stamp.

In some embodiments, a sender may record a 3D movement data message only to be displayed to a recipient when specific criteria are met, e.g., not until and unless the recipient device is in a particular location (e.g., based on GPS coordinates, based on proximity to another device, within range of a specific Wi-Fi signal, and the like), or on a particular date and/or a particular time, which may be a specific pre-set date and/or time (e.g., 9:01 pm PDT on Jul. 28, 2021), or a time defined by one or more sender- and/or receiver-defined parameters being satisfied (e.g., upon incarceration, incapacitation, disappearance, or death).

In some exemplary implementations, examples of sender-defined metadata may include information about: (1) the avatar, e.g., "skinOn" (is avatar on), "skinHueStart" (base color of avatar), "skinHueSize" (amount of variance in base color), "skinNoiseForce" (noise function of skin); (2) the particles, e.g., "particlesOn" (are particles on), "particlesDecaySpeed" (speed of particle decay), "particlesHueStart" (baseline color of particle), "particlesHueSize" (amount of variance from base color); (3) the filter chosen by the sender, e.g., "explosive" (filter based on movement data kinetic energy), "peaceful" (movement filter based on openness of body posture), and interactive auditory filters; (4) the prosocial game chosen by the sender, e.g., "hearts" (where a sender can blow 3D kisses and a recipient can catch them with a counter showing how many kisses were caught) or "follow" (where a recipient receives points for how well a sender's movements are followed); and (5) other parameters, e.g., "remix" (should data be remixed with other data). The types of other parameters that may be considered for adoption are only limited by the imagination of the ordinary artisan.

Together, the 3D movement data of the sender, along with its metadata and any additional data, form a "3D movement data package." A 3D movement data package may reside on volatile or non-transitory computer-readable media, but when transmitted, is also referred to as a "3D movement data message." A 3D movement data message therefore comprises a 3D movement data package, optionally including any metadata necessary for the file transfer format, and optionally compressed or otherwise modified as appropriate to accomplish the transfer. A "3D movement data message" as used herein thus also means a message transmitted from sender to recipient, comprising the 3D movement data of the sender.

In the embodiments now described, it shall be assumed that sender 101 misses the recipient 115 and, rather than sending a text message saying "I miss you" or sending a heart emoji via text message, desires to express her feelings by sending a unique 3D movement data message representing her own 3D movement of blowing a kiss. In these embodiments, the desire of sender 101 can be instantiated through the use of a sender device 116 and a receiver device 118, both having such functionality as set forth in FIG. 1 and now described. (Or, in embodiments where messages are sent to multiple recipients, to multiple receiver devices 118.)

In these embodiments, sender device 116 will have a 3D motion capture means 103, processing means 105, recording means 106, and sending means 108. Optionally, sender device 116 may have additional input means 102, output means 104, and permanent storage 107.

In these embodiments, receiver device 118 will have a receiving means 110, a 3D motion rendering means 112, and an output means 114. Optionally, receiver device 118 may have permanent storage 111 and input means 113.

Additionally, an optional permanent storage 109 may be utilized, that is physically separate from permanent storage 107 of sender device 116 and permanent storage 111 of receiver device 118, such as a cloud storage device on cloud 117 or another suitable remote storage device. Although each permanent storage will be understood to be physically separate in the embodiments of FIG. 1, each permanent storage may be operationally or functionally coupled so as to communicate with each other and transfer data. A "3D movement data file" comprises a "3D movement data package" when on permanent storage (i.e., is a 3D movement data package, optionally together with the metadata specific to the file format, such as the file header, and optionally compressed or otherwise modified as appropriate for storage).

In some embodiments, sender device 116 and receiver device 118 may be a portable device such as an Apple iPhone running iOS, a handset running Android, or any other suitable smartphone, tablet, or personal computing device. In other embodiments, 116 or 118 may be a VR device or system. At the time of filing, such devices and systems include the Oculus Quest VR, the Oculus Rift S, the Sony PlayStation® VR, the HTC Vive Cosmos, the Valve Index, Windows Mixed Reality headsets, and others. In yet other embodiments, 116 or 118 may be desktop systems or console systems.

It will be readily appreciated that the methods of the invention are not directed towards, or limited by, any particular hardware. Although system and design requirements may vary, it will be understood that software embodying the invention can be implemented on different hardware without reliance on teachings outside of this disclosure or outside of the general knowledge of one of skill in the art.

In some embodiments, sender 101 uses as sender device 116 an Apple smartphone or tablet capable of mobile AR, for instance, an iOS device with an A12 chip. In these embodiments, sender 101 provides 3D human movement input which is captured by the 3D motion capture means 103. Suitable 3D motion capture means include the body-tracking functionality in the ARKit framework on device 116, which recognizes and tracks a person's movements using an iOS device's rear camera.

In the Examples and embodiments described herein, reference may be made to FIGS. 6A-6F, which show representations of screenshots from an iOS device of sender 611 providing the 3D human movement input of blowing a kiss, which kiss additionally takes 3D virtual form as heart 612.

Figure 6A:
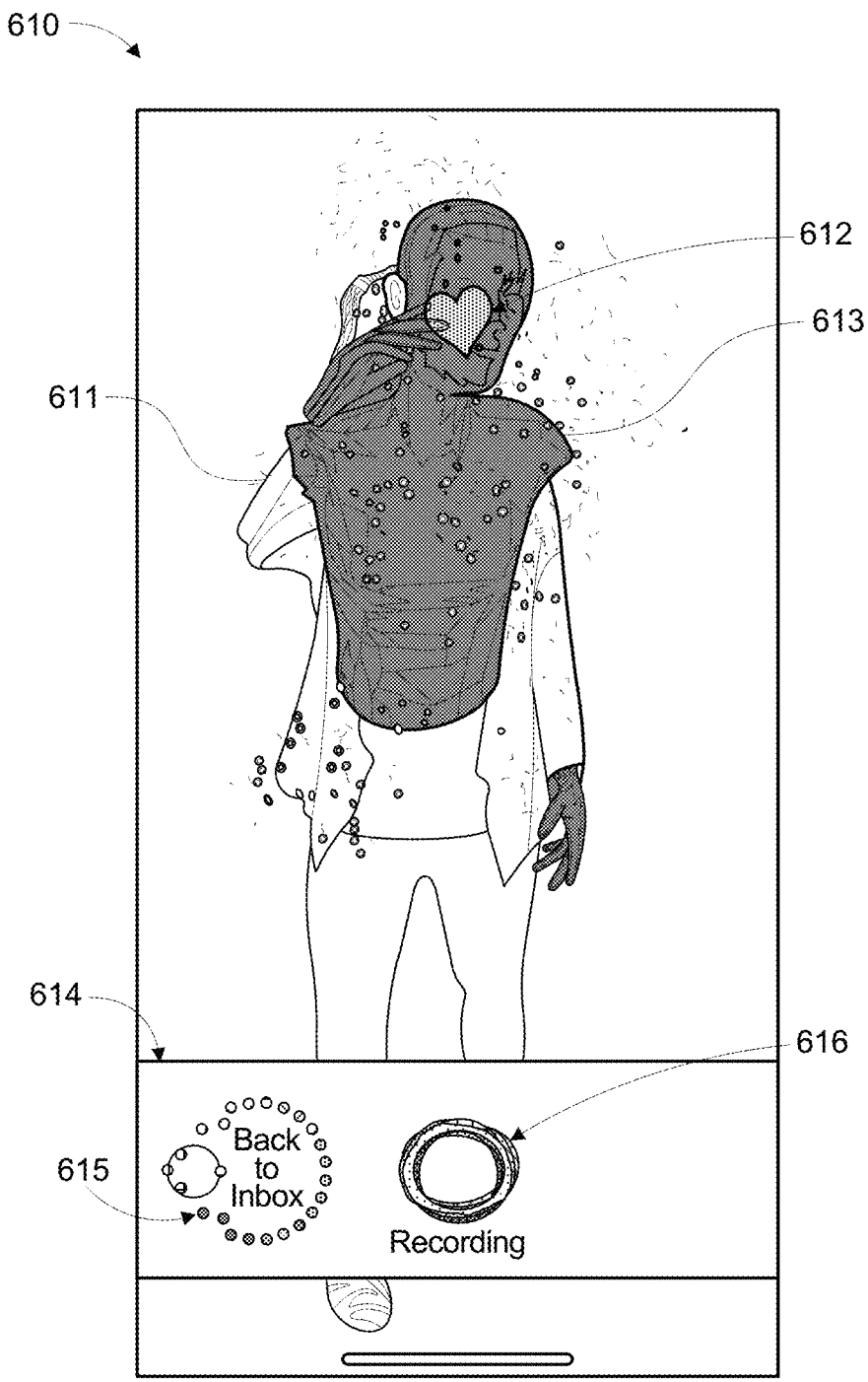
FIG. 6A is a representation of a screenshot from an exemplary implementation of the invention using mobile AR on an iPhone, illustrating the screen of a sender device, and illustrating a timepoint in the capture of 3D human movement data of sender comprising blowing a kiss, further illustrating a visual overlay of a graphical representation of the kiss being blown.
Figure 6B:
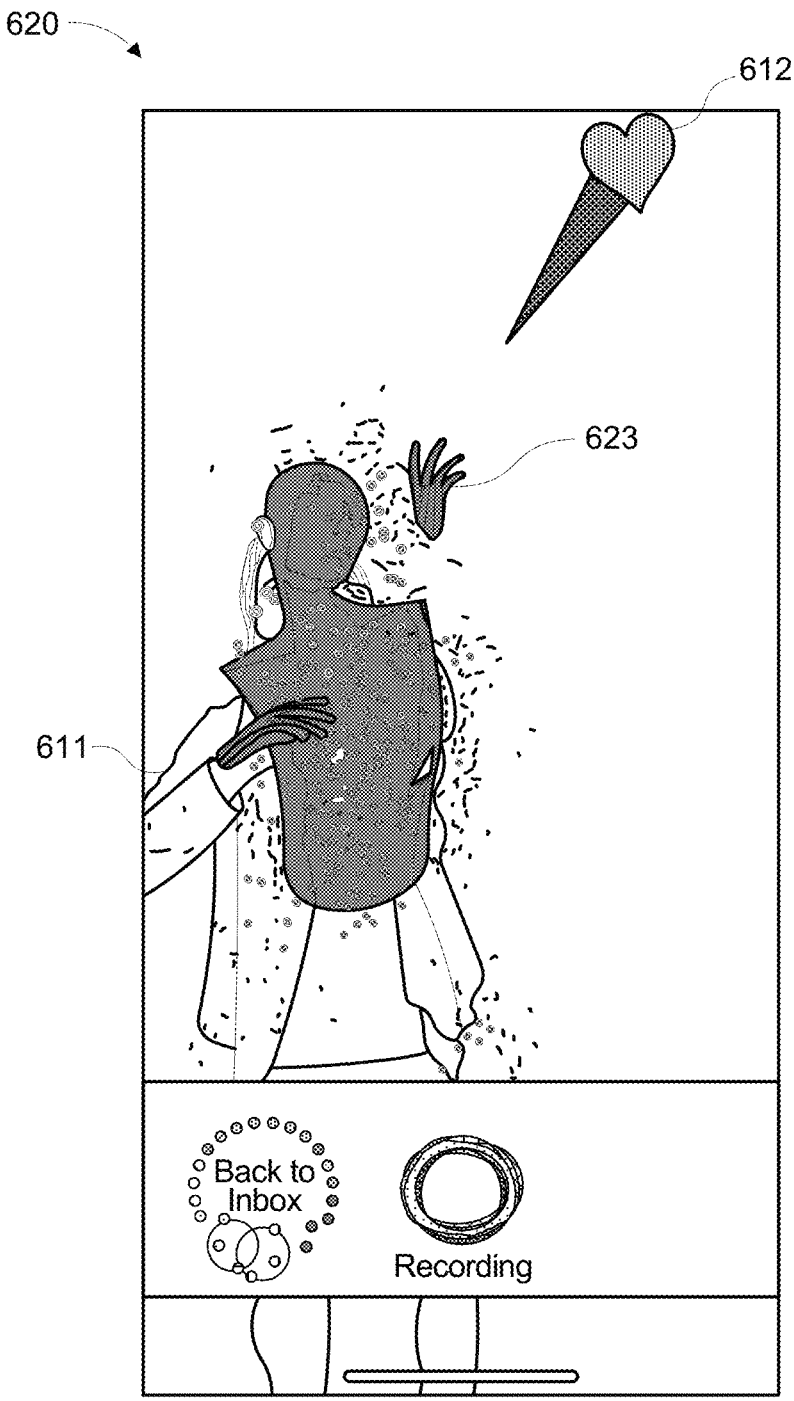
FIG. 6B is a representation of a screenshot from an exemplary implementation of the invention using mobile AR on an iPhone illustrating the screen of a sender device and illustrating a later timepoint in the capture of 3D human movement data of sender comprising blowing a kiss, further illustrating a visual overlay of a graphical representation of the kiss being blown.
Figure 6C:
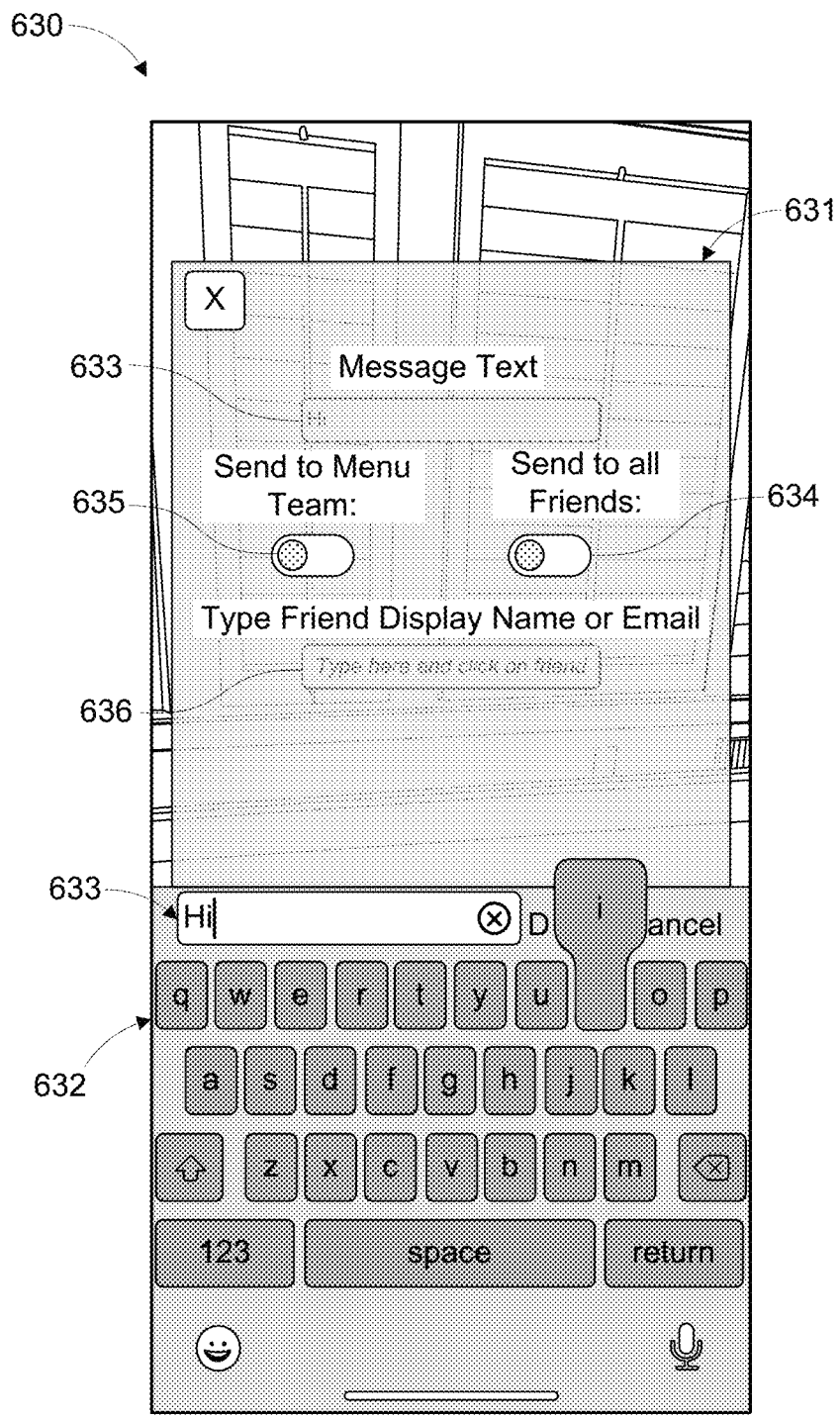
FIG. 6C is a representation of a screenshot from an exemplary implementation of the invention using mobile AR on an iPhone, illustrating the screen of a sender device, the screen being used to send the captured 3D human movement data to one or more recipients, optionally including message text.
Figure 6D:
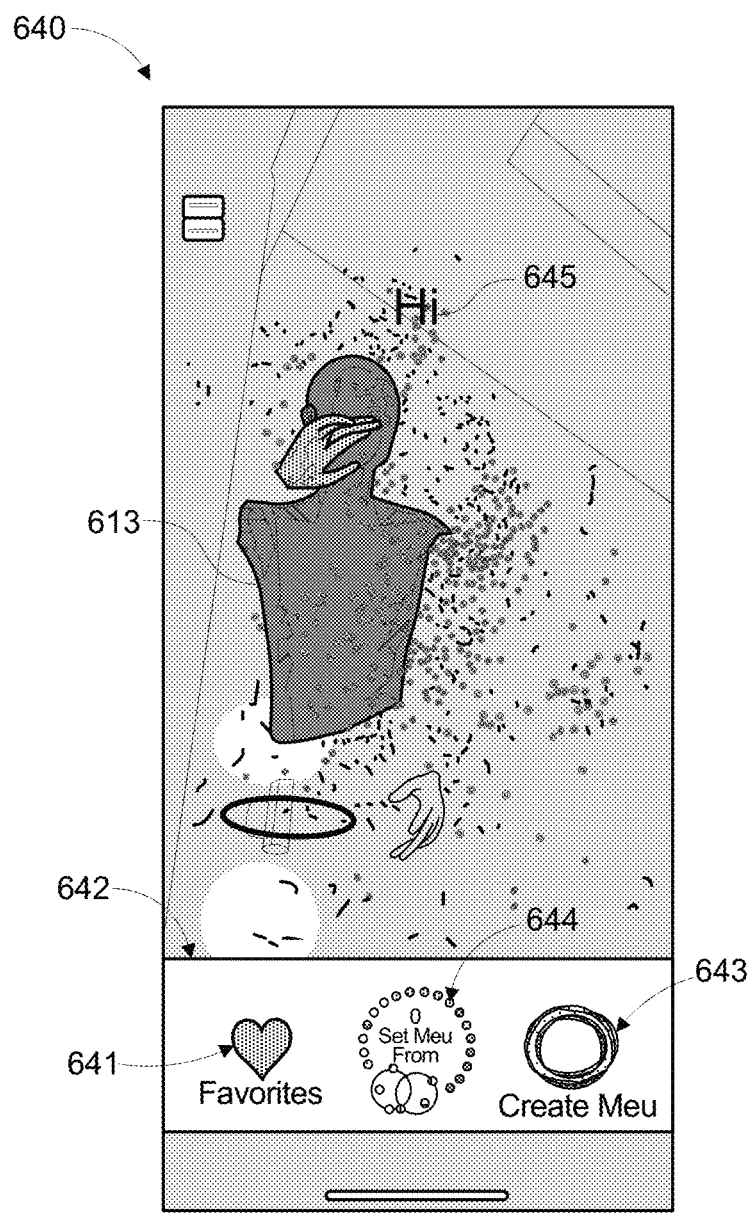
FIG. 6D is a representation of a screenshot from an exemplary implementation of the invention using mobile AR on an iPhone, illustrating the screen of a recipient device, and illustrating a timepoint in the viewing of 3D human movement message from sender comprising blowing a kiss, and illustrating a visual overlay with a sent text message saying "Hi."
Figure 6E:
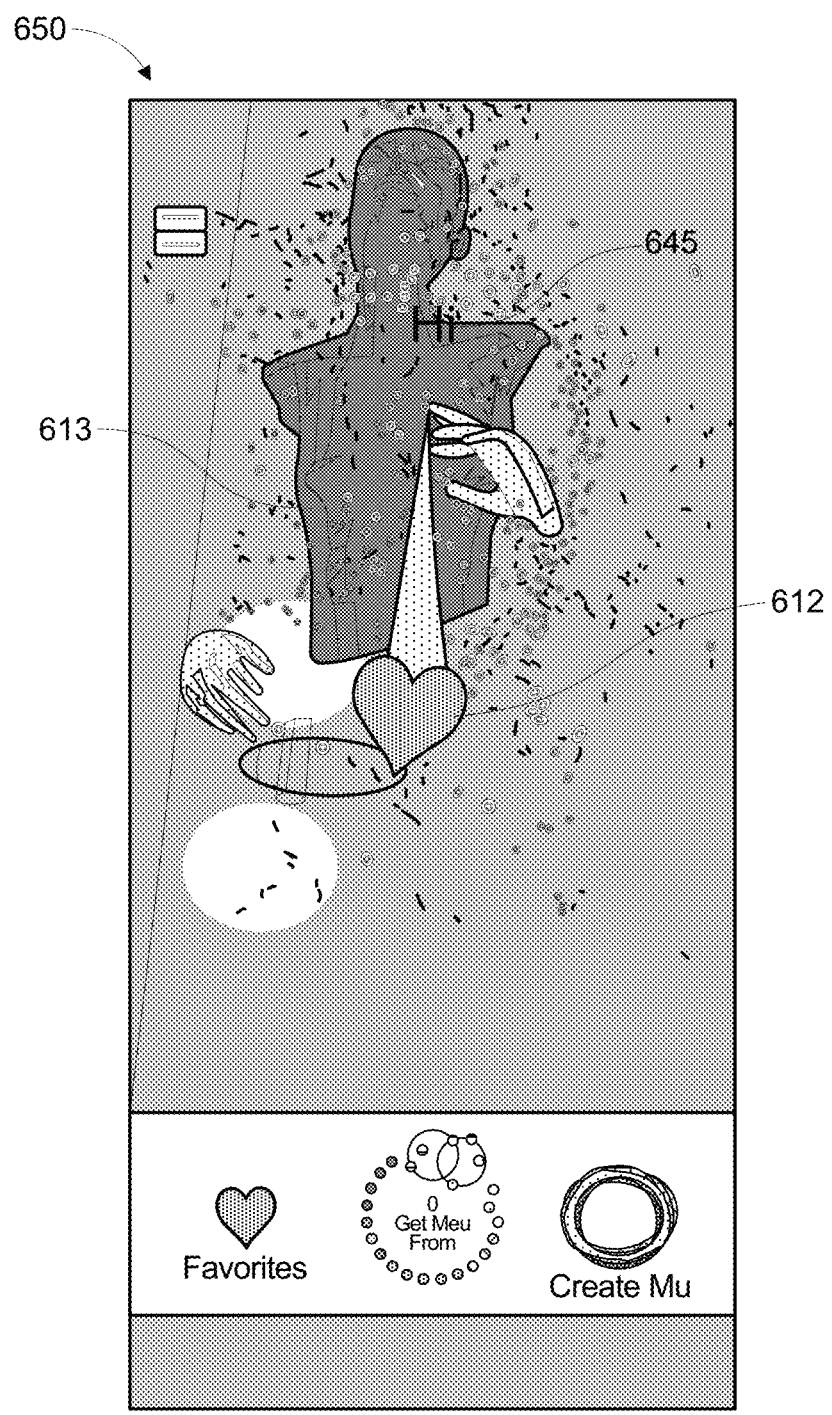
FIG. 6E is a representation of a screenshot from an exemplary implementation of the invention using mobile AR on an iPhone, illustrating the screen of a recipient device, and illustrating a later timepoint in the viewing of 3D human movement message from sender comprising blowing a kiss, further illustrating a visual overlay of a graphical representation of the kiss being blown, and illustrating a visual overlay with a sent text message saying "Hi."
Figure 6F:
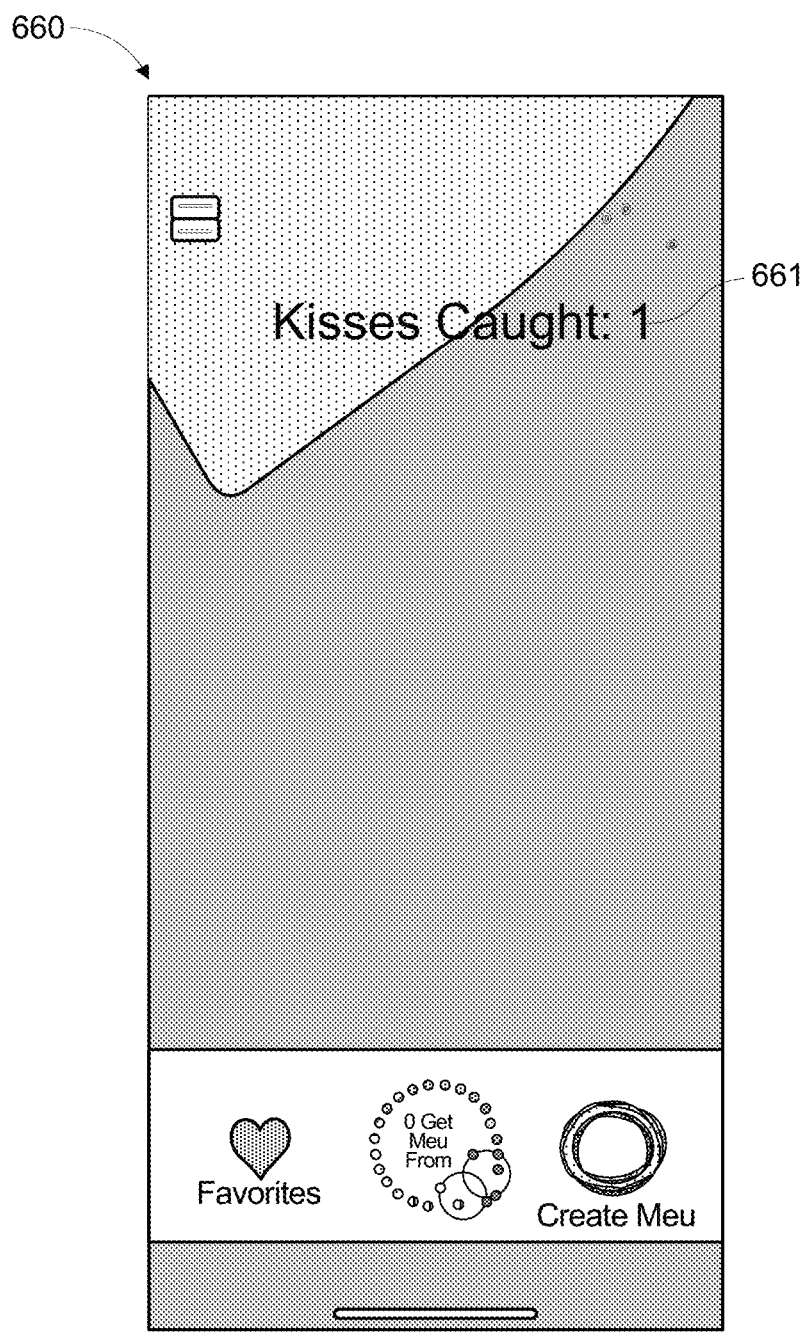
FIG. 6F is a representation of a screenshot from an exemplary implementation of the invention using mobile AR on an iPhone, illustrating the screen of a recipient device, and illustrating another timepoint in the viewing of a 3D human movement message from sender comprising blowing a kiss, further illustrating a visual overlay of a graphical representation of the kiss having been caught by recipient (as part of the game "hearts"), and showing the text "Kisses Caught: 1."

More specifically, 3D movement object 613 is generated based on sender 611's movements as shown in screenshots 610 and 620 in FIGS. 6A and 6B, respectively; transmitted as shown in screenshot 630 of FIG. 6C; and then received and rendered on a recipient device as shown in screenshots 640, 650, and 660 of FIGS. 6D, 6E, and 6F, respectively. Screenshots 610 and 620 in FIGS. 6A and 6B, respectively, also show control menu 614, with control button 615 ("Back to Inbox") and 616 ("Recording"), the latter of which is selected in order to begin the capturing and creating process. Screenshot 620 in FIG. 6B shows a later part of the sender's 3D movement input, where sender 611 raises her arm, as reflected by the raised hand 623 of 3D movement object 613, thereby sending off the virtual heart 612 to the recipient.

Together, the rear camera and the ARKit framework discussed above, along with the other hardware and software needed for them to perform their functions, thus comprise a suitable 3D motion capture means 103, but one of skill will recognize that other suitable 3D motion capture means include comparable hardware and software configurations on other portable devices such as those running Android, on desktop and console systems, and in VR systems.

While motion capture may be accomplished with a camera (such as a smartphone camera, or a depth camera utilizing Intel® RealSense™ or similar technology), 3D motion capture means also include optical (including active, passive, and semi-passive), inertial (e.g., gyroscopes, accelerometers), mechanical, and magnetic systems, as well as systems implemented using Wi-Fi (e.g., WiCapture, WiTrack) or Ultra-WideBand (UWB) technology.

Other suitable 3D motion capture means 103 include volumetric video capture means. In some embodiments, volumetric video capture means include the use of multiple cameras (and camera perspectives), digital graphics processing, photogrammetry, and other multi-sensor and/or computation-based approaches used in combination to generate volumetric 3D video. For example, volumetric video data can be captured using a mesh-based approach, e.g., a 3D triangle mesh as with the geometry used for computer games and visual effects, or using a point-based approach, e.g., volumetric 3D data represented by points/particles in 3D space carrying attributes such as color and size. Exemplary volumetric video capture means include or use HOLO-SYS™ Volumetric Video Capture System (4Dviews); Mixed Reality Capture Studio, Kinect 4 Azure, and Azure Kinect Developer Kit (DK) (Microsoft); Aspect 3D (Level Five Supplies Ltd.); Depthkit Studio; Mantis Vision handheld 3D scanners, 3D Studio 3iosk, and Echo software kit; IO Industries volumetric cameras, sensors, and software; the Microsoft Kinect 4 Azure and Azure Kinect Developer Kit (DK); and Intel® RealSense™.

Using the iOS device's rear camera, the 3D movement input of sender 101 is captured. It will be readily appreciated that any 3D movement input, and the underlying movement or series of movements that it represents (in the exemplary screenshots of FIGS. 6A-6F, the underlying movements are of sender 611 blowing a kiss), will have a start and end time. How such start and end times are selected represents a design choice to be left to the ordinary artisan, but may for example be implemented based on user activation (e.g., screen taps or button presses, voice initiation and termination), with timers including countdown timers, through motion analysis software (i.e., using software to automatically determine the start time and/or end time, by analyzing features of the movement itself), and the like, and ultimate start and end times may be altered with post-capture editing.

It also should be readily appreciated that each 3D movement input is in fact a series of timepoints, from the start time through the end time, the total number of which is determined by the particular frame rate. Typical frame rates for motion capture systems include 30 frames per second (fps) and 60 fps, but depending on the system and its use, may be lower, such as 24 fps, or higher, such as 100 fps, 120 fps, 160 fps, 200 fps, 400 fps, or even 10,000 fps and above.

Three-dimensional motion capture generally is the process of tracking motion in 3D and converting it to data. In some embodiments, a suitable 3D motion capture means 103 tracks the motion in 3D of sender 101, by capturing joint positions and rotations across time. Herein, the term "joint" shall have its ordinary meaning in the field of motion capture, i.e., a potential point of articulation on a skeleton model. While joints thus may correspond to anatomical joints, they may also simply represent a portion of a model that can be moved or deformed in some way.

In the embodiments that use ARKit, joints may include: (1) torso joints, i.e., the hip joint, which is the root of the ARKit joint hierarchy, and seven spine joints; (2) head and neck joints, i.e., four neck joints extending from the spine, as well as joints for controlling the head, eyes and eyelids, nose, chin, and jaw; (3) arm and shoulder joints, i.e., three joints, representing the shoulder, elbow, and wrists; (4) leg and foot joints, i.e., joints for moving the upper legs, lower legs, feet, and toes; and (5) hand joints, i.e., the thumbs which each have four joints, and the eight fingers each comprised of five joints, and which all descending from the hand joint.

Depending on system and design requirements, different joints can be selected, and it should be understood that the ultimate selection of joints, and the choice of total number of joints, will be for the ordinary artisan as part of the implementation of the invention using the practice of ordinary skill. It should be readily appreciated that, while expressivity may increase with greater numbers of joints, there is no specific minimum number required by the invention.

Joint positions and rotations can be captured as 3D movement data in various forms. Joint positions are typically represented by a coordinate system in 3D that uses +y for up, +z for forward, and +x for right, but other systems are possible. Rotations in 3D can be represented, for example, by Euler angles (i.e., roll, pitch, yaw), or more preferably by quaternions. In 3D space, any rotation or sequence of rotations of a coordinate system about a fixed point is equivalent to a single rotation by a given angle θ about a fixed axis that runs through the fixed point. Quaternions encode this axis-angle representation in four numbers, and can be used to apply the corresponding rotation to a position vector, representing a point relative to the origin in 3D space.

Accordingly, each joint can be represented by a 3D position vector {x,y,z} and its quaternion, at each timepoint or frame of a 3D movement input. For a motion in 30 fps, one second of motion at each joint would thus be captured as a set of 30 such representations.

Simultaneous with or subsequent to their capture, the captured 3D movement data can be extracted, combined with other data including metadata, compressed, modified, manipulated, or otherwise processed by processing means 105, to create a 3D movement data package. In embodiments using ARKit, processing means 105 may be a software application programmed to communicate with the ARKit framework so as to obtain captured 3D movement data therefrom. The design of such software applications will be understood to be within the practice of ordinary skill, but as an example, in some preferred embodiments the software application may be built using the Unity game engine developed by Unity Technologies, a cross-platform engine that supports development for numerous platforms across mobile, desktop, consoles, and VR.

Captured 3D movement data can be processed so that data are only extracted for specific joints, whether selected by a user or by the designer. Captured 3D movement data also can be processed, for example, to reduce the frame rate (e.g., by only selecting half of the frames). And as discussed in greater detail in Example 2, processing can combine captured 3D movement data with information relating to avatars, filters, games, or other sender-selected parameters and data.

A 3D movement data package, as defined above, represents the 3D movement data of the sender, along with its metadata and any additional data. It moreover will be in a format suitable for sending (i.e., as a 3D movement data message) or storing (i.e., as a 3D movement data file). And as further discussed below, a 3D movement data package is also in a format suitable for ultimately rendering to an output as a viewable 3D movement object, viewable to a recipient, thereby accomplishing a goal of some embodiments of the invention.

In some embodiments, the 3D positional vectors and 4D quaternions captured by 3D motion capture means 103 are further processed by processing means 105 to compress them so they take up less memory, transfer faster and use less bandwidth, or otherwise use less computing resources. Various suitable data compression algorithms will be known to one of ordinary skill. In one embodiment, the vectors and quaternions are compressed to three decimal points and concatenated into strings, with each string mapped to a particular body position or rotation. To further elucidate this embodiment, sample strings, representing the position and rotation of the head and hands for two frames (i.e., at two timepoints), are as follows:

"rHandPos": "1.068: 0.951:−0.683: 1.068: 0.951:−0.683: 1.069: 0.955"

"rHandAng": "−0.37:−0.091: 0.543:−0.748:−0.369:−0.097:0.544:−0.747"

"lHandPos": "0.232: 0.762:−0.781: 0.232: 0.762:−0.78: 0.233: 0.762"

"lHandAng": "−0.452:−0.473: 0.085:−0.751:−0.453:−0.473:0.083:−0.751"

"headPos": "0.469: 1.081:−1.035: 0.468: 1.081:−1.035: 0.467: 1.081"

"headAng": "−0.011:−0.358: 0.015:−0.934:−0.011:−0.359:0.015:−0.933"

After a 3D movement data package is created, as above, it can be sent as a 3D movement data message and/or stored for later retrieval. For either, the 3D movement data package is first stored to volatile memory by recording means 106. Depending on the embodiment, the processing means 105 and the recording means 106 may comprise the same hardware, software, or combination of hardware and software, or may be separate modules, and processing and recording may take place simultaneously, sequentially (e.g., where processing and recording are of the entirety of a 3D movement data package), or alternatingly (e.g., where processing and recording are of separate frames or portions of a 3D movement data package), and in any order.

In embodiments where a 3D movement data package is permanently stored, it may be stored on local permanent storage 107 on the sender device 116, on local permanent storage 111 on the recipient device 118, and/or on remote permanent storage 109, such as cloud storage in cloud 117.

In some embodiments, for example, sender 101 may choose to store a sent movement data message. "Permanent storage" should be understood to mean any storage device or collection of devices that retains data when unpowered, such as a hard drive or solid-state drive (SSD) (i.e., "persistent" as opposed to "volatile" memory).

A 3D movement data package may be stored as a 3D movement data file in any suitable format that allows for storage and retrieval of data, including relational databases using tabular relations (e.g., SQL), non-relational databases (e.g., NoSQL), standard motion capture data formats (e.g., Biovision Hierarchy Animation .bvh files), and others. In some embodiments, the permanent storage is a dedicated 3D movement data server, which may additionally store 2D media and other data. It will be understood that stored data may optionally be aggregated, indexed, compressed, or otherwise modified, and may be extractable or retrievable for use in other processes or by other systems, as may be further elucidated by reference to Example 5.

A 3D movement data package may be sent as a 3D movement data message between sender device 116 and recipient device 118 using any suitable sending means 108 and receiving means 110. Such sending means and receiving means include those means capable of sending and/or receiving over cellular networks (e.g., 3G CDMA/GSM, 4G LTE, 5G NR), over Wi-Fi, over Bluetooth, over AirPlay, by mobile broadband, by wired internet, or by any other communications or file transfer protocols known in the art.

In some embodiments, sender device 116 and receiver device 118 may be hard-wired or otherwise directly connected. In other embodiments, it will be understood that a 3D movement data message need not be sent directly from a sending means 108 to a receiving means 110, but may be transferred between any number of intermediary hardware and/or software modules, network devices, or servers, e.g., as may reside on cloud 117.

It also will be understood that the 3D movement data package may be compressed, encrypted, or otherwise altered, either by sending means 108 before sending, or by an intermediary module, device, or server during transmission. If a 3D movement data message is received by receiving means 110 in a format that is compressed, encrypted, or otherwise altered, it will be within the practice of ordinary skill to decompress, decrypt, or otherwise return to renderable format such 3D movement data message.

Once received by recipient device 118, a 3D movement data message may be viewed by recipient 115 (or, in some embodiments, received by more than one recipient device 118 and/or viewed by more than one recipient 115). It also may be stored on permanent storage 111. A 3D movement data package may be stored before and/or after it is viewed, and storage may be by default software rule or by user selection. For instance, recipient 115 may not be available or may not wish to view a 3D movement data message immediately, and thus it may be saved by the decision of recipient device 118 or recipient 115 for later viewing. Or, recipient 115 may view it immediately, and then decide to store it permanently for repeat viewing, e.g., in a "saved" folder or a "favorites" folder. One of skill will understand that many design choices involving storage 111 (and 107 and 109) are possible, and within the practice of ordinary skill.

As shown in FIGS. 6D-6F, a favorites folder or the like is used in a preferred embodiment, so that the recipient may save special 3D movement data files like a child's cutest dance, a partner's hug, or a friend's secret handshake. More specifically, the recipient may select the "Favorites" heart-shaped button 641 in control menu 642 as shown in screenshots 640 and 650 of FIGS. 6D and 6E, respectively, in order to store the received 3D movement data message.

In some embodiments, viewing a 3D movement data package is made possible with 3D motion rendering means 112 and output means 114. A suitable 3D motion rendering means 112 is any hardware, software, or hardware/software combination (whether as a single module or combination of modules) that is capable of rendering a 3D movement data package as a 3D movement object, regardless of the specific technical basis on which such rendering is performed (e.g., whether rendering is generated ahead of time (pre-rendered) or in real-time, regardless of choice of specific rendering algorithm, etc.).

Many rendering algorithms are known to ordinary artisans, and software used for rendering may employ any number of different techniques to obtain a final animation. For instance, in embodiments that capture 3D movement data using a time series of positional vectors and quaternions to represent joints across time t, a suitable 3D motion rendering means 112 will be able to recreate a skeleton model comprising those joints, in like positions. That time series of 3D movement data is used to animate the skeleton model, using mathematical processes known in the art, such as inverse kinematics, combined with suitable computer animation techniques (e.g., skeletal animation or "rigging," and "skinning").

In one preferred embodiment, to create an aesthetically balanced distribution of particles, a custom particle engine is implemented on a graphics processing unit (GPU). In this embodiment, rather than spawning a particle evenly across a polygon mesh (i.e., the collection of vertices, edges, and faces that defines the shape of an object), different distributions are calculated at run time. Each particle saves its barycentric coordinates and references to its nearest vertices. A new "spawn position" is then calculated, by first skinning the surrounding vertices in reference to their bone transform/weights, and then placing the spawn position using its stored barycentric coordinates. However, various other rendering and animation techniques can be utilized without departing from the scope of the invention.

Where, in certain embodiments, the captured 3D movement data is processed to reduce the frame rate (e.g., from 60 fps to 30 fps), or where a higher rendering frame rate is otherwise desired, 3D motion rendering means 112 may utilize an interpolation algorithm to smooth the data. It will be appreciated that 3D movement data generally can be rendered by a 3D motion rendering means 112 using numerous variations in style and practice, depending on system and design requirements.

A suitable 3D rendering means 112 for purposes of embodiments of the invention need only be minimally capable of outputting a 3D movement object, viewable to the recipient, that is a like representation of the 3D movement data package captured (although, as should be apparent, it also may be modified or altered, according to designer goals or user parameters). It is therefore contemplated that the ordinary artisan may implement the 3D rendering in a variety of ways, utilizing different particle systems, different reflection, scattering, and surface shading techniques, different color palettes and background images, different visual effects, and the like.

In some embodiments, the 3D motion rendering means 112 will optionally use sender-defined parameters, which may or may not be dynamically updated by a sender, sent as part of the 3D movement data message, to render the ultimate 3D movement object. As noted above, such parameters may include metadata indicating that the 3D movement data should be rendered using a particular avatar, having specific body modifications (e.g., wings, a tail, tentacles), incorporating photographic and video data (e.g., to render a 3D movement object having the sender's own face and/or body, or another particular face or body), or the like. An ordinary artisan will appreciate that many solutions exist to permit such modifications to be made; for example, the data representing different avatars and other alterations can be locally or remotely stored, received from the sender, or obtained from a third-party server (including, as an example, customized avatars that may be offered for in-app purchase), but such solutions are design choices that can be made with ordinary skill.

Ultimately, the 3D movement data message is rendered so as to be viewable to recipient 115, using output means 114. Suitable output means will be understood to include the screen of recipient device 118, whether a smartphone, tablet, or other personal device, or a VR headset. In other embodiments, output means 114 may be (or may additionally include) a monitor, a television, a projection system, a holographic display, a stereo display or 3D display, or any other output screen which may be physically separate from but operationally or functionally coupled to recipient device 118.

Preferably, but optionally, sender 101 may view her own 3D movement input on output means 104. Suitable output means are understood to be those comparable to output means 114 (e.g., the screen of sender device 116, a VR headset, a monitor or TV, a projector or holographic display, a stereo display or 3D display, etc.). When 3D movement is rendered on output means 104, it will be understood that processing means 105 further includes suitable 3D motion rendering means, whether as hardware, software, or hardware/software combinations, comparable to 112. In certain preferred embodiments, the sender avatar is rigged as a mirrored puppet, allowing for real-time feedback of the sender's own movements, as shown by example of 3D movement object 613 in screenshots 610 and 620 in FIGS. 6A and 6B, respectively.

In some embodiments, the 3D motion rendering performed by processing means 105 will optionally use sender-defined parameters, so that sender 101 is therefore able to select and try on different avatars, experiment with various filters and feedback, and otherwise set and change parameters and view and interact with her 3D movement input in real time, whether or not it is also being captured. Depending on the embodiment, various parameters can be determined based on the sender's 3D movement; alternately, they can be determined by other input, or through choices made through an alternate input, using an optional additional input means 102, such as voice, the touchscreen of smartphone or tablet device 116, or controls of VR device 116.

Additional input means 102 also may include sensing means for responding to (i.e., providing feedback based on) or recording (along with 3D movement data, whether ultimately included in a 3D movement message or not) physiological, physiometric, or biometric data such as that relating to cardiovascular and pulmonary functions (e.g., pulse rate, heart rate variability (HRV), ECG traces, blood oxygenation, respiration rate, temperature or $CO_2$ content of exhaled air, heart sounds, body resonance), brain activity (e.g., encephalography such as electroencephalography (EEG), quantitative EEG (qEEG), magnetoencephalography (MEG), electrocorticography (ECoG), functional magnetic resonance imaging (fMRI), positron emission tomography (PET), nuclear magnetic resonance (NMR), spectroscopy or magnetic resonance spectroscopy (MSR), single-photon emission computed tomography (SPECT), near infrared spectroscopy (NIRS), functional NIRS (fNIRS), or event-related optical signal (EROS)), electrodermal activity (e.g., skin conductance), and other such alternative input types.

Figure 2:
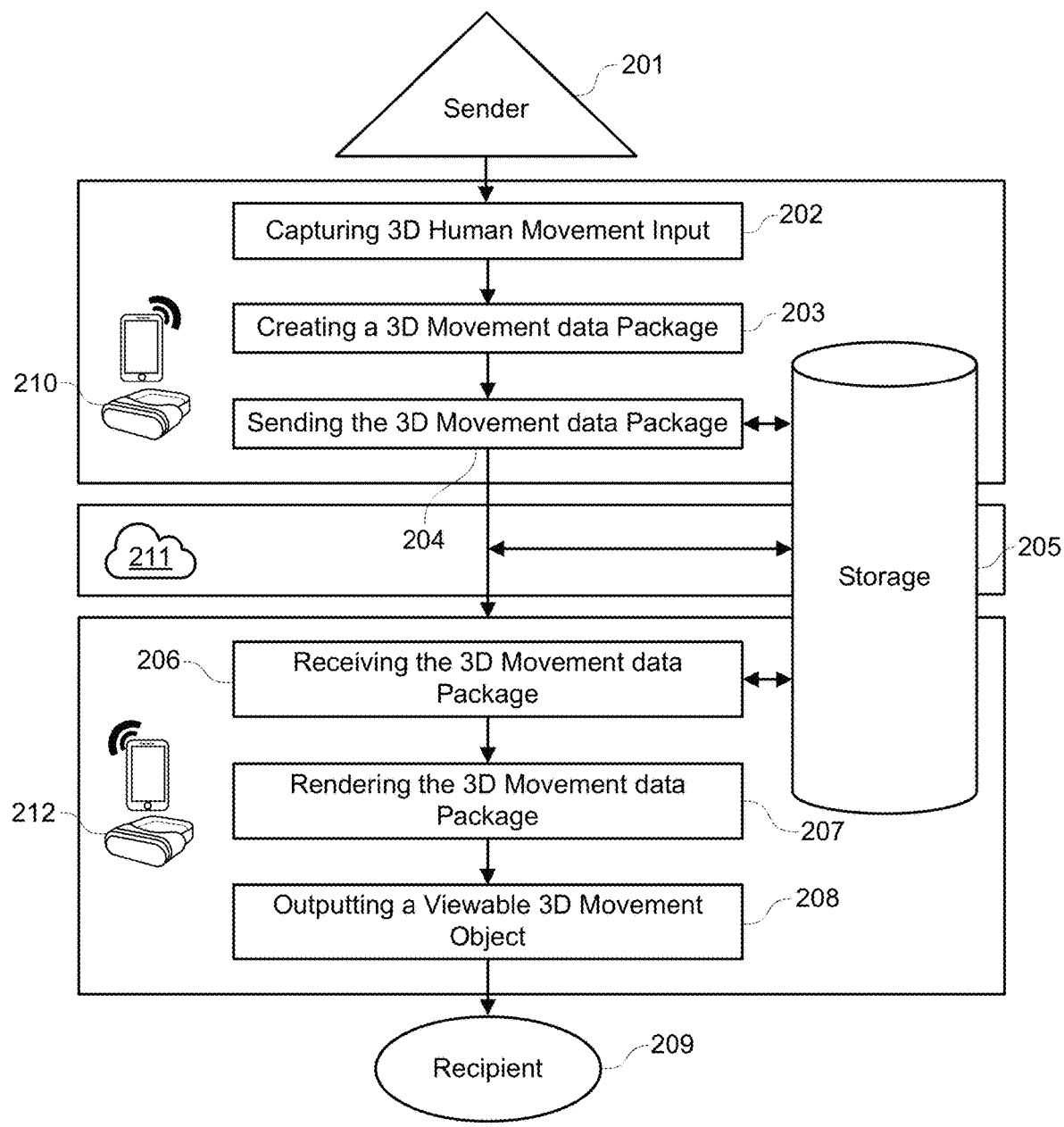
FIG. 2 is a flow diagram illustrating embodiments of the methods of communication using 3D human movement data of the invention, illustrating an exemplary flow from a sender to a recipient, according to an implementation. Where modules or steps are connected with arrows illustrated using dashed lines, they shall be considered optional to the exemplary implementation of the illustrated embodiment.

With the description and definitions above now understood, reference is made to FIG. 2 to further understand various exemplary embodiments. Using FIG. 2, it again can be demonstrated how a sender, who wishes to send a 3D movement data message of her blowing a kiss to a recipient, may do so.

In a first step 201, the sender makes the physical movement of blowing a kiss.

In a second step 202, that human movement input is captured by sender device 210. As above, the step of capturing 3D movement input 202 may be implemented by a 3D motion capture means 103.

A 3D movement data package is created in a third step 203, which may be implemented using a processing means 105 and a recording means 106, according to the teachings above.

In a fourth step 204, that 3D movement data package is sent, which may be implemented using a sending means 108.

In an optional fifth step, the 3D movement data package may be stored on storage 205. Although styled as a "fifth" step, it will be understood that the 3D movement data package may be stored by sender device 210 before sending, may be stored by receiver device 212 after receiving, and/or may be stored by cloud 211 during transmission, and that storage 205 therefore may be local storage, remote storage, or a combination thereof (as with permanent storage 107, 109, and 111). In these embodiments, storage 205 refers to permanent storage, and it will be understood that even if never stored in such permanent storage, a 3D movement data package may nevertheless reside in volatile memory in one or more copies, at multiple locations, and at any step(s) in the methods here described. Devices 210 and 212, and cloud 211, shall be understood with reference to devices 116 and 118, and cloud 117, above.

In a sixth step 206, the 3D movement data package is received by recipient device 212, as implemented for example by a receiving means 110.

In a seventh step 207, the 3D movement data package is rendered, for example by a 3D motion rendering means 112.

In an eighth step 208, a viewable 3D movement object is output, for example on an output means 114. That viewable 3D movement object, in the example illustrated by FIGS. 6A-6F, is the sender blowing a kiss.

In a ninth step 209, the recipient views the 3D movement object 613 of the sender, and receives, in this exemplary embodiment, the shared kiss 612 shown in screenshot 650, FIG. 6E.

Example 2: Communication of Synesthetic Movement Data from Sender Perspective

Figure 3:
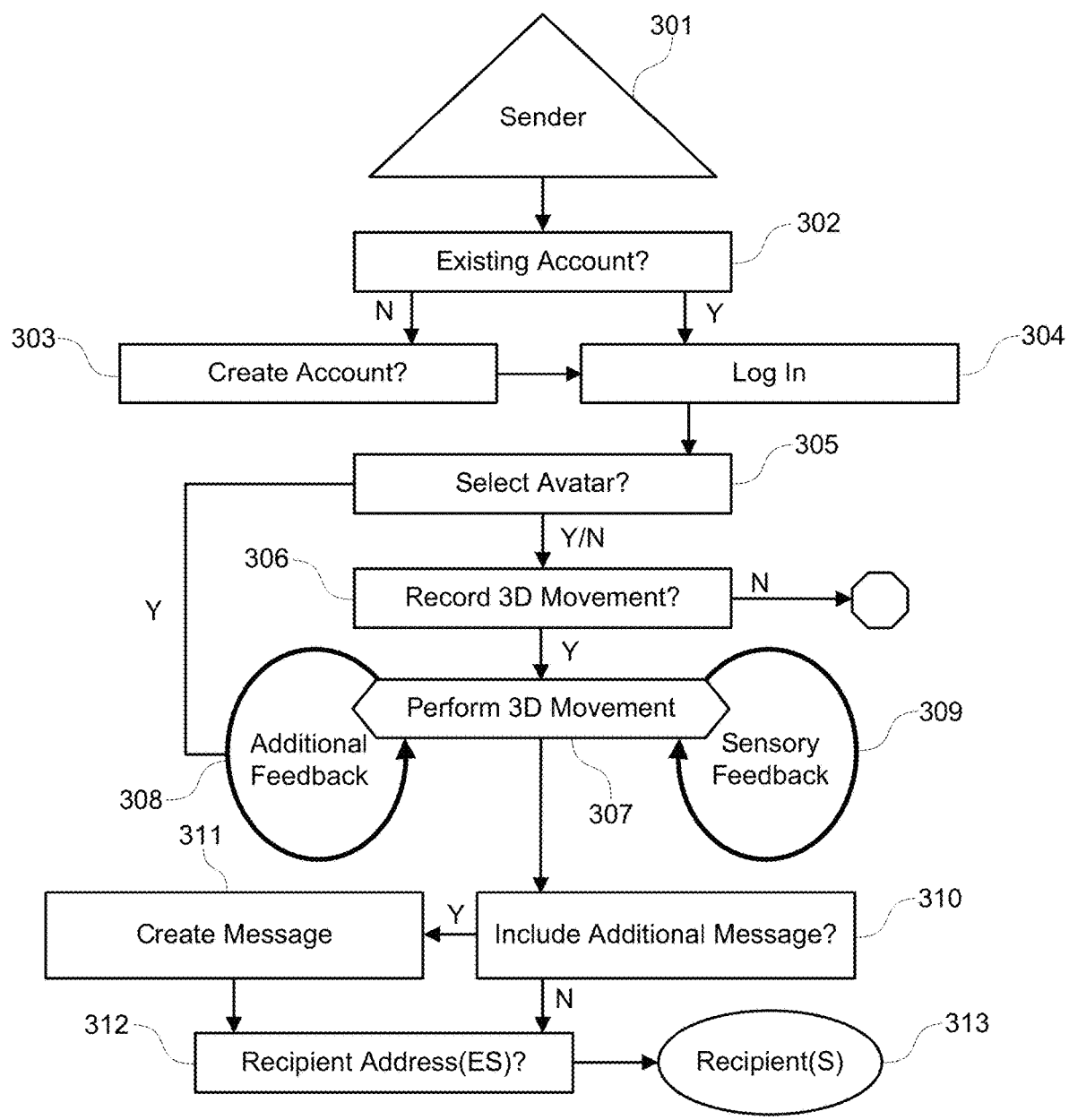
FIG. 3 is a flow diagram illustrating embodiments of the methods of communication using 3D human movement data of the invention, illustrating an exemplary flow from a sender to a recipient, from the perspective of the sender, according to an implementation.

Having disclosed various embodiments viewed in light of the overall process from sender to recipient, in this Example embodiments will be described in further detail from the perspective of a sender, by reference to the flow chart of FIG. 3.

In this Example, it will continue to be assumed that a sender wishes to send a recipient a 3D movement data message of her blowing a kiss. With that wish in mind, sender 301 opens the application on her sender device 116 to initiate the method. In this exemplary implementation, the application is understood to be stored and run on device 116, and to be operationally and functionally coupled with the hardware and software so comprising, and therefore together they comprise 3D motion capture means 103, processing means 105, recording means 106, permanent storage 107, and sending means 108, along with additional input means 102 and output means 104, all operating as above described.

Upon opening the application, sender 301 is first asked whether she has an existing account 302. Depending on her choice, she is able to create a new account 303 or log in using her existing account credentials 304. While logging in may be used as one means to identify and authenticate a sender, in other embodiments the sender may have the option to bypass log in (or, e.g., to log in as a "guest" or as "anonymous"), or a sender may be automatically logged in based on user authentication managed by another application (e.g., managed by Google or Facebook) or through the operating system (e.g., iOS), or via device authentication.

After optionally logging in (or otherwise being authenticated, if authentication is required), sender 301 may select an avatar 305, the choice of which may affect the 3D movement that is captured or provide additional feedback 308. Sender 301 is then presented with the choice of whether to record a 3D movement 306. Although by selecting "no," the exemplary flow of FIG. 3 is shown to terminate, it is understood that sender 301 may nonetheless continue to interact with the application as discussed above. In some embodiments, sender may interact with the application for as long as she desires, and experiment with various movements and filters before sending a message.

More specifically, as illustrated in screenshots 640 and 650 of FIGS. 6D and 6E, respectively, when the user wishes to create a message, she can use the button "Create Meu" button 643 in control menu 642. In the exemplary implementation herein, a "Meu" will be understood to be a "3D human movement data message" or a "3D movement data message." By selecting "Create Meu" button 643 illustrated in screenshots 640, 650, and 660 of FIGS. 6D, 6E, and 6F, respectively, the user can then perform a 3D movement 307 to be captured. Sensory feedback 309 may be provided depending on sender movement data, in light of sender-defined parameters. Examples of feedback include auditory, visual, haptic, or multimodal.

For instance, motion detection algorithms may be used to provide feedback by analyzing higher-level features of the 3D movement data in real time. Depending in part on choice of filters, feedback may be provided based on one or more specific higher-level features such as smoothness of motion, range of motion, reaction time to a cue, gait size and speed, limb flexibility, and closeness of match to a predefined 3D movement (using a suitable function to determine closeness of match or goodness of fit, or any one or more of such other higher-level features, as would be understood by one in the art, using the practice of ordinary skill).

Non-limiting examples of how to calculate such higher-level features are as follows. Smoothness of motion may be determined based on the amount of trajectory or velocity adjustments during a specific movement, reflecting movement intermittency and movement coordination. Smoothness may also be calculated using mathematical analysis, wherein the smoothness of a function is a property measured by the number of continuous derivatives it has over some domain. Range of motion may be determined using the measurement of the amount of movement around a specific joint or body part (e.g., the extent of movement of a joint, measured in degrees of a circle). Reaction time to a cue may be determined as the time between a stimulus (the cue) and a response. Gait size may be determined based on the distance between successive points of initial contact of the same foot (i.e., stride length) or the distance between the point of initial contact of one foot and the point of initial contact of the opposite foot (step length). Gait speed may be determined based on the time one takes to walk a specified distance on a surface, or based on the rate in steps per minute (cadence). Limb flexibility may be determined based on the anatomical range of movement in a joint or series of joints (as compared to, e.g., an average or defined reference).

All such higher-level features may be calculated based on a single determination or the mean of multiple such determinations, and may be averaged across multiple features (e.g., the mean of multiple reaction times, mean limb flexibility at a single limb or averaged across multiple limbs, range of motion at a single joint or averaged across arm joints, leg joints, all joints, and the like, as will be readily appreciated).

Closeness of match and goodness of fit functions include any one or more of, as well as such others as will be known to those in the art: Bayesian information criterion; Kolmogorov-Smirnov test; Cramer-von Mises criterion; Anderson-Darling test; Shapiro-Wilk test; Chi-square test; Akaike information criterion; Hosmer-Lemeshow test; Kuiper's test; Kernelized Stein discrepancy; Zhang's ZK, ZC and ZA tests; Moran test; Pearson's chi-square test; and G-tests. Also contemplated are such regression analyses as coefficient of determination (the R-squared measure of goodness of fit), lack-of-fit sum of squares, reduced chi-square, regression validation, and Mallows's Cp criterion.

In some embodiments the movement data, or various higher-level features extracted from such movement data, may drive both the auditory and visual experience, connecting movement data to color, speed, fade, elasticity, and noise functions of the particles and avatar, as well as an interactive music system that changes based on the sender's movements.

In one such embodiment, adaptive music is created in Fmod using the Fmod Unity plugin, that allows the movement data to change the music track parameters in real time. In preferred embodiments, music is composed specifically to support different filters, and further consists of loops and layers that fade in and out depending on the sender's movements. For example, one filter ("peaceful") uses the position of the hands to control cello and flute loops in the music, while a pose detection algorithm connects an open body posture to a musical "swell" overlay. Another filter ("explosive") uses velocity measurements to control bass and drums, and an average velocity over longer periods to control other portions of the track.

Haptic feedback is also provided in some embodiments, for instance vibrations may be activated when touching an avatar, communicating the sensation of physical presence. Such physical presence enhances the ability to play touch-based mirroring games asynchronously.

In embodiments where disclosed methods and systems are used as part of psychedelic-assisted therapy, haptic feedback also permits a therapist and a patient to interact by touch.

A motion detection algorithm also can be utilized to detect closeness of match to a predefined 3D movement and thus recognize specific 3D movements representing different gestures or body language, and to create 3D visualizations that enhance them. Reference is made to FIGS. 6A and 6B, demonstrating sender 611 (or, equivalently, sender 301) blowing a kiss 612 to a recipient(s) (i.e., recipient 313). More specifically, a motion detection algorithm is used to recognize when the sender's hand extends out and up as shown in screenshot 620 of FIG. 6B from its previous position (i.e., at the mouth as shown in screenshot 610 of FIG. 6A), and to visually output heart(s) 612 which mimics and continues the hand's movement from the mouth of the sender upward and outward (e.g., as in the prosocial game "hearts," as above). Thus, when the sender 301 blows a kiss to recipient 313, not only will the recipient see the 3D movement itself, but the recipient will also see a 3D visualization that includes, for example, hearts coming out of the sender's mouth, timed with her movements (and can further interact with that visualization, as below). Thus, it will be understood that any visualization or feedback may be output not only to the sender, but also may be saved as part of the 3D movement data package, and where such feedback is saved as part of the 3D movement data package, it also may be rendered or otherwise played for the recipient. Visualizations and feedback may also be output to a recipient by analyzing features of the 3D movement data of sender during rendering on a recipient device.

With reference again to FIG. 3, now that sender 301 has performed the desired 3D movement, she will be asked (according to this exemplary implementation) whether she wishes to include an additional message, such as a text message 310, when her 3D movement data message is transmitted. Should she wish to create such a message 311, it will be included with the 3D movement data message as described in detail above. Reference is made to FIG. 6C, illustrating screenshot 630, in which the user may use input box 631 and keyboard 632 to send an additional message (e.g., "Hi" 633). In other embodiments, additional messages could include virtual gifts (e.g., virtual flowers or puppies), which in some embodiments can be monetized as in-app purchases.

Sender 301 is next asked to which recipient addresses she wishes to send her 3D movement data message 312. It will be readily appreciated that the implementation of an address feature can utilize various identifiers including display names, actual names, email addresses, phone numbers, assigned IDs, or any other identifying information, and recipients can be individuals, or groups, including sender-defined groups (e.g., friends, family, team members, coworkers, etc.) or application-defined groups (e.g., current players of a particular game). For example, in the implementation demonstrated in FIG. 6C, sender 301 may choose to send a 3D movement data message to a sender-defined group (by selecting slider 634 under "Send to all friends"), to an application defined group (by selecting slider 635 under "Send to Meu team"), or to a specific individual recipient (by entering it in box 636 displaying the grayed out text "Type here and click on friend" under the text "Type Friend Display Name or Email"). Finally, the 3D movement data message is then transmitted to the chosen recipient(s) 313.

In some embodiments, a gif creation tool also may be used to turn the 3D movement data message into a 2D gif, which may further include sender-defined filters and text. Such 2D gifs may be sent in addition to a 3D movement data message, or may be sent in the alternative, such as to recipients who do not have a suitable application yet installed to render the 3D message.

In other embodiments, rather than be transmitted to a device to be output to a screen, and viewable to a recipient, a 3D movement message will be transmitted to a device to be output so as to control a puppet, toy, robot, or similar physical device. In these embodiments, rather than be graphically rendered as an animation, the 3D movement data will be converted to control signals to operate a mechanical apparatus, using methods known to those of ordinary skill (e.g., mapping the captured motion of human joints to like joints of the mechanical apparatus, mapping other captured human movement features to the movement of the mechanical apparatus, and the like).

Figure 4:
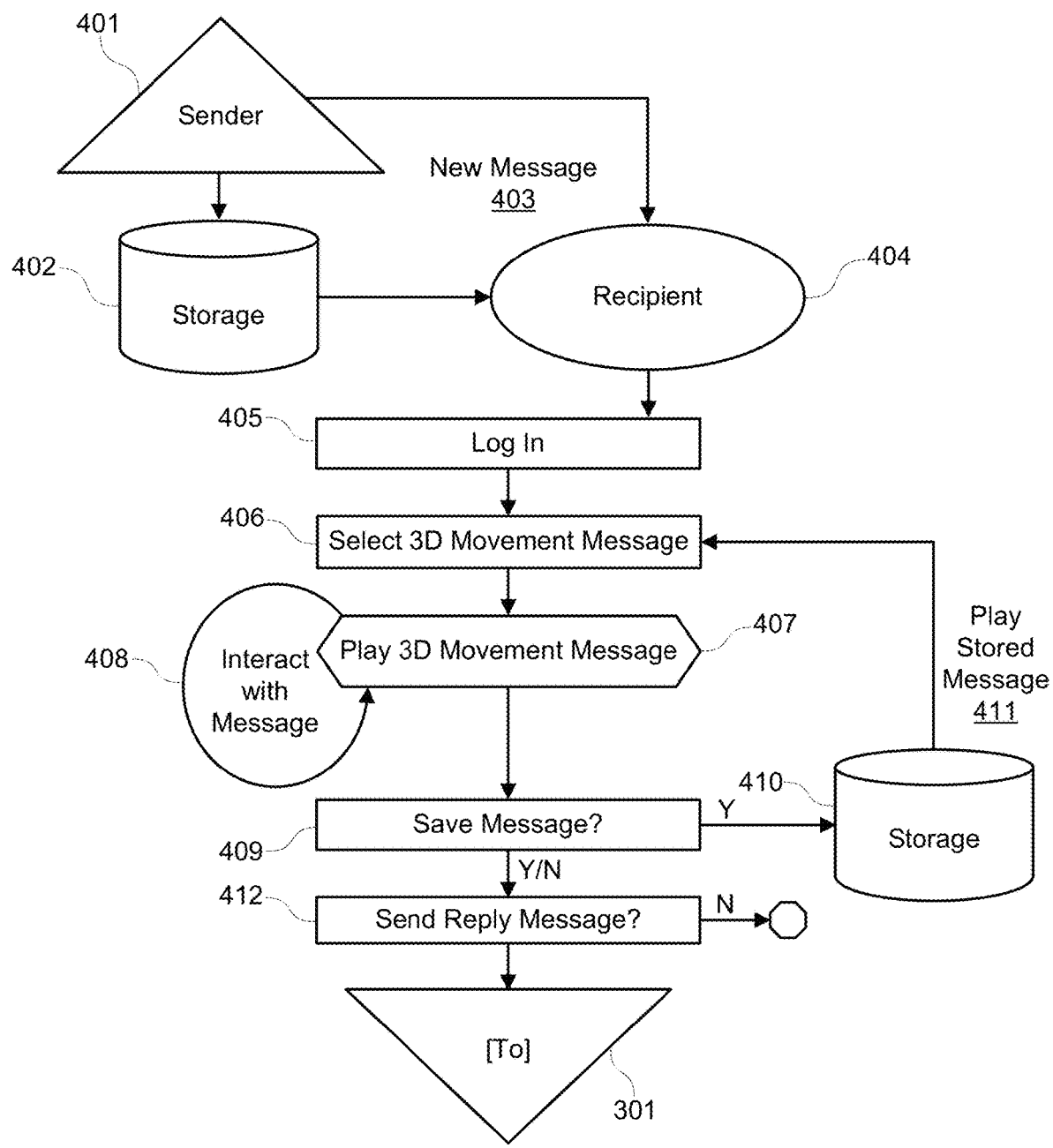
FIG. 4 is a flow diagram illustrating embodiments of the methods of communication using 3D human movement data of the invention, illustrating an exemplary flow from a sender to a recipient, from the perspective of the recipient, according to an implementation.

Example 3: Communication of Synesthetic Movement Data from Recipient Perspective Having disclosed various embodiments viewed in light of the overall process from sender to recipient, and in Example 2 from the perspective of a sender, in this Example embodiments will be described in further detail from the perspective of a recipient, by reference to the flow chart of FIG. 4. In the implementations taken as exemplary for purposes herein, the flow is now presumed to begin where Example 2 concluded.

Taking up where Example 2 left off, it is therefore understood that sender 401 has created a 3D movement message comprising, in the example illustrated in FIGS. 6A-6C, the sender blowing a kiss, and transmitted it to recipient 404. In the exemplary implementation of this Example, recipient 404 first receives a notification (e.g., a sound, vibration, badge, banner, etc.) on a receiver device, to alert recipient to new message 403. In some embodiments, recipient may immediately respond to the alert, and the new message may thus be transmitted from sender without being first stored in permanent storage 402. In other embodiments, recipient may not be aware of the alert, or may ignore the alert, and new message may be saved to storage 402 for later retrieval. In these embodiments, it is immaterial if storage 402 is on sender device, recipient device, another device, and/or the cloud.

To view new message 403, recipient 404 may first log in 405 to the appropriate application software installed (or be otherwise authenticated, if required). Although omitted from FIG. 4, it will be understood that without an existing account, recipient may have the option of first creating one before logging in, as in FIG. 3 (see 302, 303, 304). While logging in may be used as one means to identify and authenticate the proper recipient 404, in other embodiments a recipient may have the option to bypass log in (or, e.g., to log in as a "guest" or as "anonymous"), or a recipient may be automatically logged in based on user authentication managed by another application (e.g., managed by Google or Facebook) or through the operating system (e.g., iOS), or via device authentication.

Once optionally logged in (or otherwise authenticated, if authentication is required), recipient 404 may select a 3D movement data message for viewing 406. It is assumed that recipient will be able to select new message 403 for viewing, but depending on how many other new messages are ready for viewing, and depending on how many saved messages are available for reviewing, recipient may have a number of different messages that could be played, including a stored message 411 from storage 410. In the example illustrated by screenshot 640 in FIG. 6D, the recipient would select the "Get Meu From" button 644 in control menu 642 to select a message for viewing.

Having selected new message 403 for viewing 406, recipient 404 thus plays it as a 3D movement message 407. The 3D movement output that is viewed (i.e., the 3D movement object) corresponds to the 3D movement data package sent and recreates the 3D human movement input that was captured, therefore allowing a 3D human movement to be communicated (see, e.g., FIGS. 6D-6F). If a text message was included (310, 311), sender will be able to view the text message at one or more points during playback of the 3D movement message 407. In the example illustrated by FIGS. 6A-6F, the accompanying text message "Hi" entered as 633 by the sender as shown in screenshot 630 of FIG. 6C is displayed to the recipient as text "Hi" 645 in screenshot 640 of FIG. 6D.

In some preferred embodiments, recipient will be able to interact with the played message 408. For example, as new message 403 is of recipient blowing a kiss, in some described embodiments a parameter is set as part of the 3D movement data message, indicating that the prosocial game "hearts" is selected. In alternate embodiments, "hearts" could be offered as a selection to recipient 404 based on motion detection software running on the recipient device. In some embodiments, when the game "hearts" is played, recipient can utilize recipient's own movement data, during viewing, to "catch" the blown kisses, represented by animated hearts, as they come toward recipient. In some embodiments, further feedback can be provided (e.g., haptic feedback when a kiss is caught), and a score can be displayed. In the example illustrated by FIGS. 6A-6F, the recipient's number/score of received kisses is displayed as "Kisses Caught: 1" 661 in screenshot 660 of FIG. 6F. Recipient 404, in other embodiments, can activate other forces that interact with the avatar's particle system, to create any number of novel types of combined action between sender and recipient.

In some embodiments, novel types of interactions that are impossible in the real world are possible. For example, by playing with scale as one of an avatar's parameters, an extra layer of interpersonal communication is created, and body size becomes an expressive component of communication regardless of one's own actual size. In some such embodiments, the scale of the 3D movement data will be manipulated, while keeping the proportions between the body parts of an avatar equal. In one such implementation, recipient 404 could therefore "miniaturize" the 3D movement object representation of sender 101 and thus "shrink" sender down, so that sender 101 could, e.g., dance on top of the palm of recipient 404. In other implementations, the proportions between the body parts of an avatar could be manipulated. In yet other implementations, scale and/or proportions could be manipulated, and when such techniques are used in combination with different avatars, and with different other techniques of the present disclosure, a variety of novel uses and applications will be readily envisioned.

In some embodiments, size will be manipulated toward therapeutic ends. For example, a patient undergoing PAT such as described below may be given an avatar with, e.g., different body parts or proportions, as part of a therapeutic protocol to manage the distress or symptoms of one or more body dysmorphic disorders.

After new message 403 is played 407, recipient 404 has the option to save the message 409 to storage 410 and/or send a reply message 412. If recipient 404 chooses to send a reply message 412, it will be understood that the recipient now becomes a sender 301, and the exemplary process of this implementation repeats (see FIG. 3). In the example illustrated by the screenshots of FIGS. 6A-6F, the recipient's options in control menu 642 as shown in screenshot 640 of FIG. 6D include saving the received message via the heart-shaped "Favorites" button 641 or sending a 3D movement data message as a reply via "Create meu" button 643.

Example 4: 3D Movement Data as Part of a Novel Social Communication Platform

Besides embodiments where a 3D movement data message is transmitted from one sender to one recipient, and besides those additional embodiments where a 3D movement data message is transmitted from one sender to multiple recipients (including a defined group or class of recipients), yet further embodiments exist where 3D movement data messages are transmitted between multiple senders and multiple recipients (including defined groups or classes thereof).

In these further embodiments, it will be readily appreciated how 3D movement data does not only form a novel medium of communication, but also forms the basis for a novel social communication platform. For example, transmission of 3D movement data messages between groups of senders and recipients permits the creation of novel 3D-enhanced social interactions, such as interactive and/or asynchronous events, games, contests, dance-offs, parties, and the like.

Such 3D-enhanced social interactions also will include group classes for yoga, movement, dance, boxing, martial arts, or other exercise, for instance where the teacher and students can share and interact with each other's physical movements and utilize novel forms of feedback, facilitating skill acquisition and training.

For example, in some embodiments, students are able to embody a dance teacher's virtual avatar and learn to dance "inside of them" to acquire their moves and techniques. Additional 3D-enhanced social interactions will include using musical instruments as part of musical instruction, facilitating learning, especially with instruments demanding a high degree of motor control, such as the drums. For instance, a student can embody a drum teacher's arms, hands, legs, and feet, and receive haptic feedback to help guide the student's movements.

Training of other skills involving difficult motor control also can be facilitated (e.g., sign language, juggling), and it will be readily appreciated how benefits directly flow from the ability to embody the 3D movements of others, and allow others to embody one's own 3D movements, especially with additional audio, visual, and haptic feedback, and more especially with additional synesthetic capabilities unique to this new form of interaction. Moreover, interaction with captured 3D movement data can involve different visualization methods, feedback types, and playback speeds, and 3D models can also be frozen in space with no movement to permit deep study and show negative space. In these and such other exemplary implementations, it will also be appreciated that such embodiments also will allow for improved learning and training when done asynchronously. Other possibilities for fitness and education, which should now be within the contemplation of an ordinary artisan, are legion.

Other suggestive examples, in the field of entertainment, include embodiment as entertainers, dancers, musicians, actors, extreme sports figures, athletes, or as novel avatars having unique affordances in an immersive social play environment such as a scavenger hunt.

Additional suggestive examples, in the field of mental health and emotional well-being, include embodiment practices that provide feedback about one's body to make oneself feel safer therein (reducing symptoms of depression, anxiety, or post-traumatic stress disorder). In some such examples, the methods and systems of the invention are advantageously used as part of PAT, to enhance and accelerate the treatment process.

Additional embodiment practices will be used to break down implicit biases or reduce discrimination (e.g., by embodying different people having different characteristics). Yet further embodiment practices will be useful for academic research, e.g., through experiments designed to measure human movement data in response to specific triggers or cues, or to study the effects of embodiment on any of the above classes of activities. For instance, research can be done to compare which visualization methods, feedback types, playback speeds, and the like have the best outcomes and lead to the fastest acquisition or greatest retention of skills (and further, such research may even be done with large sets of such data, as in Example 5 below.)

As the above exemplary implementations demonstrate, 3D-enhanced interpersonal and social interactions will be curated or designed in any number of novel ways, for any number of never-before-seen applications, and the limit resides only in the imagination of an ordinary artisan armed with knowledge of this disclosure.

While some implementations will have specific purposes or goals in mind, other implementations will be purely for entertainment, exploration, and play. For instance, in some examples, a single avatar may have different body parts (joints, limbs, etc.) that are combined and mapped to different users (e.g., one user operates the right leg, another the left leg, another the right arm, another the left arm, etc.). In such embodiments, for example, a method may comprise the steps of: capturing 3D human movement input from at least one sender; creating a (combined) 3D movement data package from the (aggregate) 3D human movement input of the at least one sender (by use of any of numerous means of combining, amalgamating, aggregating, and/or averaging such input as will be known to those in the art); sending the (combined) 3D movement data package to a recipient device; and rendering a (combined) 3D movement object on the recipient device, from the (combined) 3D movement data package.

In some embodiments, 3D movement data will be combined from any number of multiple users, to create an amalgam of a shared movement. In such embodiments, for example, a method may comprise the steps of: capturing 3D human movement input from at least one sender; creating an (amalgamated) 3D movement data package from the (aggregate) 3D human movement input of the at least one sender (by use of any of numerous means of combining, amalgamating, aggregating, and/or averaging such input as will be known to those in the art); sending the (amalgamated) 3D movement data package to a recipient device; and rendering an (amalgamated) 3D movement object on the recipient device, from the (amalgamated) 3D movement data package.

In other examples, a single avatar may have the movement of each of its joints be rendered by taking the mathematical average of a set of users' joints (e.g., a group of friends waves or dances, and the movement is the average of all of their movements). In such embodiments, for example, a method may comprise the steps of: capturing 3D human movement input from at least one sender; creating an (average) 3D movement data package from the (aggregate) 3D human movement input of the at least one sender (by use of any of numerous means of combining, amalgamating, aggregating, and/or averaging such input as will be known to those in the art); sending the (average) 3D movement data package to a recipient device; and rendering an (average) 3D movement object on the recipient device, from the (average) 3D movement data package.

Accordingly, in these exemplary implementations, one or more 3D objects rendered on the recipient device is a combined 3D movement object, an amalgamated 3D movement object, or an average 3D movement object, said 3D movement object based on the captured 3D human movement input from the sender and the at least one additional sender Moreover, even apart from the benefits of such novel forms of interaction to learning and mental well-being, simply increasing daily activity and caloric output by sending 3D movement data messages that utilize the entire body will have significant benefits on human health (indeed, it has been estimated that sending or receiving ten 3D movement data messages burns 50 calories more than the same number of regular social network messages).

Example 5: Use of 3D Movement Data by Other Systems and Processes

Besides using 3D movement data as a novel means of communication between individuals and groups, and as a novel social communication platform, as described above, 3D movement data also can be aggregated, indexed, compressed, stored, and extractable and retrievable for use in other systems and processes. No other system known to the inventors provides cloud storage for indexing and querying 3D human movement data captured from consumer VR motion capture devices or mobile phone cameras.

In some embodiments, stored 3D movement data is used to train machine learning models (in preferred embodiments, only with explicit user consent). Machine learning is an application of AI that provides systems the ability to automatically learn and improve from experience without being explicitly programmed, for instance in applications where it is difficult or infeasible to develop conventional algorithms to perform needed tasks. Machine learning algorithms build a mathematical model based on sample data, known as "training data." Stored 3D movement data provides novel and valuable training data for machine learning applications.

Such data, for example, will be used to train AI to understand human body language, so that computers can better understand and respond to human emotion and intention. For instance, correlations between 3D movement data and user choice of emotional avatars, filters, and other parameters will be utilized to train machine learning models to classify human emotions (i.e., sentiment analysis). Such data will also be used to develop novel models to improve health tracking, early disease detection, and other medical uses, and to improve computer vision.

For example, in some embodiments, 3D movement data is used to enhance and accelerate the treatment process in PAT, and/or to enable such PAT to be scaled up and brought to larger groups of patients with fewer therapists (and applicable to both individual and group therapy), reduced demands on therapist time, and/or other efficiencies as will be appreciated.

Other contemplated uses for which large sets of 3D human movement data will have novel and significant applications include computational statistics, data mining and "knowledge discovery in databases" (KDD), predictive analytics, user behavior analytics, and generally such applications within computer science, statistics, and data analytics that have the overall goal of using large and complex data sets and intelligent methods to extract information.

It will be readily understood and appreciated that the concepts, methods, and systems of the examples and embodiments herein may be implemented in numerous ways, with reference only to the teachings of the present disclosure and the general knowledge of the art. In an exemplary implementation, specific movement data channels can be built into an API to allow easy use and widespread adoption. In such an implementation, the API provides and defines a set of functions and procedures (e.g., defines the kinds of calls or requests that can be made, how to make them, the data formats that should be used, the conventions to follow, etc.) to allow the creation of other applications that access the features and data described in this disclosure.

Figure 5:
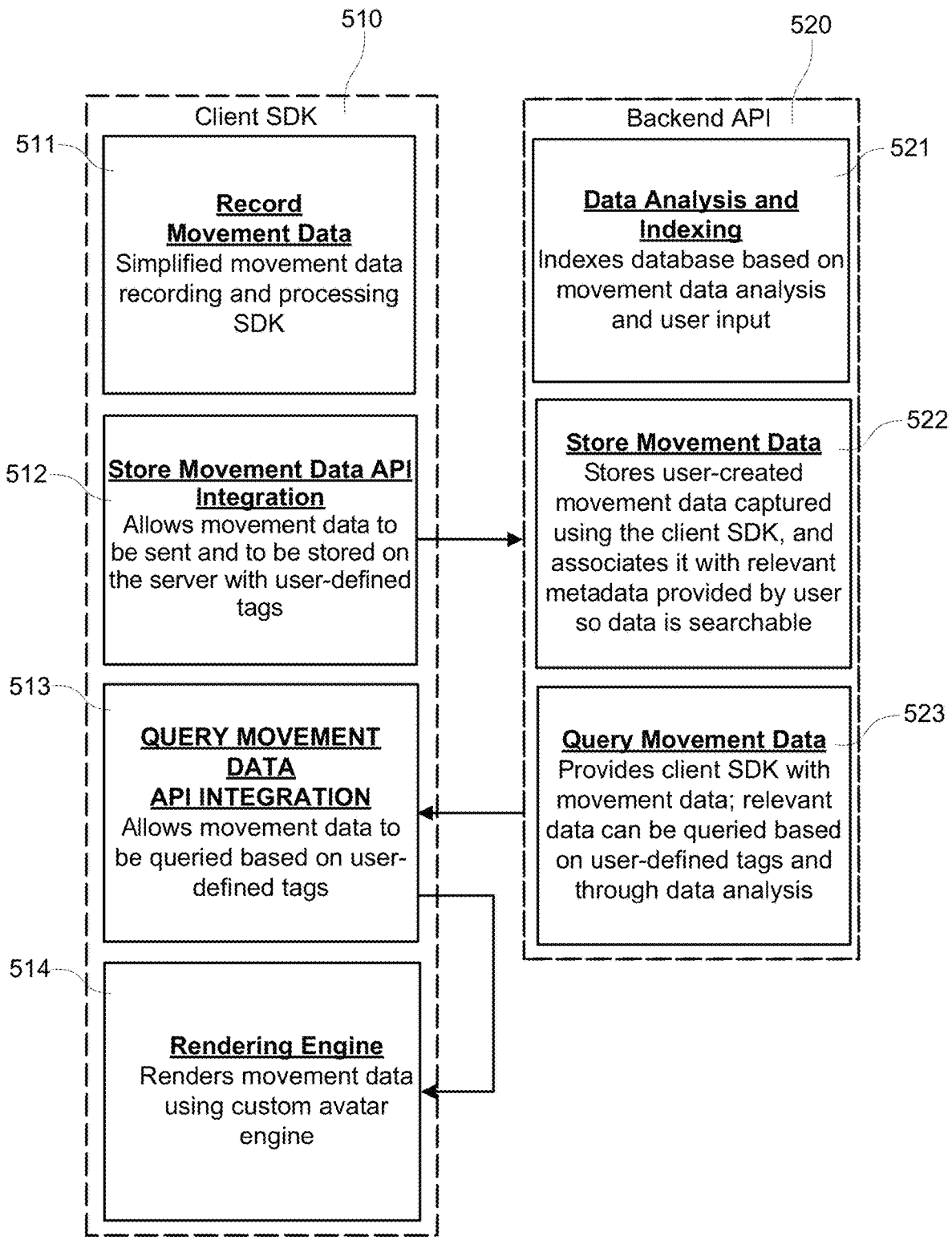
FIG. 5 is a block diagram illustrating an exemplary computing architecture comprising a backend application programming interface (API) and a client software development kit (SDK), illustrating some embodiments in which novel applications can store, query, access, and utilize the 3D human movement data described herein.

One such exemplary computing architecture (comprising a backend API and a client SDK), and the interactions between the multiple software intermediaries therein, is shown by the block diagram in FIG. 5. Specifically, Client SDK 510 comprises a simplified movement data recording and processing SDK Record Movement Data 511, Store Movement API Integration 512 which allows movement data to be sent and to be stored on the server with user-defined tags, Query Movement Data API Integration 513 which allows movement data to be queried based on user-defined tags, and Rendering Engine 514 which renders the movement data using a custom avatar engine. Backend API 520 comprises Data Analyzing and Indexing 521 which indexes a database based on movement data analysis and user input; Store Movement Data 522 which stores user-created movement data captured using Client Data SDK 510, and associates it with relevant metadata provided by the user so the data is searchable; and Query Movement Data 523 which provides Client SDK 510 with movement data whereby relevant data can be queried based on user-defined tags and through data analysis.

In some embodiments, 3D movement data is used to improve patient safety during mental health therapies, such as PAT. For example, in some embodiments, 3D movement data is used to detect a safety issue, such as inappropriate physical contact between the therapist and the patient. In some embodiments, subsequent to detecting a safety issue by 3D movement data, a safety alert (such as a message or other means of communication) is triggered to alert a third party to the occurrence of the safety issue.

Example 6: Communication of 3D Movement Data with Interactive Effects and Games

FIGS. 7A-7D are diagrams illustrating an exemplary implementation of the invention, in which there is video of a woman leaping for joy from which 3D human movement data is captured, the human shape is separated from ambient background, and the joints and skeletal frame of the human form are identified and stored as part of the 3D human movement data, and the 3D human movement data is combined with the segmented human form to be played back in augmented reality (AR) space at the receiving end, along with 3D interactive effects, in accordance with an embodiment of the invention. In some such embodiments, a "hologram" effect may be created.

Figure 11A:
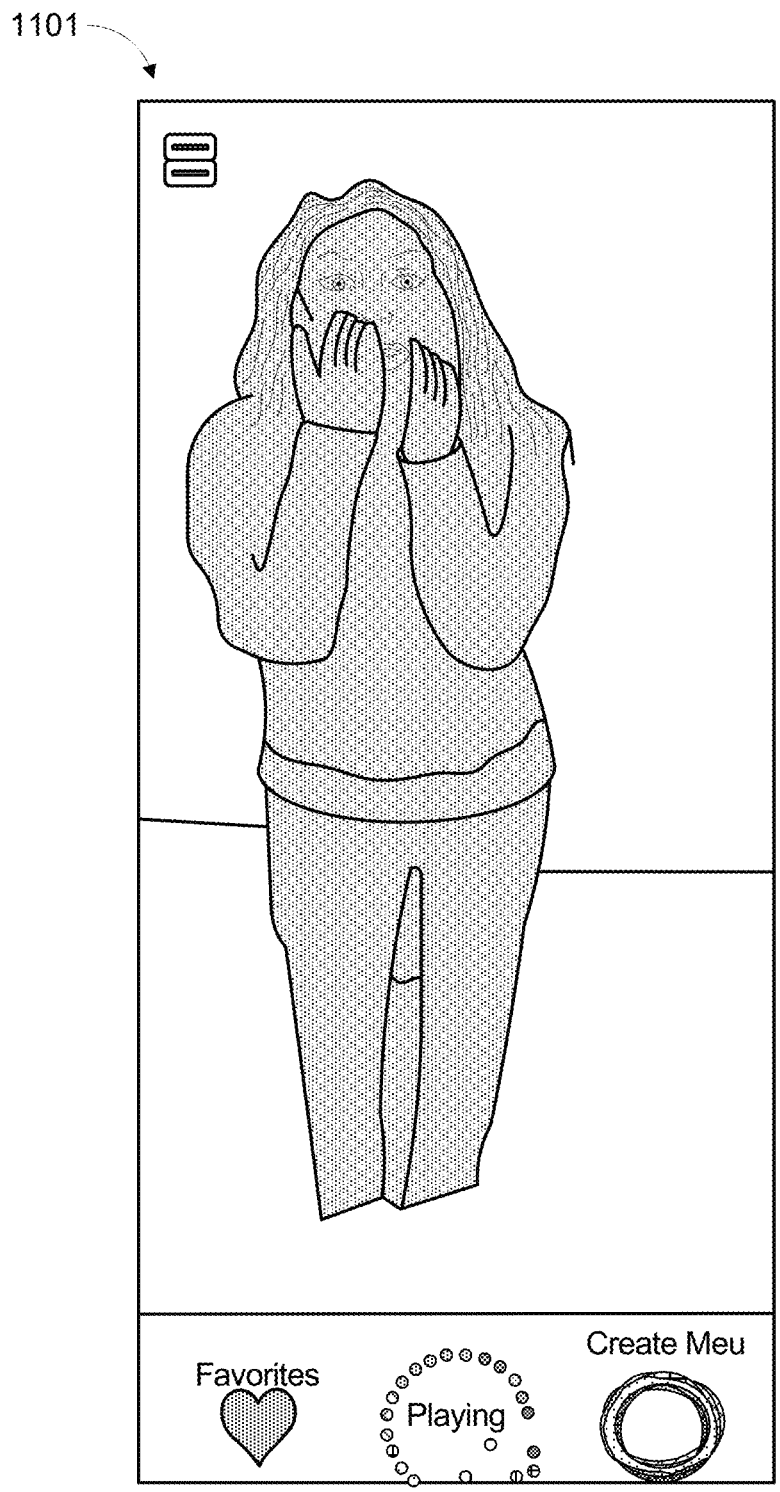
FIGS. 11A-11C are diagrams illustrating representations of screenshots demonstrating exemplary implementations wherein a recorded human form can appear to be present (e.g., as a "hologram") in a real environment, as discussed in Example 6, in accordance with embodiments of the invention.
Figure 11B:
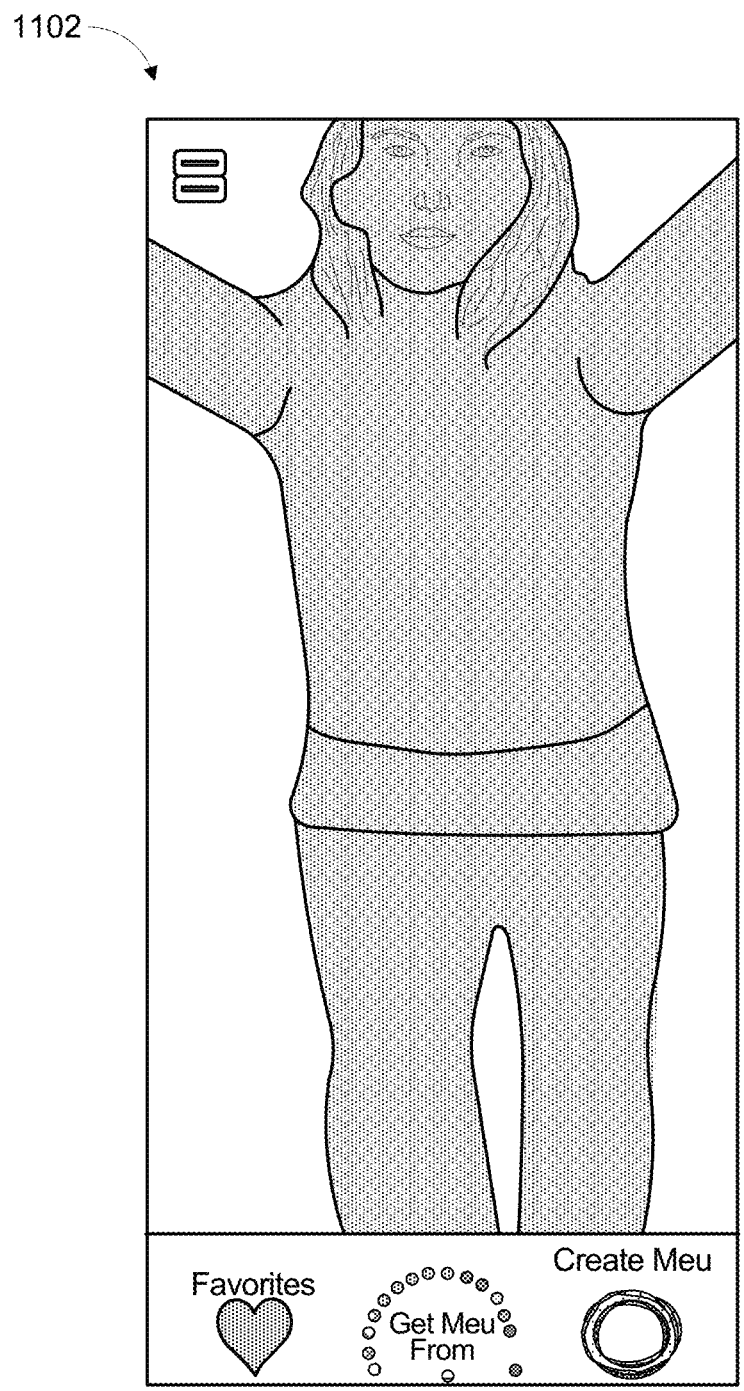
Figure 11C:
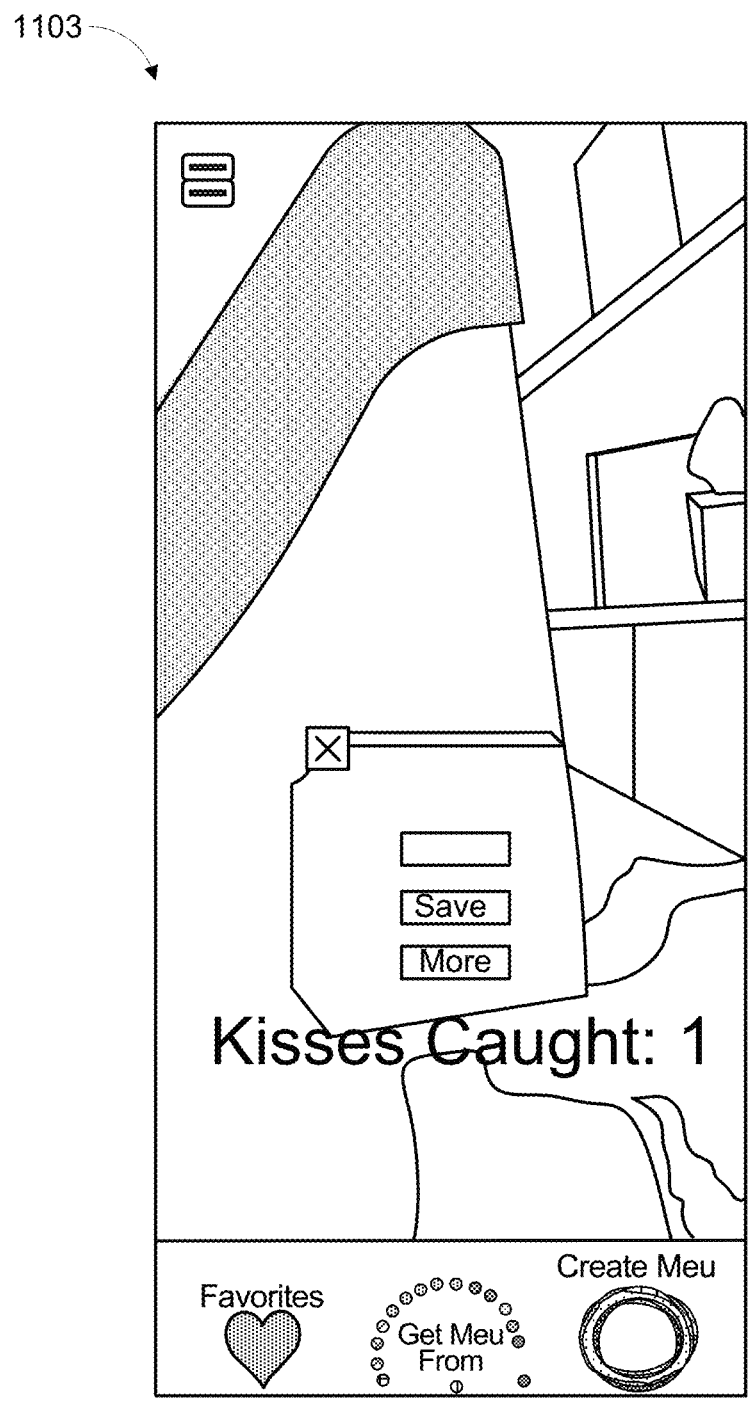

For example, and as demonstrated in FIGS. 11A-11C, the recorded human form can be played back in a "mixed reality" environment where the recording is, e.g., rendered over a live capture of the real environment (for instance, using the back camera of a smartphone). Using such means, a recorded human form can appear to be present (e.g., as a hologram) in a real environment. In the example of FIGS. 11A-11C, demonstrating using screenshot representations 1101-1103, the sender blows kisses to the recipient, and the recipient may catch those kisses (see 1103 "Kisses Caught: 1"), as similarly described above in Example 3.

Figure 7B:
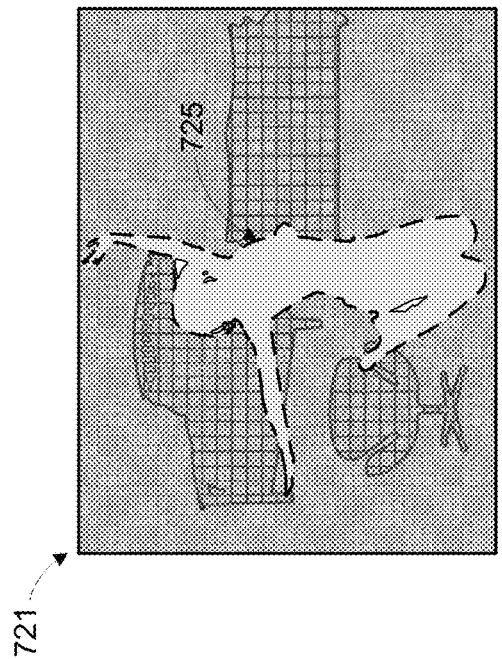
FIGS. 7A-7D are diagrams illustrating an exemplary implementation of the invention, i.e., Example 6, in which 3D human movement data is captured, the human shape is segmented/separated from the background, the joints of the human form are identified, and then the 3D human movement data (including the identified joints) is combined with the segmented human form to be played back in augmented reality (AR) space at the receiving end, with 3D interactive effects and optionally games in accordance with an embodiment of the invention.
Figure 7D:
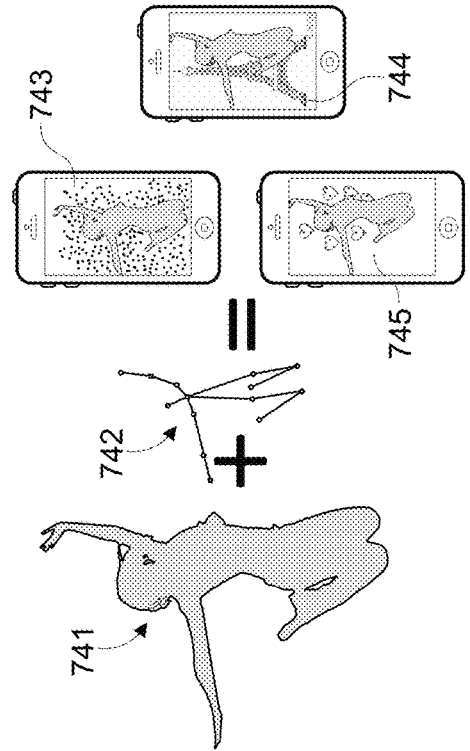
Figure 7A:
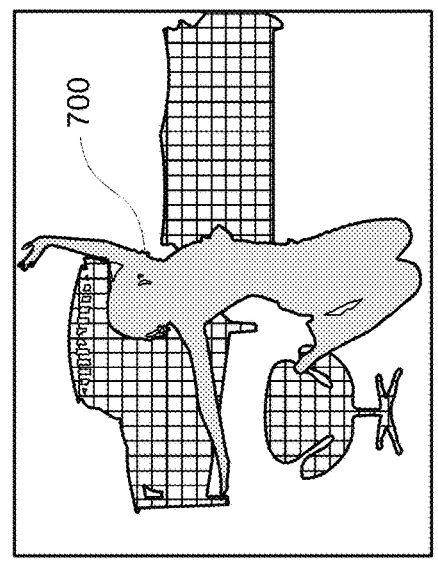
Figure 7C:
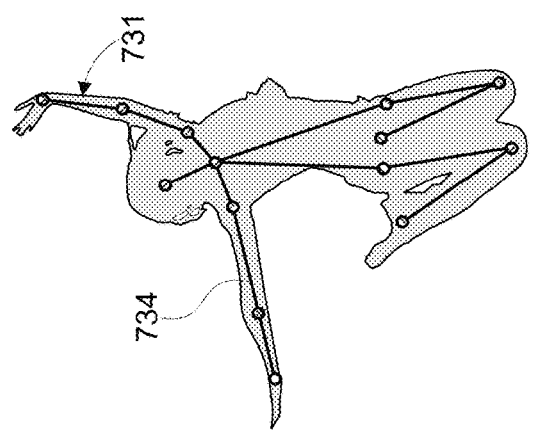

In FIG. 7A, there is video input of a woman 700 jumping for joy in a room with furniture, which may include soft furniture, and including a bed, a couch, and a chair as examples. FIGS. 7B and 7C illustrate the capture of 3D human movement data. Specifically, in FIG. 7B, the human form/shape 725 is segmented/isolated and separated from background 721, while in FIG. 7C, the joint positions, as indicated by exemplary joint 731, and the rotations thereof, are captured over time from the video of woman 700 jumping for joy, thereby providing movement data in regard to skeleton model/frame 734.

On the receiving side (or, equivalently, when playing back), the segmented human form/shape 741 and the joint positions/rotations 742 are used to create a 3D human movement object, as shown in FIG. 7D. Various 3D interactive effects and games may be used in accordance with embodiments of the invention. Three different examples of this are shown in FIG. 7D, in relation to a smartphone screen. In 743, the 3D movement object is reproduced with glitter/particles moving in relation to the 3D movement object; in 744, the 3D movement object is reproduced with a background image of the Eiffel Tower; and, in 745, the 3D movement object is reproduced with hearts (which may optionally be moving and changing shape) in relation to the 3D movement object.

Example 7: 3D Movement Data and VR Environment and Avatar Features

In general, FIGS. 8, 9A-9B, and 10A-10B illustrate exemplary implementations of user interfaces (UIs) in VR/AR environments in accordance with embodiments of the invention.

Figure 8:
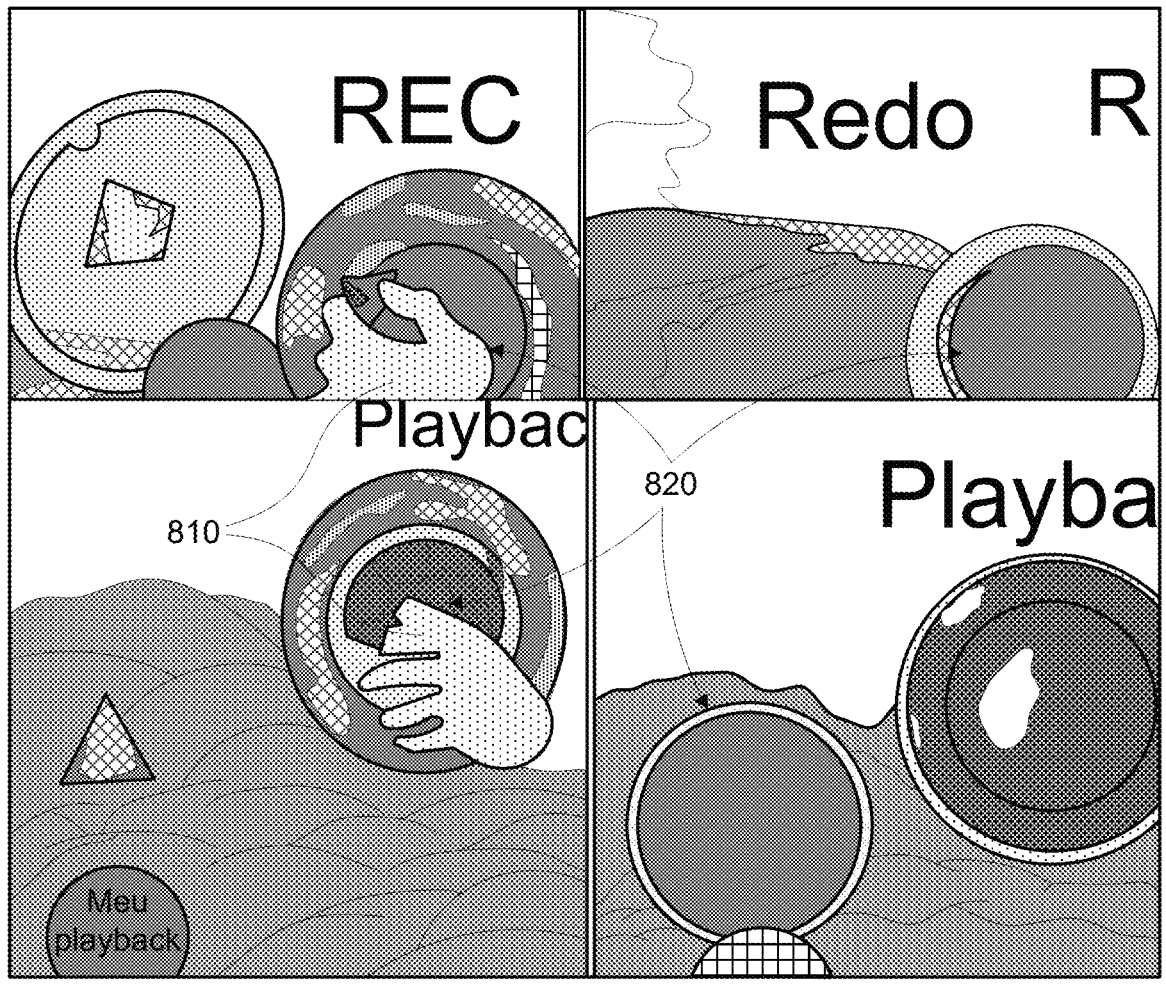
FIG. 8 is a diagram illustrating four representations of screenshots demonstrating exemplary implementations of a "meme" ball UI being used to control various functions of a 3D movement data system, as discussed in Example 7, in accordance with an embodiment of the invention.

FIG. 8 illustrates four exemplary implementations of a "meme" ball UI being used to control various functions of a 3D movement data system in accordance with an embodiment of the invention without the need for controller button (or like) input. In this embodiment, the user's hand avatar 810 can manipulate a "meme" ball 820 in the VR environment in order to control various functions, such as recording, playback, sending/transmitting, and other like actions. In the top left of FIG. 8, hand avatar 810 is moving "meme" ball 820 to the proper receptacle/hole within the VR environment in order to initiate recording of a new Meu ("REC"). In the top right of FIG. 8, hand avatar 810 has moved "meme" ball 820 into the proper receptacle/hole within the VR environment in order to redo the recording of the Meu ("Redo R"). In the bottom of FIG. 8 (left and right-hand sides), hand avatar 810 is moving "meme" ball 820 to the proper receptacle/hole within the VR environment in order to initiate playback of a Meu ("Playback").

Figure 9A:
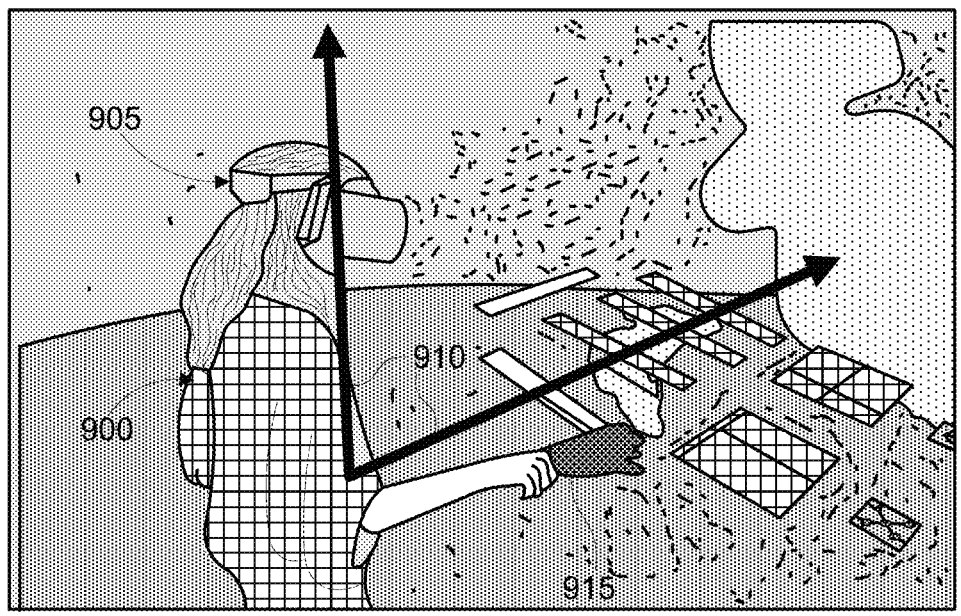
FIGS. 9A-9B are diagrams illustrating representations of screenshots demonstrating exemplary implementations of VR environment/avatar features for a user, as discussed in Example 7, in accordance with an embodiment of the invention.
Figure 9B:
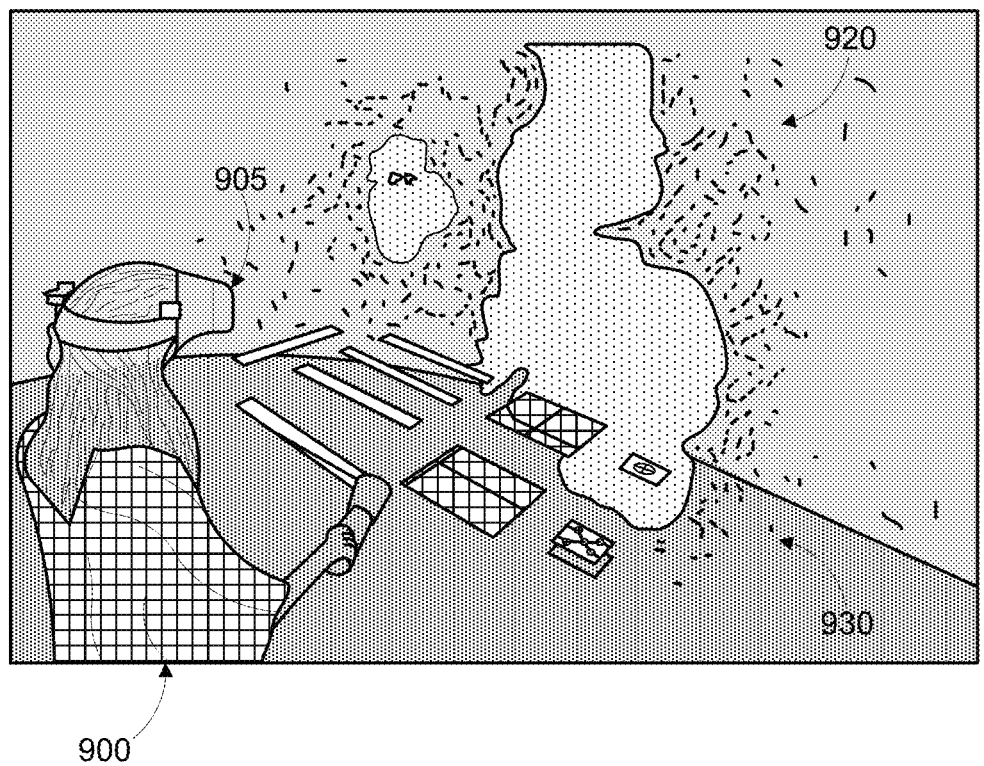

FIGS. 9A and 9B illustrate avatar and VR environment features being used by user 900 wearing VR headset 905 and seeing the VR environmental features as indicated. FIG. 9A illustrates how the VR environment according to an embodiment of the invention adapts to the user's height (and optionally other body characteristics), thereby encouraging user 900 to stretch and otherwise move their body, as illustrated by arrows 910. Moreover, the VR environment according to this embodiment of the invention requires user 900 to move in order to implement certain commands, such as sending a message, which requires user 900 to extend their hand, as indicated by movement 915 in FIG. 9A.

FIG. 9B indicates how user 900 may change avatar features, as well as games and other settings, in the VR environment according to an embodiment of the invention. In FIG. 9B, the actual body of the user 900 wearing the VR headset 905 is shown on the left-hand side of the drawing, while a mirror representation/avatar 920 of user 900 as they appear in the VR environment is shown on the right-hand side along with the manipulatable UI objects 930, including a slider UI, whereby controller button input is not needed.

Figure 10A:
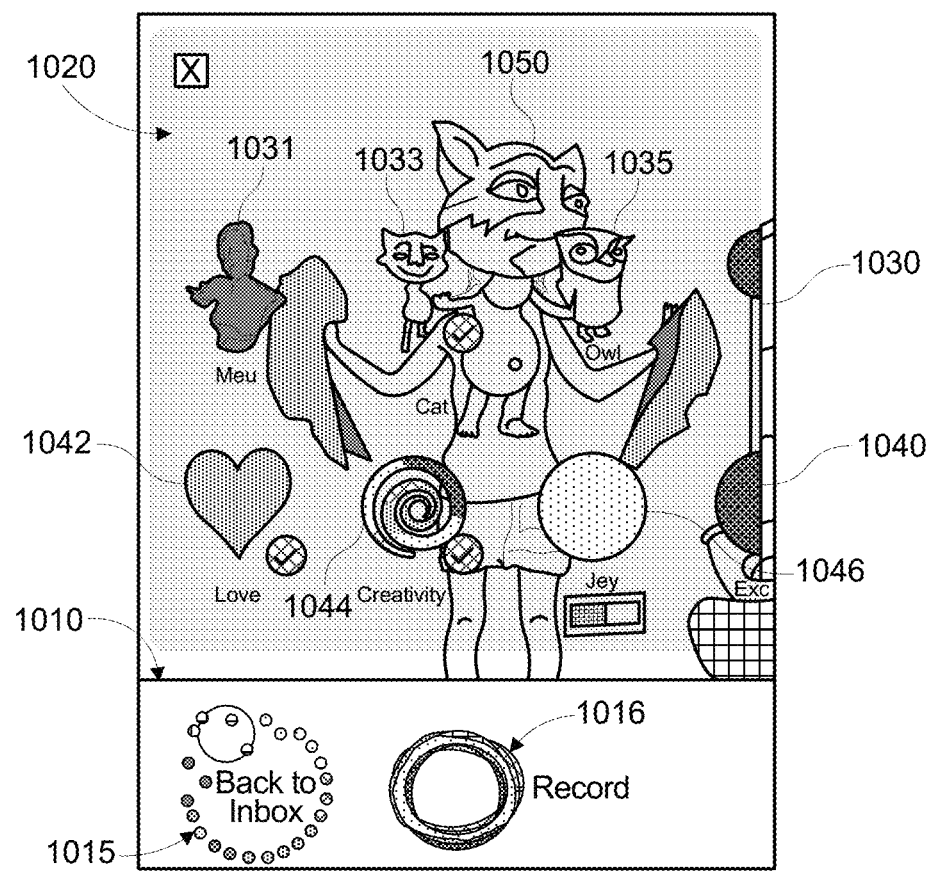
FIGS. 10A-10B are diagrams illustrating representations of screenshots demonstrating exemplary implementations of UIs for selecting avatar, games, and other like features/settings, as discussed in Example 7, in accordance with embodiments of the invention.
Figure 10B:
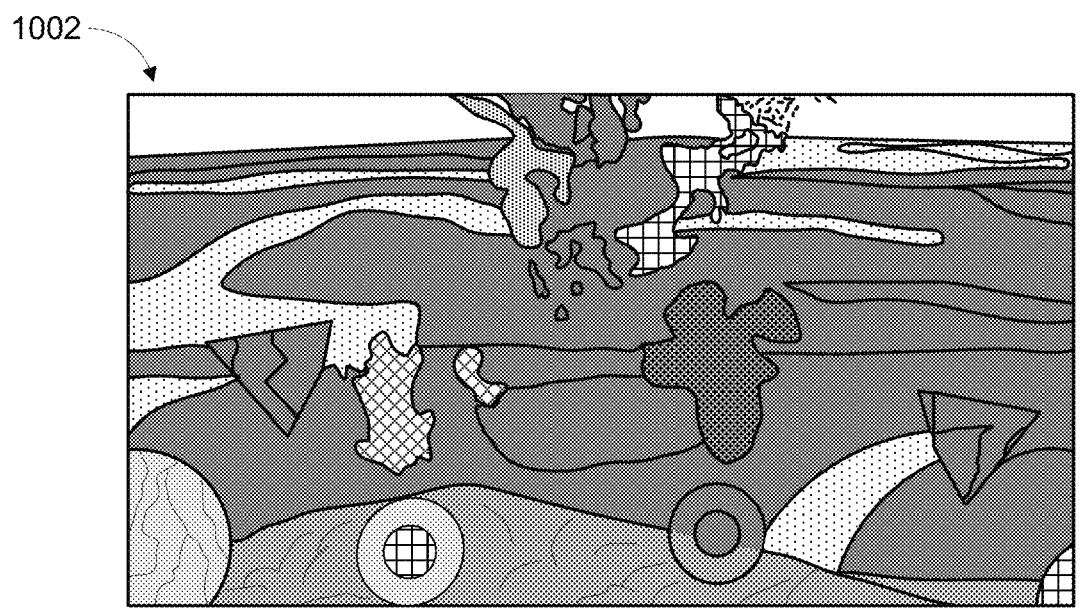

FIGS. 10A and 10B illustrate exemplary implementations of UIs for selecting game and avatar features/settings in a 3D movement data system in accordance with some embodiments.

FIG. 10A is a representation of a screenshot 1001 from an iOS device, illustrating a UI by which a user may choose an emotion and get a game designed around that emotion according to an embodiment of the invention. Screenshot 1001 shows control menu 1010 (similar in certain aspects to control menus 614 and 642 in FIGS. 6A-6F) having control buttons 1015 ("Back To Inbox") and 1016 ("Record"), as well as see-through selection menu 1020 superimposed on top of the underlying image/video, featuring a top row 1030 of avatar/image choices and a bottom row 1040 of emotion choices. More specifically, the avatar/image choice row 1030 has choices of avatars/images for the user to select from, including a user 3D movement data avatar ("Meu") 1031 in accordance with the invention, a cat image 1033, an owl image 1035, etc., continuing out of the screen to the right where further avatar/images may be scrolled to and selected, while emotion choice row 1040 has choices of emotions for the user to select from, including Love 1042, Creativity 1044, Joy 1046, etc., continuing out of the screen to the right where further emotion choices may be scrolled to and selected.

In the emotion choice row 1040 of selection menu 1020, Love 1042 and Creativity 1044 have been selected by the user, as indicated by the checkmark in a circle to their lower right-hand side. Thus, the game to be generated (or any other activity/function to be generated) will be designed around the user-selected emotions of Love 1042 and Creativity 1044. Similarly, in the avatar/image choice row 1030 of selection menu 1020, the cat avatar/image 1033 has been selected by the user, as indicated by the checkmark in a circle to its lower right-hand side. Thus, as also shown in screenshot 1001, cat avatar/image 1050 is seen superimposed over the human subject in the image/video, mimicking the arms-spread gesture being made by the human subject.

FIG. 10B illustrates a VR environment 1002 in which an AR UI may be used to select and control various settings/features for, e.g., avatar/images and games, in a manner similar to that shown in FIG. 8, according to an embodiment of the invention. Like the exemplary implementation of the UI in FIG. 8, the user may use and manipulate "meme" ball and other images/holograms in VR environment 1002 to scroll through, select, edit, and otherwise change avatar images/holograms (similarly to the choosing of avatar/images on the mobile phone screen of FIG. 10A) and game attributes (similar to the manipulation/control of avatar features, as well as games and other settings, in the VR environments of FIGS. 8 and 9A-9B).

In an embodiment of the invention, a user records 3D movement data to be played back for, e.g., family and friends, after the user's death. In one embodiment, the 3D movement data is such that the 3D message, representation, and/or hologram is interactive, i.e., programmed to provide responsive communication to each of the family and friends. In some embodiments, the 3D message, representation, and/or hologram will be uniquely tailored to each recipient and/or uniquely tailored to other characteristics such as time, date or location.

Example 8: Use of 3D Movement Data in Psychedelic-Assisted Therapy

In some embodiments, as in the exemplary embodiments of Example 8, are implementations in the field of psychedelic-assisted therapy (PAT), which includes and is also sometimes referred to as psychedelic-assisted psychotherapy (PAP).

Psychedelic-assisted therapy, broadly, includes a range of related approaches that involve at least one session where one or more patients (interchangeably, "subject" or "client," and it will be understood that a "patient" need not be diagnosable or diagnosed with any disorder, and will include individuals seeking therapy or psychotherapy (e.g., for mental health disorders or the improvement of mental health conditions or general mental health) as well as individuals seeking psychedelic experiences for individual betterment or general improvement of mental health, or simply for experiential value or "fun") is administered a psychedelic and is monitored, supported, and/or otherwise engaged by one or more trained facilitators or mental health professionals while under the effects of the psychedelic (see, e.g., Schenberg E. E., Psychedelic-Assisted Psychotherapy: A Paradigm Shift in Psychiatric Research and Development. Frontiers Pharmacol., 9, 733, 2018; Tullis, P. (Jan. 28, 2021). The Rise of Psychedelic Psychiatry, Nature, vol. 598, pp. 506-509; Olson D. E. (2021). The Promise of Psychedelic Science. ACS Pharmacol. Trans. Sci., 4(2), 413-415). Herein, reference to "psychedelic-assisted therapy" or "PAT" will be understood to broadly include all such modalities and experiences generally (e.g., any of drug-assisted therapy or psychotherapy, administration of a psychedelic together with psychological support, administration of a psychedelic together with supervision or monitoring, guided or facilitated psychedelic use, and the like), unless an intent to refer to a specific type of therapy or use is clear from the context.

Protocols have been developed for the standardization of procedures to be used with PAT, such as the provision of psychological support. See, e.g., Johnson, M.; Richards, W.; and Griffiths, R., Human hallucinogen research: guidelines for safety, J. Psychopharmacol. 22, 603-620 (2008); and Mithoefer, M.; Mithoefer, A.; Jerome, L.; Ruse, J.; Doblin, R.; Gibson, E.; Ot'alora M., A MANUAL FOR MDMA-ASSISTED PSYCHOTHERAPY IN THE TREATMENT OF POSTTRAUMATIC STRESS DISORDER (2015), published by the Multidisciplinary Association for Psychedelic Studies (MAPS); Guss, J., Krause, R., & Sloshower, J. (Aug. 13, 2020). The Yale Manual for Psilocybin-Assisted Therapy of Depression (using Acceptance and Commitment Therapy as a Therapeutic Frame); Tai, S. J., Nielson, E. M., Lennard-Jones, M., Johanna Ajantaival, R. L., Winzer, R., Richards, W. A., Reinholdt, F., Richards, B. D., Gasser, P., & Malievskaia, E. (2021). Development and Evaluation of a Therapist Training Program for Psilocybin Therapy for Treatment-Resistant Depression in Clinical Research. Frontiers in psychiatry, 12, 586682. However, it will be readily appreciated that such protocols and procedures are merely exemplary of the types that may be utilized, and PAT may or may not involve one or more psychotherapeutic modalities, and also may or may not involve any specific form of psychological support; for example, esketamine (Spravato®, Janssen/Johnson & Johnson) is typically administered according to a Risk Evaluation and Mitigation Strategy (REMS) that only requires the observation and monitoring of the patient by a healthcare provider, without any psychotherapeutic intervention.

Typically, PAT comprises one or more psychedelic dosing (drug administration) session(s), one or more preparation sessions before the one or more psychedelic dosing session(s), and one or more integration sessions after the psychedelic dosing session(s). Optionally, there may be an initial screening session to determine the patient's suitability for PAT, as well as one or more sessions to provide a regimen of after-care and/or relapse management after the integration session(s) (whether either type of session is necessary depends on the mental health condition being treated, the outcome(s) of the dosing and other sessions, etc., as would be understood by one of ordinary skill in the art). It will be readily appreciated that the number and relative timing and order of the sessions will be chosen based on the therapeutic goal(s), the protocol(s) or clinical manual(s) followed, the psychedelic(s) used, the characteristics of the patient(s) and the disorder(s) to be treated (or improvements in mental health sought), and such other characteristics as will be readily appreciated by those of ordinary skill in the art.

In implementations directed to PAT and related therapies (i.e., which may not include the administration of a psychedelic), the methods and systems for communication using 3D human movement data according to embodiments of the invention may be used to provide psychotherapy, therapy, psychological support, observation or monitoring, or the like, to patients during one or more of the screening session(s), preparation session(s), psychedelic dosing session(s) if applicable, integration session(s), and/or after-care/relapse management session(s).

Disclosed methods and systems using 3D human movement data moreover may be used to provide a patient with a consistent, controlled, and calm environment during sessions, such as PAT dosing sessions, and/or to customize and optimize a PAT or related therapy experience.

In implementations directed to PAT and related therapies, the methods and systems for communication using 3D human movement data according to embodiments of the invention may be used to provide remote connections and interactions between the therapists (or facilitators, "guides," clinical psychologists, psychiatrists, other trained medical professionals, and the like) monitoring/overseeing the PAT or related therapy and the patient(s) of that PAT or related therapy, and/or between and among the patients themselves.

As one example of monitoring/overseeing the PAT or related therapy, 3D movement data can be used to improve patient safety. In some embodiments, 3D movement data is used to improve patient safety by detecting a safety issue during a therapy session, such as inappropriate touching of the patient by the provider of therapy. In some embodiments, 3D movement data is used to improve patient safety by detecting a safety issue during a therapy session, then triggering a safety alert, such as a message that is transmitted to a third party to alert said third party of an ongoing safety issue.

In another example, in one embodiment, a group of (i.e., two or more) patients will interact between and among themselves during a PAT session by, e.g., sharing gestures and/or performing physical exercises as a group, according to the teachings herein.

In one embodiment, a therapist overseeing a PAT dosing session will remotely "attend" the PAT dosing session with the patient, and will through sending or sharing 3D movement data provide psychological support. This advance over the art will reduce the need for specially trained therapists who can provide high-quality care to patients as part of PAT, and/or reduce the burden on individual such therapists.

For example, in some embodiments a single therapist will provide psychological support or other care to multiple patients across space and/or time. In some such embodiments, a single therapist will provide care to multiple patients who are "separate" from one another (i.e., who are unaware of the presence of each other, as if a single therapist is in the "rooms" of multiple patients all at the same time).

In other such embodiments, a single therapist will provide care to multiple patients who are "together," for example in a group preparation session, group drug-administration session, or group integration session (i.e., if all such patients are together in a single "room" or other virtual space or location). "Together" will be understood to mean that the patients are aware of the presence of each other (e.g., are able to see and optionally interact with each other's avatars) not necessarily that all are in the same room or location in physical space, or even necessarily that all are together during the same time, as some patients' presences may in certain embodiments be pre-recorded (e.g., as stored 3D movement data).

In some embodiments, different 3D movement data of a therapist will be recorded and saved, e.g., to permanent storage. The pre-recorded 3D movement data of a therapist will thereafter be available to be used with one or more patients (e.g., used non-contemporaneously or asynchronously), and will be so used, minimizing or eliminating the need for the therapist to interact with the patient(s) at one or more times during PAT.

In one exemplary embodiment, a patient undergoing PAT may experience anxiety-provoking perceptual changes or physical sensations. It is believed that the practice of reassuring physical contact or therapeutic touch such as "arm holding" by a therapist may reduce anxiety in some such situations (if a patient consents to such contact or touch; further disclosure helping to ensure such consent is below). Arm-holding is where, upon a patient's request, the therapist will place a hand on the patient's wrist, arm, hand, or shoulder, as a way of helping the patient feel more secure during PAT. This may occur, e.g., during a preparation or psychological support session, during a drug administration session, or during an integration session.

Accordingly, in some embodiments, a therapist may send 3D movement data that is received by the patient as the therapist holding the hand, arm, or shoulder of the patient. Haptic feedback is provided in some embodiments, for instance vibrations may be activated when the therapist touches a patient's avatar, communicating to the patient the sensation of physical presence and contact, and causing the patient to experience reduced anxiety.

In embodiments where pre-recorded 3D movement data of a therapist is used with a patient, the 3D movement data of the patient can be monitored to determine when psychological support such as arm holding may be beneficial, and the pre-recorded touch can be provided to the patient's avatar at such times, effectuating psychological support, the trigger for such provision being, e.g., any predetermined trigger or cue or one based on AI, machine learning, or other like analysis of the patient's 3D movement data and/or other data, or aggregate patient 3D movement data and/or other data. For example, in some embodiments, such other data includes physiological, physiometric, and/or biometric data as disclosed herein.

In various aspects as will be appreciated from the teachings herein, a therapist can provide many different forms of reassuring physical contact with one or more patients undergoing PAT, according to the methods and systems of the invention.

In various aspects as will be appreciated from the teachings herein, a therapist can provide many different forms of psychological support involving non-verbal communication with one or more patients undergoing PAT, according to the disclosed methods and systems.

In implementations directed to PAT and related therapies, the methods and systems for communication using 3D human movement data according to embodiments of the invention may be used as part of a process to capture and store movements of patient(s) during PAT sessions in order to identify, track, and/or define characteristic movements associated with negative or difficult experiences in PAT and related therapies, such that the defined characteristic movement markers are used to predict and prevent such negative or difficult experiences. Similarly, such methods and systems may be used to identify, track, and/or define characteristic movements associated with positive or good experiences and outcomes in PAT and related therapies, and the defined characteristic movement markers are used to predict and guide patient(s) into having a positive or good experience or outcome. Moreover, such methods and systems for communication using 3D human movement data may be used to playback gestures and/or characteristic movements as a therapeutic and/or teaching aid for the patient(s) during sessions of PAT and related therapies, or for the facilitator or medical professional.

In implementations directed to PAT and related therapies, the methods and systems for communication using 3D human movement data according to embodiments of the invention may be used to provide a digital platform for administering PAT and related therapies which is scalable from individual one-on-one PAT sessions up to widespread and general usage of PAT by the general public (both as part of individual and also group therapy). For example, multiple patients can interact with the 3D movement data of a single facilitator or therapist, and/or a single facilitator or therapist can interact with the 3D movement data of multiple patients.

In some embodiments, the methods and systems of the invention will be used to prepare one or more patients for PAT, or to educate one or more patients about PAT or any aspect(s) thereof. For example, a patient can interact with one or more 3D movement objects, any of which may or may not be pre-recorded and saved to storage, to understand what a psychedelic experience or the experience of PAT is like, and to get a deeper understanding thereof. In some embodiments, for instance, a patient will interact with multiple 3D movement objects stored together in one or more saved module(s) for purposes of providing a preparatory and/or educational learning experience about PAT or psychedelic experiences generally. In some embodiments, the 3D movement data of one or more patients will be used to determine or optimize one or more aspects of their PAT or psychedelic experience, as discussed herein.

Example 9: Use of 3D Movement Data in Biomarker-Augmented Therapy

In some embodiments, as in the exemplary embodiments of Example 9, 3D movement data is used to personalize and augment mental health therapy by providing personalized diagnostic and/or therapeutic biomarkers and therapy protocols.

The collection, processing, and referencing of data to create personalized diagnostic and therapeutic biomarkers and protocol for mental-health therapy overcomes longstanding limitations in the prior art. To date, mental health analytics have suffered from a lack of objective, verifiable, data-driven standards, assessments, and tests (see, e.g., Bedi et al., Nature Partner Journals Schizophrenia, 15030, 2015 at 1; Stephan et al., Lancet Psychiatry 3, 77-83, 2016a; Stephan et al., Lancet Psychiatry 3, 84-90, 2016b at 87). Indeed, clinical psychiatric decision-making (such as diagnosis, treatment selection, and risk stratification) still relies largely on subjective evaluations and subjective observations, and often comes down to the "gut feeling" of a therapist or clinician rather than relying on scientifically-based, rigorous, and objective tools.

This lack of objective tools is particularly acute in regards to PAT, at least because these therapies are still being developed and are presently constrained by the general legal and regulatory limitations on psychedelics which, inter alia, make large-scale clinical trials difficult, if not impossible (see, e.g., Schenberg, Front. Pharmacology, v. 9, article 733, 2018). The same can be said for related therapies and including BIT, which is constrained by the inherent complexity of the disorder and its intersection with culturally informed standards of the "ideal body," making large-scale and culturally agnostic clinical trials unfeasible (see, e.g., Gaudio et al., PLoS One, 9(10), 2014; Sadibolova et al., Cortex, 111: 74-86, 2019).

Thus, for this paradigm shift to happen, PAT, BIT, and other related therapies need to be further standardized, made more accessible, based on more objective data collection, and made scalable for widespread application, with clear parameters established that are applicable to large scale populations. In this regard, there is a particular need for objective, verifiable, data-driven monitoring, measurement, assessment, and guidance regarding mental health conditions, as well as systems and methods capable of generating and testing or verifying models, standards, or frameworks in the context of mental health therapy, including PAT, BIT, and related therapies.

As described above, body language is a powerful and objectively measurable means of expressing one's mental state. Biometric and 3D body movement data is an untapped gold mine in understanding mental health and in offering a way forward towards creating objective, verifiable, and data-driven monitoring, measurement, assessment, and guidance for improving the efficacy of mental health therapeutic treatment. Recent studies have found links between gait, balance, and posture in identifying major mental illnesses such as depression, anxiety, and schizophrenia (see, e.g., Feldman et al., Austin Medical Sciences, 5(1): 1039, 2020). Indeed, patients suffering from mental disorders have been found to have a unique physical profile that corresponds to particular mental disorders. For example, schizophrenia has been found to be correlated with a slow gait and decreased stride length, anxiety disorders have been found to be correlated with balance disorders, and those suffering from depression have been found to have a slow gait and slumped posture (see, e.g., Feldman et al., Austin Med. Sci., 5(1): 1039, 2020).

Recent studies honing in on specific areas of the body, such as the upper quarter posture, have demonstrated that isolating analysis of biometric and movement data to specific body parts is similarly revealing of likelihood of depression, anxiety, and level of physical activity (see, e.g., Asadi-Melerdi et al., Int. J. School. Health, 7(1): 48-55, 2020; Canales et al., Gait & Posture, 52, 258-264, 2017). Variation in head pose features have also been found to correlate in real time to specific stressors, which can be invaluable data for effective and efficient diagnosis during patient intake (see, e.g., Giannakakis et al., Conference Paper, 2018; Alghowinem et al., Conference Paper, 2013). Specific stress conditions have been found to increase head mobility and mobility velocity, in both translational and rotational features, and are found to be especially detectable during tasks that include a patient's speech. Furthermore, flexibility, which can be measured by tilting and distance between various body parts, has been found to be correlated with depression (see, e.g., Kim et al., Gait Posture, 61:81-85, 2018). Even in the absence of other typical comorbidities (e.g., obesity) and neurological, psychiatric, or musculoskeletal disorders, recent studies have found that shoulder protraction is correlated to subjective sadness (see, e.g., Rosario et al., J. of Bodywork and Movement Therapies, 17(3): 328-31, 2013). Accordingly, biometric and 3D body movement data can be profoundly helpful in furthering diagnostic and treatment protocols for mental health disorders.

Historically, gathering large scale biometric and 3D human movement data with motion capture devices was neither technologically nor financially viable. However, the exponential growth of computing power and mobile devices have opened up new avenues for efficiently and affordably collecting such data. Android and iOS now offer virtual reality (VR) body tracking and medial-lateral (ML) pose detection software development kits for developers to create applications that can run on iOS and Android operating systems. Such software can be used to harvest biometric and human movement data to be used as inputs in devising new and effective therapy for mental health disorders that are correlated with such data.

In some embodiments, certain aspects of the invention involve: (a) gathering user data ("collected data"); (b) processing collected data ("processed data"); (c) optionally, comparing processed data with the aggregated and/or processed pooled data of other users or from other sources ("reference data"); (d) obtaining a set of individualized diagnostic and therapeutic biomarkers and protocol for the user based on the processed data and optionally reference data ("personalized diagnostic and therapeutic biomarkers and protocol"); and (e) utilizing the personalized diagnostic and therapeutic biomarkers and protocol for mental health therapy, including but not limited to PAT and related therapies such as body-image therapy (BIT) ("personalized biomarker-augmented mental health therapy").

A. Collected Data

Collected data, in certain aspects, refers to any user data gathered from an individual user. User data will be any data, including in unstructured format, that is relevant to a user's biometrics, body movement, or mental health therapy, e.g., biometric and 3D body movement data such as openness or closeness of body pose, sway, balance, rhythm, asymmetries between the left and right sides of the body, smoothness of motion, jerkiness of movement, kinetic energy in the body, reaction time, and total amount of body movement that can be used to diagnose and inform therapeutic treatment protocols in mental health therapy, including psychedelic-assisted and body-image therapies. Various embodiments for biometric and 3D body movement are described herein, and 3D human movement is further disclosed in detail in embodiments above.

Such collected data can be gathered by any means; several such means follow, others have already been described in embodiments in Examples 1-9 above, to which reference is made.

In some embodiments, collected data will comprise data from questionnaires provided to an individual user for response. Questionnaires may consist of questions related to mental health history, familial history with mental health disorders, how the individual user perceives their own body, what an individual user considers to be an "ideal body," the individual user's medical history, whether the user is currently taking any prescription or non-prescription drugs, the user's history with psychedelics, and the individual user's goals for therapy.

Other user attributes may be collected, e.g., height, weight, age, gender, location, other biographical information, personal preferences, answers to specific rating scales used in the art or new to the invention, and the like, including any attributes comprising a "digital phenotype."

One of ordinary skill in the art will appreciate that useful questionnaires and assessments may include those in use by mental health professionals (e.g., such as the Hamilton Rating Scale for Depression (HAM-D); the Mini International Neuropsychiatric Interview 5 (MINI 5) (see, e.g., Sheehan et al., J. of Clinical Psychiatry, 59 Supple. 20: 22-33, 1998); The Columbia Suicide Severity Rating Scale (C-SSRS) (see, e.g., Mundt, J C et al., J. of Clinical Psychiatry, 74(9): 887-93, 2013); the Patient Health Questionnaire (PHQ-9) (see, e.g., Kroenke et al., Journal of General Internal Medicine, v. 16(9), 2001); the Generalized Anxiety Disorder 7 (GAD-7) (see, e.g., Spitzer et al., Arch. Intern. Med., 166(10): 1092-97, 2006); etc.).

In some embodiments, collected data will comprise responses obtained from journaling, mental health diaries, or any other free-form collection of text, emojis, gifs, audio or video recordings, etc., that capture the emotional, cognitive, or behavioral expressions of a user.

In some embodiments, collected data will include biophysical readings and biometric data, such as heart rate, heart rate variability (HRV), electroencephalography (EEG), pulmonary function, respiratory rate, brain entropy, body entropy, genetic biomarkers, voice characteristics, eye tracking, pose and posture data, body sway, body balance, body rhythm, asymmetries between the left and right sides of the body, smoothness of body motion, jerkiness of body movement, kinetic energy in the body, reaction time, total amount of body movement, 3D movement data, and the like.

In some embodiments, collected data will be gathered using an electronic means, which may include any electronic tool suitable for such purposes, including desktop, laptop, and notebook computers; tablets, smartphones, and other mobile electronic devices; watches, fitness trackers, and other personal electronic devices; suitable software running thereon; and the like.

Examples of suitable electronic tools include commercially available applications (and devices running such applications) (e.g., OpenPose) and others programmed for Android and iOS operating systems, utilizing Android and iOS application programming interfaces and software development kits for virtual reality (VR) body tracking and medial-lateral (ML) pose detection, serving as a means for biometric data collection and feedback as generally depicted below.

Examples of suitable electronic devices include an Apple smartphone or tablet capable of mobile augmented reality (AR), for instance, an iOS device with an A12 chip. Such devices can capture 3D motion with body-tracking functionality in the ARKit framework on the device, which recognizes and tracks a person's movements using an iOS device's rear camera.

Another example of a suitable electronic tool is The Wisdom Truffle SuperNova, which will be appreciated alongside other similar devices to be within the scope and spirit of the invention. The Wisdom Truffle SuperNova (as made available from Red Light Holland Corp., Toronto, Ontario) is a life-sized figurine (one meter tall) equipped with artificial intelligence (AI) that understands body movements. The device creates unique interactive audio-visual experiences based on dances, stretches and more. It also supports a multiplayer mode where it finds utility in group therapy, conventions, research clinics, and the like.

As noted, it will be readily appreciated that other electronic devices, such as those that can track a user's three-dimensional body movement as well as body posture, flexibility, range of motion, and body entropy may be utilized in the practice of the methods of the invention. Such means may also contain monitors to track heart rate, HRV, blood-oxygen levels, etc. It can also be synced with other biometric data collection systems such as fitness trackers or watches to collect biometric data to be correlated with data from other data gathering means.

Figure 12:
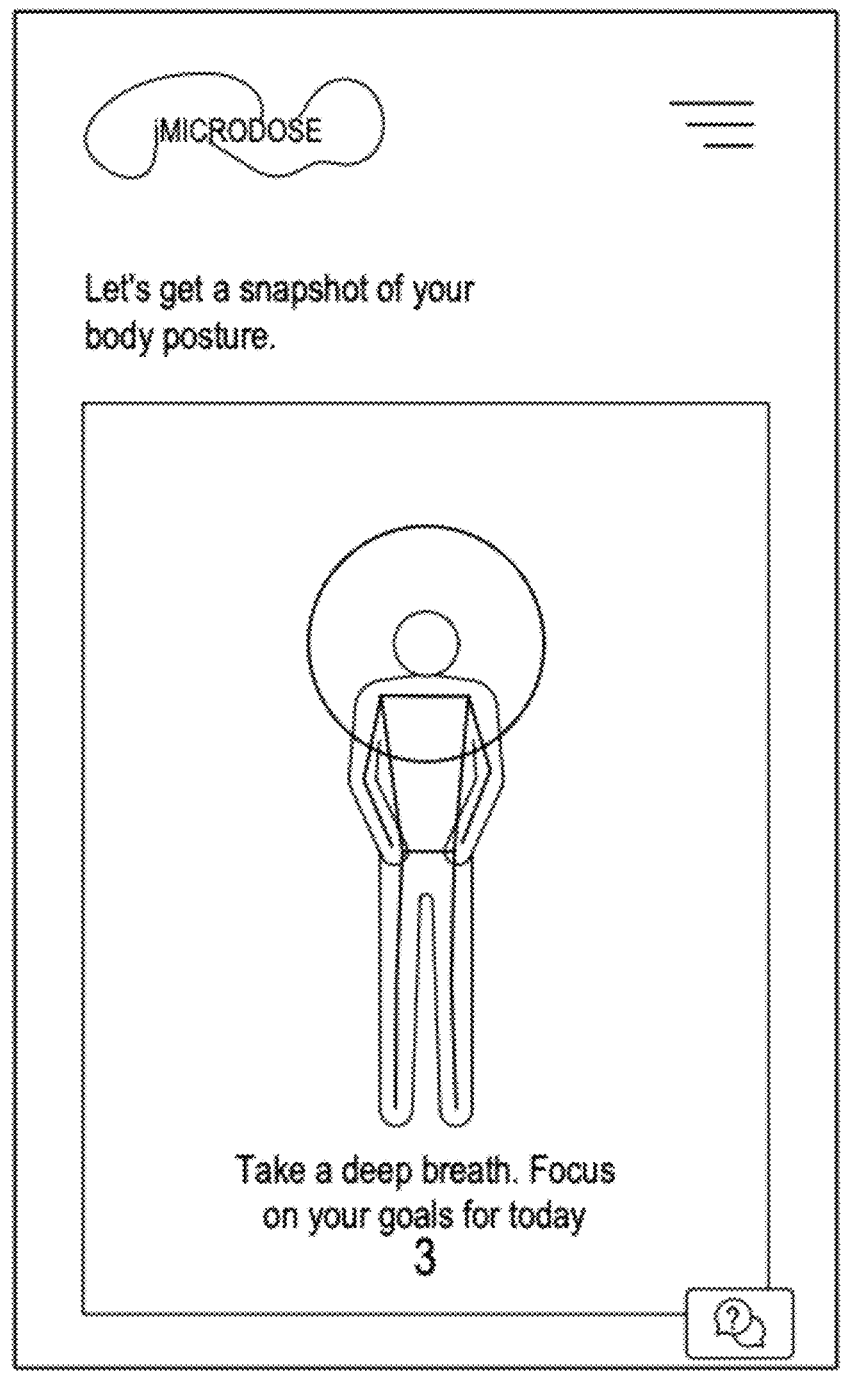
FIG. 12 illustrates an exemplary embodiment of the invention wherein body posture data is obtained.
Figure 13:
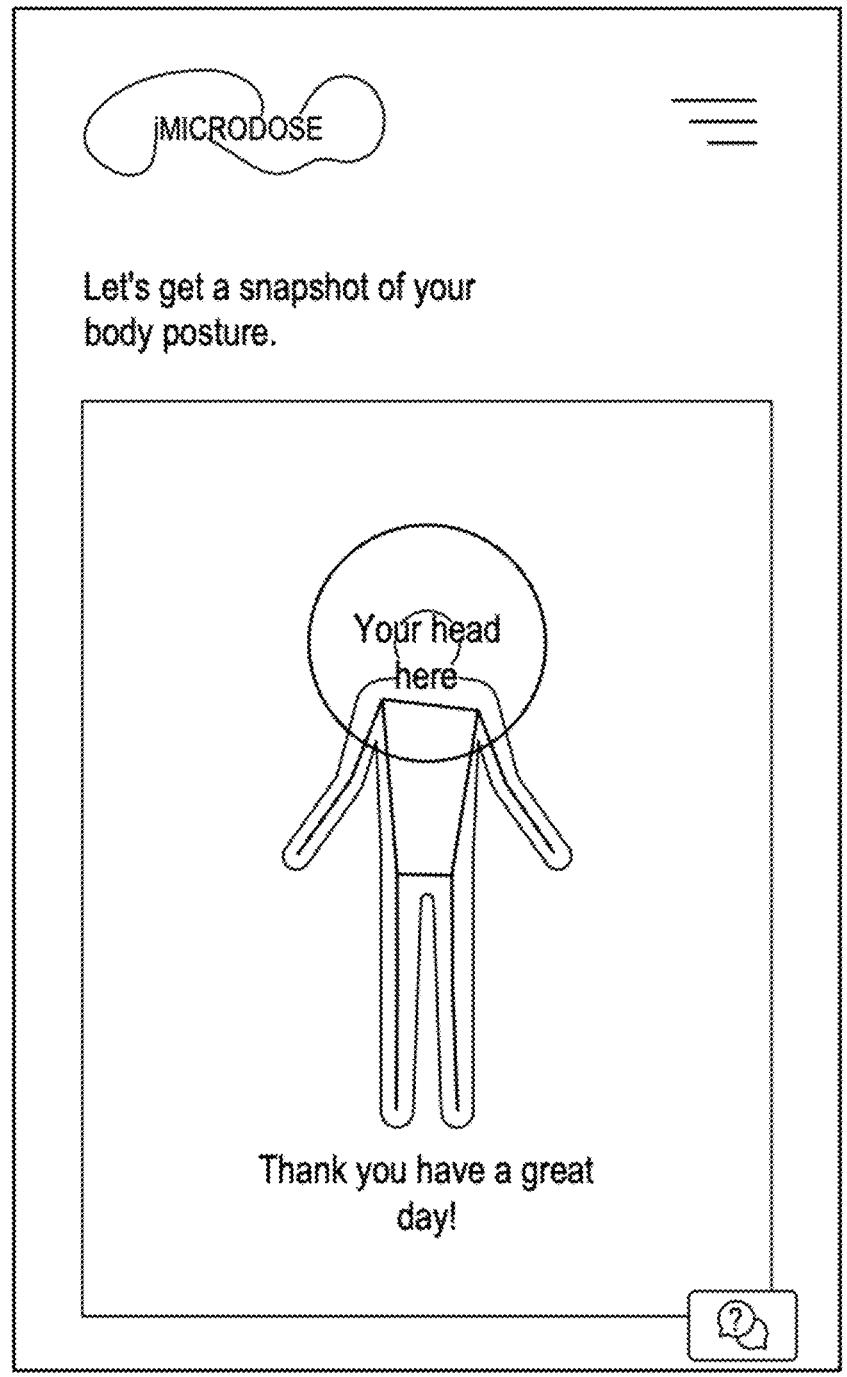
FIG. 13 illustrates an exemplary embodiment of the invention wherein an individual is instructed where to place the individual's head and body to obtain body posture data according to some embodiments of the invention.

In some embodiments, data is collected using a smartphone or web-based application, such as the iMicro app, certain exemplary depictions of which are provided in FIGS. 12-13.

As exemplified by the iMicro app, and as can be implemented using numerous other like means, an app can be used to, e.g., create a journal entry which can include data about mental health and body-image perception, answer questions about psychedelic and/or other medicinal dosing (including tracking of prescribed psychiatric medicines), answer questions about goals and emotional states for the day, take photos of body posture for data collection and analysis, and key any such data to other variables such as time and calendar date, etc.

In a preferred embodiment, photogrammetric analysis can be undertaken to calculate and collect body movement data, including body alignment and flexibility of certain body parts, by calculating the posture, tilt, and distance between different body parts. A study performed by Asadi-Melerdi et al., Int. J. School. Health., 7(1): 48-55, 2020 used photogrammetric analysis to measure back posture, head tilt, and shoulder posture. Users of the iMicro app can be photographed and analyzed for body posture in the same way undertaken by the Asadi-Melerdi et al. study, as can users of other photography applications. See FIG. 1 from the Asadi-Melerdi study as an illustration of how such photogrammetric data can be collected.

A variety of other collected data can likewise be gathered. To provide several other non-exhaustive and non-limiting examples, reference is made to Liang et al., Inf. Fusion, 52, 290-307, 2019, and specifically to FIG. 3 therein. Reference is also made to the embodiments described above, e.g., in Examples 1-9.

In some embodiments, 3D movement data is collected from a user moving towards or away from a cue. Such data can be collected using an electronic means, including a digital camera, which records the location of the cue, its distance from the user, and the 3D movement data of the user's body as the user moves towards or away from the cue.

B. Processed Data

After, or at the same time that, the data is gathered as collected data, it is processed by suitable analytical means (e.g., simple scoring, procedural or algorithmic analysis, artificial neural networking, machine learning or AI, etc.) to render it capable of being used to personalize a set of individualized diagnostic and therapeutic biomarkers for use in mental health therapy, including but not limited to PAT and BIT. In some aspects, for example, processed data is used to create metadata that can help diagnose mental health disorders based on known correlations between the collected data and certain mental health disorders. In other aspects, processed data is used to create metadata that can help identify certain triggers or stressors that either increase or decrease mental health symptoms, e.g., body movement increases or decreases manifest in situ with exposure to particular cues, images, sounds, scents, speech, or memories.

For instance, in some aspects, users can be encouraged to keep a digital journal to document their experience throughout the day, when they look in the mirror, when they weigh themselves, when they see images of others or interact with others, and when they receive feedback from others on how they look and what they're wearing. The text written by users is analyzed to assess emotional states. Various means of natural language processing (NLP) are known to those in the art, and can be applied.

In some aspects, various user data will be gathered and/or tracked while the app is open to assess, as non-limiting examples, mood, preferences, reaction time, option and/or cue selection, and time patterns of user input or user selection, including as part of specific questionnaires or surveys (i.e., as explicit data), or gathered as background or implicit data. These data also can be correlated with emotional state data, and used to personalize a set of diagnostic and therapeutic biomarkers.

In certain preferred aspects, an individual's baseline biometric and body movement data will be collected via VR body tracking and ML pose detection apps, the iMicro app, or a Wisdom Truffle (or equivalent device or system), which will be input to a machine learning protocol. Various machine learning algorithms, as well as the means to create such algorithms, will be known to those in the art. Such a protocol will take as input the processed data and optionally reference data and output a personalized set of diagnostic and therapeutic biomarkers, as well as emotional and physiological data, and such other predetermined or selected attributes and characteristics, which can be shared with a therapist, a clinician, or others involved in providing mental health therapy, including PAT and BIT.

In some embodiments, simultaneous with or subsequent to their capture, collected 3D movement data can be extracted, combined with other data including metadata, compressed, modified, manipulated, or otherwise processed by a processing means, to create a 3D movement data package.

Collected 3D movement data, such as 3D positional vectors and 4D quaternions collected by 3D motion capture means, or data packages as described above, may be rendered, processed, modified, manipulated, or otherwise processed as previously described according to any of the preceding embodiments or methods otherwise known to one of ordinary skill in the art.

In some embodiments the movement data, or various higher-level features extracted from such movement data, may be used to create adaptive music that can accompany a personalized diagnostic or therapeutic mental health protocol. Such music is created in Fmod using the Fmod Unity plugin, that allows the movement data to change the music track parameters in real time. In preferred embodiments, music is composed specifically to support different filters, and further consists of loops and layers that fade in and out depending on the sender's movements.

For example, one filter ("peaceful") uses the position of the hands to control cello and flute loops in the music, while a pose detection algorithm connects an open body posture to a musical "swell" overlay. Another filter ("explosive") uses velocity measurements to control bass and drums, and an average velocity over longer periods to control other portions of the track.

In some embodiments, collected data is processed to create a protocol for monitoring a user's well being through analysis of back posture. Stooped or closed posture is related to negative mood (see, e.g., Veenstra et al., Cognition and Emotion, 31:7, 1361-1376, 2017), while open posture is correlated with positive mood (see, e.g., Thrasher et al., Lecture Notes in Computer Science, v. 6974, Springer, 2011). By tracking posture changes as a proxy for mood, a protocol can address when negative mood is increasing, and directly counteract with a therapeutic intervention through PAT or a related therapy such as BIT.

In some embodiments, posture changes are used to inform or improve PAT or a related therapy such as BIT. In some embodiments, posture changes are associated with a positive patient experience. In some such embodiments, posture changes are used to predict or promote a positive patient experience, for example in a subsequent PAT or related therapy session, or for the PAT or therapy of another, similarly-situated, PAT or therapy patient. In other embodiments, posture changes are associated with a negative patient experience. In some such embodiments, posture changes are used to predict or prevent a negative patient experience.

A "similarly-situated" PAT or therapy patient may be determined based on comparing the biomarker(s) at issue, in some examples within predetermined ranges, according to methods herein and the general knowledge in the art, for instance by comparing individual patients, groups of patients, and/or by creating a class of patients using or based on defined and/or predetermined values or ranges of values of one or more biomarkers, such as 3D movement data.

In another embodiment, a biometric or body movement parameter that can fluctuate with well-being is "jitter," a measure of 3D body movement over time that is correlated with agitation, nervousness, and anxiety. By tracking this parameter and its variation over time, a protocol can address when negative emotion or motion is increasing, and directly counteract with a therapeutic intervention through PAT or a related therapy such as BIT.

In some embodiments, jitter is used to inform or improve PAT or a related therapy such as BIT. In some embodiments, jitter is associated with a positive patient experience. In some such embodiments, jitter is used to predict or promote a positive patient experience, for example in a subsequent PAT or related therapy session, or for the PAT or therapy of another, similarly-situated, PAT or therapy patient. In other embodiments, jitter is associated with a negative patient experience. In some such embodiments, jitter is used to predict or prevent a negative patient experience.

In another embodiment, a biometric or body movement parameter that can fluctuate with emotional state, such as sadness, is shoulder protraction, which can be measured over time through photogrammetric, VR body tracking, or ML pose detection technology. By processing data to identify shoulder protraction and its variation over time, biomarkers related to sadness can be objectively verified, tracked, and measured.

In some embodiments, shoulder protraction is used to inform or improve PAT or a related therapy such as BIT. In some embodiments, shoulder protraction is associated with a positive patient experience. In some such embodiments, shoulder protraction is used to predict or promote a positive patient experience, for example in a subsequent PAT or related therapy session, or for the PAT or therapy of another, similarly-situated, PAT or therapy patient. In other embodiments, shoulder protraction is associated with a negative patient experience. In some such embodiments, shoulder protraction is used to predict or prevent a negative patient experience.

In another embodiment, gait can be measured as a body movement parameter through VR body tracking. Slow gait and decreased stride length is correlated with schizophrenia, and slow gait and slumped posture is correlated with depression (see, e.g., Feldman et al., Austin Medical Sciences, 5(1): 1039, 2020), demonstrating how gait and its variation over time can be used to assist in mental health diagnosis.

In some embodiments, gait is used to inform or improve PAT or a related therapy such as BIT. In some embodiments, gait is associated with a positive patient experience. In some such embodiments, gait is used to predict or promote a positive patient experience, for example in a subsequent PAT or related therapy session, or for the PAT or therapy of another, similarly-situated, PAT or therapy patient. In other embodiments, gait is associated with a negative patient experience. In some such embodiments, gait is used to predict or prevent a negative patient experience.

In another embodiment, balance can be measured as a body movement parameter through VR body tracking and ML pose detection technology. Balance disorders are correlated with anxiety disorders and measuring balance and its variation over time can be used to both assist in mental health disorder diagnosis as well as efficacy of therapeutic intervention (see, e.g., Feldman et al., Austin Medical Sciences, 5(1): 1039, 2020).

In some embodiments, balance is used to inform or improve PAT or a related therapy such as BIT. In some embodiments, balance is associated with a positive patient experience. In some such embodiments, balance is used to predict or promote a positive patient experience, for example in a subsequent PAT or related therapy session, or for the PAT or therapy of another, similarly-situated, PAT or therapy patient. In other embodiments, balance is associated with a negative patient experience. In some such embodiments, balance is used to predict or prevent a negative patient experience.

In another embodiment, variation in head pose can be measured over time as a 3D body movement, which is correlated to exposure to specific cues or stressors in real time, and can be used to assist in both diagnostic and therapeutic efficacy. For example, specific stress conditions have been found to increase head mobility and mobility velocity, in both translational and rotational features, evidenced especially during tasks that involve a patient's speech. During patient intake, or during exposure to certain stressors during therapy, head pose and motion can therefore be measured to help determine what stressors may be particularly aggravating to a patient, further informing a set of personalized biomarkers used for diagnostic and therapeutic intervention. A study by Giannakakis et al., Conference Paper, 2018, offers an example of how head pose, mobility, and rotation and their variation over time can be studied over time through 3D imaging (see FIG. 1 of Giannakakis et al.).

In some embodiments, variation in head pose (including mobility and rotation) are used to inform or improve PAT or a related therapy such as BIT. In some embodiments, variation in head pose is associated with a positive patient experience. In some such embodiments, variation in head pose is used to predict or promote a positive patient experience, for example in a subsequent PAT or related therapy session, or for the PAT or therapy of another, similarly-situated, PAT or therapy patient. In other embodiments, variation in head pose is associated with a negative patient experience. In some such embodiments, variation in head pose is used to predict or prevent a negative patient experience.

C. Reference Data

In certain embodiments, collected data of at least one user that is processed through the aforementioned means can be compared against reference data to assist in creating a set of personalized diagnostic and therapeutic biomarkers useful in mental health therapy. Reference data can be aggregated data from any reference population, such as other users, for instance from other users of the iMicro app (or an equivalent product), the Wisdom Truffle (or an equivalent product), artificial neural networks, machine learning programs, VR body tracking and ML posture detecting apps, or clinical research studies. Alternatively, reference data can be aggregated data available from other sources such as across owners of a particular electronic means (e.g., fitness tracker, watch, smartphone application). Alternatively, reference data can be aggregated data available from published sources, such as from a systematic review of literature on biometric analysis, mental health clinical research, PAT, or related therapies such as BIT.

For example, Lewis-Smith et al., Body Image, 31: 309-320, 2019, conducted a review of the cognitive-behavioral roots of body image therapy and prevention, studying the pioneering work of Thomas Cash, the current state of theoretical and practical tools that BIT therapists can use with patients, and the path forward for subsequent research and practice. In reducing this research to practice, users of the iMicro app, for example, can be compared against the participants of other studies or the respondents of other surveys, who are similarly situated in terms of BIT treatment, to compare the efficacy of BIT and the success of certain theoretical and practical tools in preventing body-image disorders (See FIG. 1 of Lewis-Smith study, et al.).

In another exemplary aspect, reference data and collected data can be processed together, using such correlates of mental health and well-being as discussed in Liang et al., Inf. Fusion, 52, 290-307, 2019, as well as such additional sources of user data as their social media profiles. In any data gathering or collection, in all preferred embodiments herein, free, prior, and informed consent of each user will be obtained. See FIG. 2 of Liang, et al. as an example of how to collect data for mental health digital phenotyping, the data inputs of which can be used to create diagnostic and therapeutic biomarkers useful for mental health therapy.

In another exemplary aspect, Feldman et al., Austin Medical Sciences, 5(1): 1039, 2020, conducted a literature review of the current state of the art regarding gait and related physical aspects, including balance and posture, in patients suffering from depression, anxiety, or schizophrenia, and to formulate recommendations for the diagnosis and treatment of such patients. Users of the iMicro app, the Wisdom Truffle, VR body tracking and ML posture detecting apps, or others for whom 3D body movement data has been collected can be compared against the data set extracted from studies like those undertaken by Feldman et al. to test and verify the efficacy of recommendations for diagnosis and treatment made in such studies. See FIG. 1 of Feldman et al., which depicts an example of how to perform such systematic review. Those skilled in the art will appreciate that various iterations of such review with various sample sizes of articles reviewed at each step can be performed to achieve similar results and provide similar utility in cross-referenced study.

In another exemplary embodiment, collected data will be processed through the use of an artificial neural network or other AI-based machine learning program. Clinical research studies will use an amalgamation of collected data from at least one user and process such data through an artificial neural network in order to identify meta patterns, micro trends, macro trends, or other statistically significant analysis. Such analysis can be used to adjust treatment protocols, including medication doses, or to gain better insight on clinical data and the correlation between certain biomarkers and certain disorders and/or points of therapeutic intervention.

D. Personalized Diagnostic and Therapeutic Biomarkers and Protocol

After the processed data is optionally compared against the reference data, it can be compiled into a set of personalized diagnostic and therapeutic biomarkers and one or more protocols useful in mental health therapy.

Said biomarkers in accordance with embodiments of the invention include, but are not limited to: body posture, such as openness or closeness of posture; sway of the body or body parts as the body moves; balance of the user when standing still or in motion; a user's rhythm, measured by the cadence of motion of the body or body parts over time; body asymmetries, including but not limited to asymmetries between the left and right sides of the user's body; smoothness of motion of the body or body parts, including but not limited to a user's gait, head rotation, limbs, digits, and facial expressions; jerkiness of motion of the body or body parts, including but not limited to a user's head movement, gait, facial expressions, limb, and hand movements; body movement of a user as a user moves towards or away from a cue; kinetic energy of body parts; flexibility of the body or body parts, including but not limited to measures of range of motion, tilt, and distance between different body parts (e.g., sternum and pelvis);

reaction time, including but not limited to flinching or reflexive movements of eyes, limbs, and digits in response to stimuli; finger velocity and acceleration; a user's mental health history; the presence of any prescription or non-prescription drugs in the user's body over time; a user's height, weight, age, gender, location, and other biographical information; a user's biophysical readings and biometric data, such as heart rate, heart rate variability (HRV), electroencephalography measurement (EEG), pulmonary function, respiratory rate, brain entropy, body entropy, genetic biomarkers, and voice characteristics; eye movement; kinetic energy in the body; total amount of body movement, including but not limited to amount of 3D body movement measured over a volume of space and time; and any other biometric and body movement data that is taught herein or will be readily appreciated by those of ordinary skill in the art in view of the present disclosure as leading to the creation of as robust a profile of an individual's digital phenotype as can be rendered.

While in some embodiments, including certain preferred embodiments, biomarkers based on 3D human movement data are utilized, the disclosed invention can use or combine any of the aforementioned biomarkers, alone or in combination, and in combination in any number, and is not dependent upon the inclusion of any particular aforementioned biomarker in order to enable the invention. Indeed, it is the ability to mix and match different biomarkers, as described in various embodiments of the invention, that further advances the invention over the prior art.

Generally, those of ordinary skill in the art will readily appreciate how to identify a set of personalized biomarkers, including but not limited to the aforementioned biomarkers, for diagnostic purposes in identifying potential mental health disorders. For example, Feldman et al., Austin Medical Sciences, 5(1): 1039, 2020 identified forty-eight different articles by mental health professionals to conduct a study on how biomarkers such as gait, balance, and posture correlate with mental health disorders, including depression, anxiety, schizophrenia. In another study, Lewis-Smith et al., Body Image, 31: 309-320, 2019, identified the cognitive-behavioral roots of body-image disorders and the relevant biomarkers that correlate with such disorders.

Similarly, those of ordinary skill in the art will readily appreciate how to identify a set of personalized biomarkers for therapeutic purposes in mental health treatment, including for the use of PAT and BIT. For example, Giannakakis et al., Conference Paper, 2018, demonstrates how researchers can study biomarkers such as head pose, mobility, and rotation in real time with 3D-imaging and assess how such biomarkers change in real time to specific cues and stressors, such as those that could arise during mental health therapeutic treatment.

The correlation between biomarkers and their variability when a user is exposed to certain cues and stressors enables the biomarkers to be used in creating personalized diagnostic and therapeutic protocols. By analyzing processed data about how certain biomarkers vary when an individual is exposed to certain cues or stressors, personalized protocols are developed that efficiently target mental health triggers and enable PAT or BIT to more efficiently identify and isolate topics for integration during mental health therapy. The means for such correlation is identified through the aforementioned means for processing collected data, including through the use of AI, artificial neural networks, machine-learning protocols, or reference to clinical and academic studies.

In some aspects, a personalized therapeutic protocol is developed by correlating a user's exposure to a particular cue or stressor (e.g., an image from the user's past) to biomarkers including but not limited to decreased postural alignment, slumped shoulders, increased head mobility, emotional distress, or increased heart rate. Such a protocol may call for a measurement of a user's biomarker variability before and after exposure to the stressor, creating a personalized dataset that can serve as a benchmark for use in PAT or BIT.

In other aspects, a personalized diagnostic protocol is developed by measuring a user's biomarkers prior to a diagnostic session and then tracking the variability of the biomarkers throughout the session as the user undergoes established diagnostic methods for mental health disorders. The resulting dataset can be compared to reference data correlated with other users who have undergone similar diagnostic methods, and the initial user's biomarker variability can be benchmarked against the reference data to better isolate and diagnose specific disorders that might emerge through biomarker data comparison.

In some embodiments, the personalized diagnostic and therapeutic biomarkers and protocol will include a 3D movement data package, as described in the invention.

In some embodiments, the personalized diagnostic and therapeutic biomarkers and protocol are converted into a digital file and saved to permanent storage. The file, or 3D movement data package, can be digitally appended to a user's digital medical history or profile and sent to a doctor, mental health therapist, insurance provider, or other health-service provider.

In some embodiments, the digitally saved personalized diagnostic and therapeutic biomarkers and protocol can be uploaded to cloud-based or downloaded software, including but not limited to mobile applications, and used as an input into clinical research on mental health disorders to test efficacy, find outliers, or tailor drug interventions based on the user data.

In some exemplary embodiments, evolving personalized PAT protocols will be validated through correlating the user's emotional data, as assessed through a questionnaire or journal, with the user's biometric and body movement data collected through 3D posture, VR body tracker, or ML pose detection apps, and interactions with the Wisdom Truffle, for example. For example, if a PAT intervention was increased in response to declining posture, subsequent biometric and body movement data would be probed for correlations between improvements in posture with reports of the user's mood. A positive correlation between therapeutic intervention, mood, and posture would verify that the personalized protocol is associated with increased positive mood.

In another exemplary embodiment, evolving personalized BIT protocols will be validated through correlating the user's body-image data, as assessed through a questionnaire or journal, with the user's biometric and body movement data collected through 3D posture, VR tracker, or ML pose detection apps. For example, if a BIT intervention was increased in response to declining balance and body dysmorphia, subsequent biometric and body movement data would be analyzed for correlations between improvements in balance with reports of healthier and more objective perceptions of the user's body. A positive correlation between BIT, balance, and decreased body dysmorphia would verify that the therapeutic intervention and protocol is associated with a healthier body image.

In some embodiments, the digitally saved personalized diagnostic and therapeutic biomarkers and protocol can be further used by health-service providers or clinical researchers to train artificial neural networks, or other machine learning applications, such as those that will be readily known and appreciated by one of ordinary skill in the art to model neural changes in the human brain and help to predict the severity, duration, and treatability of mental health disorders (including by AI, other machine learning, and edge-computing software). Machine learning is an application of AI that provides systems the ability to automatically learn and improve from experience without being explicitly programmed, for instance in applications where it is difficult or infeasible to develop conventional algorithms to perform needed tasks. Machine learning algorithms build a mathematical model based on sample data, known as "training data." In all preferred embodiments, such data will be shared only with explicit user consent. Thus, the biomarkers and protocol can be used in some embodiments to help recognize hidden patterns and correlations in raw data, further assisting clinical research in optimizing its selection of controlled and/or randomized participants for clinical studies.

In some embodiments, personalized diagnostic and therapeutic biomarkers and protocol, stored as 3D movement data or a 3D movement data package, will be used to train machine learning models. Stored 3D movement data therefore will provide novel and valuable training data for machine learning applications (e.g., to train AI to understand human body language as described in embodiments above).

In some preferred embodiments, the user will upload the personalized diagnostic and therapeutic biomarkers and protocol to the iMicro app, a Wisdom Truffle, or similar personal recording apps and devices.

In some embodiments, the digitally saved personalized diagnostic and therapeutic biomarkers and protocol will be sent to a guide for PAT and used to help the guide prepare for a psychedelic preparation session. Such user data can then be used by PAT guides to appropriately group a user with other users for preparation sessions.

In other embodiments, the digitally saved personalized diagnostic and therapeutic biomarkers and protocol will be sent to a mental health therapist, including one that provides BIT. Such data will enable the therapist to prepare for BIT by cross-referencing the user's data with other reference data, or as a supplement to studying a user's other medical history records.

In one exemplary embodiment, subsequent biometric and body movement data will be assessed for deviations from a baseline set of personalized diagnostic and therapeutic biomarkers and protocol. Deviations will inform adjustments to the protocols. For example, if biometric and body movement data shows relative improvement, no adjustment to a PAT or BIT protocol may be needed unless specifically requested by the user. If over time a biometric or body movement parameter begins to decline, the PAT or BIT protocol can be modified (e.g., increased), depending on the context of the decline.

In some embodiments, movement data of a user towards or away from a cue, including but not limited to the 3D body movement data of a user, can be used to create a set of diagnostic biomarkers and protocol. For example, movement data of a user moving towards a cue can be referenced against other comparable data of the same or other users moving towards the same, or similar, cue and such data can be used to assist in mental-health diagnosis. Such data can also be used, individually or collectively, to create a diagnostic protocol for certain mental-health disorders, and subsequently utilized for PAT or related therapies such as BIT.

E. Personalized Biomarker-Augmented Mental Health Therapy

Another aspect of the invention is to utilize the personalized diagnostic and therapeutic biomarkers and protocol for personalized biomarker-augmented mental health therapy, including but not limited to PAT and related therapies such as BIT. Biomarker-augmented mental health therapy can be delivered through self-assessment tools such as data aggregators, digital diaries, or web-based applications (e.g., iMicro app); through the assistance and guidance of mental-health professionals utilizing biomarkers to inform, customize, and tailor mental-health therapy to the individual needs of the user; or through the use of biomarkers to advance clinical trials and research into mental-health pharmaceutical intervention wherein biomarkers can be used to gain a more robust understanding of study participants' phenotypes and the effects of pharmaceutical intervention on the targeted treatment.

In some embodiments, mental-health self-assessment tools known to one of ordinary skill in the art, such as journaling and recording of daily mental-health status, will be augmented by biomarkers in order to develop a more robust picture of an individual's mental health that goes beyond what is often subjective self-reporting of emotional well-being. For example, a mental health patient with a practice of self-assessment through journaling of mental health well-being can augment the journaling with daily inputs of biomarkers through the aforementioned data collection and processing tools, preferably with the iMicro app or Wisdom Truffle. The biomarkers can then be correlated with the journaling inputs and dynamically updated through the use of AI, machine learning, or use of other proprietary algorithms. Users can then gain new insights into their own mental-health status by comparing how their self-reporting of emotional well-being compares with objective biomarker measurements and variability over time.

Thus, for example, if a user self-reporting for some time as feeling sad and displaying biomarkers such as slumped shoulders and a slow gait, which are known indicators of depression (see, e.g., Feldman et al., Austin Medical Sciences, 5(1): 1039, 2020), suddenly reports a feeling of euphoria and self-aggrandizement without any change in biomarkers, the user can be on the lookout for potential onset of a manic, hypomanic, or "mixed state" episode (i.e., simultaneous depressive and manic episodes). Because individuals with bipolar disorder are often unaware of their mood changes in real time, the augmentation of biomarkers to self-monitoring and self-assessment can provide new and useful information for therapeutic intervention.

In implementations directed to PAT, BIT, and related therapies, the methods and systems for personalized biomarker-augmented mental-health therapy using personalized diagnostic and therapeutic biomarkers and protocol, including those comprised of 3D human movement data according to embodiments of the invention, may be used as part of a process to capture and store movements of patient(s) during PAT or BIT sessions in order to identify, track, and/or define characteristic movements associated with negative or difficult experiences in PAT, BIT, and related therapies, such that the defined characteristic movement markers are used to update the personalized diagnostic and therapeutic biomarkers and protocol. Similarly, such methods and systems may be used to identify, track, and/or define characteristic movements associated with positive or good experiences and outcomes in PAT, BIT, and related therapies, and the defined characteristic movement markers are used to verify the personalized diagnostic and therapeutic biomarkers and protocol. Moreover, such methods and systems using 3D human movement data may be used to playback gestures and/or characteristic movements as a therapeutic and/or teaching aid for the patient(s) during sessions of PAT, BIT, and related therapies, or for the facilitator or medical professional.

In implementations directed to PAT, BIT, and related therapies, the methods and systems for personalized biomarker-augmented mental-health therapy using personalized diagnostic and therapeutic biomarkers and protocol, including those comprised of 3D human movement data according to embodiments of the invention, may be used to provide a digital platform for administering PAT, BIT, and related therapies which is scalable from individual one-on-one PAT or BIT sessions up to widespread and general usage of PAT or BIT by the general public. For example, multiple patients can interact with the 3D movement data of a single facilitator or therapist, and/or a single facilitator or therapist can interact with the personalized diagnostic and therapeutic biomarkers and protocol of multiple patients.

For example, in some embodiments, personalized diagnostic and therapeutic biomarkers and protocol, including those containing 3D movement data, is used to enhance and accelerate the treatment process in PAT or BIT, and/or to enable such PAT or BIT to be scaled up and brought to larger groups of patients with fewer therapists, reduced demands on therapist time, and/or other efficiencies as will be appreciated.

In further embodiments, patterns of biomarker variability can be analyzed through AI, machine learning, or artificial neural networking to identify individualized biomarker patterns that correlate with mental health disorder recurrence or exacerbation. Such patterns can be pre-programmed into mental-health treatment protocols and self-care measures (e.g., through an electronic means) in order to take preventative actions that help stop a user from engaging in unhealthy behavior correlated with the mental health disorder. For example, a bipolar patient might automatically freeze their credit cards when biomarkers correlated with manic episodes appear so as to avoid unwanted spending sprees. In another example, a user with a body-image disorder might automatically disable a scale when certain biomarkers appear so as to not engage in unhealthy obsessive-compulsive triggers like repeatedly weighing oneself.

In implementations directed to PAT, BIT, and related therapies, the methods and systems for personalized biomarker-augmented mental-health therapy using personalized diagnostic and therapeutic biomarkers and protocol, including those comprised of 3D human movement data according to embodiments of the invention, may be used to provide psychological support to patients during one or more of the screening session(s), preparation session(s), psychedelic dosing session(s), integration session(s), and/or after-care/relapse management session(s). Moreover, such methods and systems may be used to provide the patient with a consistent, controlled, and calm environment during PAT dosing sessions, and/or to customize and optimize the patient's PAT experience.

In implementations directed to PAT, BIT, and related therapies, the methods and systems for personalized biomarker-augmented mental-health therapy using personalized diagnostic and therapeutic biomarkers and protocol, including those comprised of 3D human movement data according to embodiments of the invention, may be used to provide remote connections and interactions between the therapists (or facilitators, "guides," clinical psychologists, psychiatrists, other trained medical professionals, and the like) monitoring/overseeing the PAT, BIT, or related therapy and the patient(s) of that PAT, BIT, or related therapy, and/or between and among the patients themselves.

In another embodiment, a user's personalized diagnostic and therapeutic biomarkers and protocol are sent to a mental-health therapist, including but not limited to a PAT therapist or a body-image therapist, or other like therapist for a related therapy, and used to conduct therapy inside, or with the assistance of, a virtual-reality (VR) or augmented-reality (AR) electronic system. In some embodiments, the therapy conducted with the VR electronic system enables a user to perform actions inside a VR avatar's body that differs from the user's body. By doing actions inside an unfamiliar body, the user's neural plasticity will increase, helping the user to more efficiently learn and remember new patterns of behavior aligned with the goals of the therapy. Such therapy can target the learning and patterning of behaviors correlated with the personalized biomarkers and protocol, using biophysical feedback (e.g., haptic feedback, sensory feedback, etc.) enabled through the VR electronic system to inform a user when certain actions or behavior are in line or out of line with the goals of the therapeutic treatment.

Thus, for example, a user with a body image disorder can undergo BIT through a VR electronic system wherein the user performs actions and behaviors inside an avatar with a body designed by a mental-health therapist especially for the user, based on the user's personalized diagnostic and therapeutic biomarkers and protocol, to help correct the unhealthy actions and behaviors of the user (e.g., target specific points of body dysmorphia and any correlated biomarkers unique to the user). One of ordinary skill in the art will readily appreciate how actions and behaviors undertaken in a foreign body will increase the user's neural plasticity, thereby leading to more efficient learning and long-lasting benefits of BIT. Through the use of a VR electronic system, the therapy can be conducted through one or more sessions in a therapist's office, or through one or more sessions of telemedicine counseling, or "telecounseling" (e.g., provided virtually or over remote means, using an electronic means).

In another embodiment, a user can send digitally saved personalized diagnostic and therapeutic biomarkers and protocol to a PAT therapist or guide (here, as elsewhere, equivalently and interchangeably, as well as interchangeably with facilitator, health professional, and the like) using an electronic means. The PAT guide can upload the biomarkers and protocol into a virtual program for PAT (e.g., FireflyVR, Isness, etc.). The guide can then prepare for a PAT session by creating a plan with the user or patient (here, as elsewhere, equivalently and interchangeably, as well as interchangeably with subject, client, and the like) for how to respond and react to a user's biomarker variability during PAT, with the user's free, prior, and informed consent.

For example, if a guide observes variation of a user's biomarkers in a pre-described manner that is known to be correlated with certain triggers or stressors that the user would like to address (e.g., pattern of head movement, speech, and breathing rate apparent when a user is experiencing acute mental health symptoms), the guide and user can plan in advance on techniques the guide can use to calm the user, or to explore the state of stress in ways that safely open the user up to addressing certain traumas that the user might wish to confront during PAT. During the PAT, the guide can then implement the customized plan with the user when the user expresses the predefined biomarker variability. As will be appreciated by those of ordinary skill, the act of setting plans for a safe and consensual response to a user's unique triggers, measured through the user's biomarkers, itself can also help to ensure a positive, safe, and efficacious PAT.

Haptic feedback is also provided in some embodiments, for instance vibrations may be activated when touching an avatar, communicating the sensation of physical presence. Such physical presence enhances the ability to play touch-based mirroring games asynchronously, as part of mental health treatment.

In embodiments where the methods and systems of the invention are used as part of PAT or body-image therapy, haptic feedback also permits a therapist and a patient to interact by touch.

In embodiments where pre-recorded 3D movement data of a therapist is used with a patient, the 3D movement data of the patient can be monitored and referenced against the patient's personalized diagnostic and therapeutic biomarkers and protocol to determine when psychological support such as arm holding may be beneficial, and the pre-recorded touch can be provided to the patient's avatar at such times, effectuating psychological support, the trigger for such provision being, e.g., any predetermined trigger or cue or one based on the personalized diagnostic and therapeutic biomarkers and protocol.

In another embodiment, users' personalized diagnostic and therapeutic biomarkers and protocol can be aggregated to create a portfolio of biomarkers that can be used to enhance randomization and control inside clinical research studies for mental-health therapy. For example, clinical researchers could screen participants for studies and trials by seeking a certain balance or diversity of biomarkers across the entire group of study participants. Data collected throughout the study could be processed by machine learning, artificial neural networks, or proprietary algorithms to identify meta trends in the data and to better isolate the efficacy of given treatment to specific biomarkers, protocols, or digital phenotypes. Such data and analysis can then be used to further tailor pharmaceutical interventions based on an individual's unique set of biomarkers.

In some embodiments, the personalized diagnostic and therapeutic biomarkers and protocol may be comprised of a 3D movement data package. A user may send this package to a mental-health professional or therapeutic service provider through an electronic means. Once received by a recipient device (e.g., a device belonging to a mental-health professional or therapeutic service provider), a 3D movement data message may be viewed by recipient (or, in some embodiments, received by more than one recipient device and/or viewed by more than one recipient). It also may be stored on permanent storage.

A 3D movement data package may be stored before and/or after it is viewed, and storage may be by default software rule or by user selection. For instance, a recipient may not be available or may not wish to view a 3D movement data message immediately, and thus it may be saved by the decision of a recipient device or a recipient for later viewing. Or, a recipient may view it immediately, and then decide to store it permanently for repeat viewing, e.g., in a "saved" folder or a "favorites" folder. One of skill will understand that many design choices involving storage are possible, and within ordinary skill.

In some embodiments, viewing a 3D movement data package is made possible with a 3D motion rendering means and output means. A suitable 3D motion rendering means is any hardware, software, or hardware/software combination (whether as a single module or combination of modules) that is capable of rendering a 3D movement data package as a 3D movement object, regardless of the specific technical basis on which such rendering is performed (e.g., whether rendering is generated ahead of time (pre-rendered) or in real-time, regardless of choice of specific rendering algorithm, etc.).

Many rendering algorithms are known to ordinary artisans, and software used for rendering may employ any number of different techniques to obtain a final animation. For instance, in embodiments that capture 3D movement data using a time series of positional vectors and quaternions to represent joints across time t, a suitable 3D motion rendering means will be able to recreate a skeleton model comprising those joints, in like positions. That time series of 3D movement data is used to animate the skeleton model, using mathematical processes known in the art, such as inverse kinematics, combined with suitable animation techniques (e.g., skeletal animation or "rigging," and "skinning").

Preferably, but optionally, a user may view her own 3D movement input on an output means during personalized mental-health therapy. Suitable output means are understood to be those comparable to the screen of a user's device, a VR headset, a monitor or TV, a projector or holographic display, a stereo display or 3D display, etc. When 3D movement is rendered on an output means, it will be understood that processing means further includes suitable 3D motion rendering means, whether as hardware, software, or hardware/software combinations. In certain preferred embodiments, the user's avatar is rigged as a mirrored puppet, allowing for real-time feedback of the user's own movements as part of the mental health treatment.

In some embodiments, the 3D motion rendering performed by processing means will optionally use select personalized diagnostic and therapeutic biomarkers and protocol, so that a user is therefore able to select and try on different avatars, corresponding to different protocols, experiment with various filters and feedback, corresponding to different biomarkers, and otherwise set and change parameters and view and interact with her 3D movement input in real time, whether or not it is also being captured.

Depending on the embodiment, various protocols can be determined based on the user's 3D movement; alternately, they can be determined by other input, or through choices made through an alternate input, using an optional additional input means, such as voice, the touchscreen of smartphone or tablet device, or controls of a VR device.

Additional input means also may include sensing means for responding to (i.e., providing feedback based on) or recording (along with 3D movement data, whether ultimately included in a 3D movement message or not) physiological, physiometric, or biometric data such as that relating to cardiovascular and pulmonary functions (e.g., pulse rate, heart rate variability (HRV), ECG traces, blood oxygenation, respiration rate, temperature or $CO_2$ content of exhaled air, heart sounds, body resonance), brain activity (e.g., encephalography such as electroencephalography (EEG), quantitative EEG (qEEG), magnetoencephalography (MEG), electrocorticography (ECoG), functional magnetic resonance imaging (fMRI), positron emission tomography (PET), nuclear magnetic resonance (NMR), spectroscopy or magnetic resonance spectroscopy (MSR), single-photon emission computed tomography (SPECT), near infrared spectroscopy (NIRS), functional NIRS (fNIRS), or event-related optical signal (EROS)), electrodermal activity (e.g., skin conductance), and other such alternative input types.

In yet other embodiments, rather than be transmitted to a recipient device to be output to a screen, and viewable to a recipient, a set of personalized diagnostic and therapeutic biomarkers and protocol comprised of 3D movement data will be transmitted to a device to be output so as to control a puppet, toy, robot, or similar physical device. In these embodiments, rather than be graphically rendered as an animation, the 3D movement data will be converted to control signals to operate a mechanical apparatus, using methods known to those of ordinary skill (e.g., mapping the captured motion of human joints to like joints of the mechanical apparatus, mapping other captured human movement features to the movement of the mechanical apparatus, and the like) as part of mental health therapies, such as PAT and related therapies, and including BIT.

In some embodiments, size will be manipulated toward therapeutic ends. For example, a patient undergoing PAT or BIT such as described herein may be given an avatar with, e.g., different body parts or proportions, as part of a therapeutic protocol to manage the distress or symptoms of one or more body dysmorphic disorders.

Besides embodiments where a personalized set of biomarkers and protocol is transmitted from one user to one mental-health therapist, and besides those additional embodiments where a personalized set of biomarkers and protocol is transmitted from one user to multiple mental-health therapists (including a defined group or class of recipients), yet further embodiments exist where personalized sets of biomarkers and protocols are transmitted between multiple users and multiple mental-health therapists (including defined groups or classes).

In these further embodiments, it will be readily appreciated how personalized sets of biomarkers and protocols, optionally comprised of 3D movement data, does not only form a novel medium of communication between patient and therapist, but also forms the basis for a novel mental-health treatment platform. For example, transmission of personalized sets of biomarkers and protocols between groups of patients and therapists permits the creation of novel 3D-enhanced mental-health therapy, such as interactive and/or asynchronous forums for sharing and support among patients with similar mental health disorders.

Such 3D-enhanced mental-health therapy may also include group classes for yoga, movement, exercise, or other physical therapy, enabling instances where the therapist and patients can share and interact with each other's physical movements and utilize novel forms of feedback, facilitating skill acquisition and training.

For example, in one embodiment, a group of (i.e., two or more) patients will interact between and among themselves during a PAT or BIT session by, e.g., sharing gestures and/or performing physical exercises as a group, according to the teachings herein.

In one embodiment, a therapist overseeing a PAT dosing session will remotely "attend" the PAT dosing session with the patient, and will interact through sending or sharing 3D movement data to provide psychological support. This advance over the art will reduce the need for specially trained therapists who can provide high-quality care to patients as part of PAT, and/or reduce the burden on individual such therapists.

For example, in some embodiments a single therapist will provide psychological support or other care to multiple patients across space and/or time, efficiently shifting from patient to patient with guidance from each patient's set of personalized diagnostic and therapeutic biomarkers and protocol. In some such embodiments, a single therapist will provide care to multiple patients who are "separate" from one another (i.e., who are unaware of the presence of each other, as if a single therapist is in the "rooms" of multiple patients all at the same time). In other such embodiments, a single therapist will provide care to multiple patients who are "together," for example in a group preparation session, group drug-administration session, or group integration session (i.e., if all such patients are together in a single "room" or other virtual space or location). "Together" will be understood to mean that the patients are aware of the presence of each other (e.g., are able to see and optionally interact with each other's avatars) not necessarily that all are in the same room or location in physical space, or even necessarily that all are together during the same time, as some patients' presences may in certain embodiments be pre-recorded (e.g., as stored 3D movement data).

In some embodiments, different 3D movement data of a therapist will be recorded and saved, e.g., to permanent storage. The pre-recorded 3D movement data of a therapist will thereafter be available to be used with one or more patients (e.g., used non-contemporaneously or asynchronously), and will be so used, minimizing or eliminating the need for the therapist to interact with the patient(s) at one or more times during PAT or BIT.

As the above exemplary implementations demonstrate, biomarker-augmented and 3D-enhanced mental-health therapy will be curated or designed in any number of novel ways, for any number of never-before-seen applications, and the limit resides only in the imagination of an ordinary artisan armed with knowledge of this disclosure.

F. Resulting Improvements in Mental-Health Therapy and Research

In certain aspects, the method of the invention will result in an improvement to the user of a mental disease or disorder, including body-image disorder, an improvement in a health condition, or an improvement in overall health and well-being, or overall functioning. For example, in some embodiments, the invention will have beneficial results such as increased energy, better posture, better sleep, less anxiety, less depression, more focus, more creativity, healthier understanding of the body, and/or increased calmness.

In some aspects, a user may have a mental health disorder, or a condition related to a mental health disorder for which treatment may be efficacious. Users may be in need of treatment for a disorder, predisposed to a disorder, and may or may not be diagnosed with a disorder. Users may be receiving treatment or therapy for a mental health disorder, or may receive therapy or treatment for a mental health disorder in the future. In some embodiments, the disclosed methods also can be used to improve mental health and improve psychological functioning in non-disease states, i.e., in a user without a diagnosed mental disorder, or specific symptoms thereof. Users therefore need not have a disorder or a diagnosis of a disorder, or any symptoms of a disorder, to benefit from certain disclosed embodiments of the invention (even if, e.g., referred to as a "patient" herein, or as participating in psychedelic-assisted "therapy").

Other contemplated uses for which large sets of personalized diagnostic and therapeutic biomarkers and protocol, including those containing 3D human movement data, will have novel and significant applications include computational statistics, data mining and "knowledge discovery in databases" (KDD), predictive analytics, user behavior analytics, and generally such applications within computer science, statistics, and data analytics that have the overall goal of using large and complex data sets and intelligent methods to extract information.

Besides mental health disorders, it will be understood that the personalized diagnostic and therapeutic biomarkers and protocols of the invention will be useful to treat other conditions, such as anxiety related to a cancer diagnosis, or related to terminal illness.

Moreover, the personalized diagnostic and therapeutic biomarkers and protocols of the invention will be appreciated to be useful for providing improvements in physiological or psychological functioning, and for general improvements in health and well-being, including the betterment of self-described or otherwise "healthy" people and the "betterment of the well."

Moreover, any of the disclosed personalized diagnostic and therapeutic biomarkers and protocols can be used in combination with one or more therapeutically beneficial activities, where such activities provide an additional therapeutic effect or increase an existing therapeutic effect, where such participation follows or is in conjunction with administration of the biomarker-augmented mental health therapy, including breathing exercises, meditation and concentration practices, focusing on an object or mantra, listening to music, physical exercise, stretching or bodywork, journaling, grounding techniques, positive self-talk, or engaging with a pet or animal, and it should be understood that such participation can occur with or without the participation or guidance of a therapist or other professional, although such participation or guidance may optionally be provided through the embodiments as discussed above.

As used in the invention, the terms "treating" or "treatment" of a disorder includes: (i) inhibiting the disorder, i.e., arresting or reducing the development or progression of the disorder or its clinical symptoms; or (ii) relieving the disorder, i.e., causing regression of the disorder or its clinical symptoms. Inhibiting the disorder, for example, would include prophylaxis. Hence, one of skill in the art will understand that a therapeutic amount necessary to effect treatment for purposes of this invention will, for example, be an amount that provides for objective indicia of improvement in patients having clinically-diagnosable symptoms.

The effect may be prophylactic in terms of completely or partially preventing a disorder or symptom thereof and/or may be therapeutic in terms of a partial or complete cure for a disorder, an adverse effect attributable to the disorder, and/or a comorbidity simultaneously present with the disorder.

Moreover, "treatment" as used herein covers any treatment of a disorder in a user, and includes: (a) preventing a disorder from occurring in a user who may be predisposed to the disorder but has not yet been diagnosed with it; (b) inhibiting a disorder, i.e., arresting its development; (c) relieving a disorder, i.e., causing regression thereof; (d) protection from or relief of a symptom or pathology caused by or related to a disorder; (e) reduction, decrease, inhibition, amelioration, or prevention of onset, severity, duration, progression, frequency or probability of one or more symptoms or pathologies associated with a disorder; and (f) prevention or inhibition of a worsening or progression of symptoms or pathologies associated with a disorder or comorbid with a disorder.

The term "mental health disorder" generally refers to a disease condition that generally involves negative changes in emotion, mood, thinking, or behavior. Examples of mental health disorders include anxiety and stressor-related disorders, dissociative disorders, eating disorders, mood disorders, obsessive-compulsive and related disorders, personality disorders, bipolar and related disorders, schizophrenia and related disorders, sexuality, gender dysphoria, and paraphilias, somatic symptom and related disorders, suicidal behavior and self-injury, and substance-related disorders. (See Merck Manual of Diagnosis and Therapy, 20th Ed. (2018).) Included among such disorders are therefore depression including in forms such as treatment-resistant depression and major depressive disorder (including bipolar, manic, and hypomanic disorders that may accompany or correlate with depressive disorders), dysthymia, anxiety and phobia disorders (including generalized anxiety, social anxiety, panic, post-traumatic stress and adjustment disorders), feeding and eating disorders (including binge eating, bulimia, and anorexia nervosa), other binge behaviors, body dysmorphic syndromes, alcoholism, tobacco abuse, drug abuse or dependence disorders, disruptive behavior disorders, impulse control disorders, gaming disorders, gambling disorders, memory loss, dementia of aging, attention deficit hyperactivity disorder, personality disorders (including antisocial, avoidant, borderline, histrionic, narcissistic, obsessive compulsive, paranoid, schizoid and schizotypal personality disorders), attachment disorders, autism, and dissociative disorders.

Example 10: Use of 3D Movement Data for Improving Patient Safety During Therapy

Patient safety is a concern in therapeutic settings, particularly during mental health therapies, and especially during PAT. The power imbalance between the therapist and the patient is especially enhanced by a patient's altered state of mind (and, in cases, increased suggestibility) during PAT (see, e.g., Carhart-Harris, et al. Psychopharmacology (Berl). 2015; 232(4):785-794). The MAPS Code of Ethics contains a section focused on special considerations for patients in altered states of consciousness, which explains that "participants in non-ordinary states of consciousness may be especially open to suggestion, manipulation, and exploitation; therefore, we acknowledge the need for increased attention to safety, sexual boundaries, and consent" (see MAPS MDMA-Assisted Therapy Code of Ethics. MAPS Bulletin Spring 2019: Vol. 29, No. 1). Nevertheless, numerous high-profile instances of safety issues (i.e., non-consensual touching and sexual assault) have occurred (see, e.g., Bethany L. "As psychedelic therapy goes mainstream, former patient warns of danger of sexual abuse." CBC/Radio-Canada. Published Mar. 18, 2021. Accessed Jan. 25, 2023).

Existing safety systems have major drawbacks in terms of efficacy, as well as privacy. The first line of defense against safety issues has historically been to ensure that more than one therapist is present during a therapy session (e.g., a "dyadic" male and female pair). Unfortunately, this has in some cases been ineffective at preventing safety issues, such as non-consensual touch (id.). Video recording of therapy sessions has been used to document inappropriate behavior and hold therapists accountable (id.). However, video recording does not provide a means for immediate intervention during an ongoing safety issue. Real-time video surveillance, monitored by a therapy supervisor, could theoretically accomplish this goal. However, video recording and real-time video surveillance both create privacy, security, and confidentiality issues, especially with PAT, which may be stigmatized (or in some cases criminalized) in certain situations.

Aside from these concerns, patients may not wish to be recorded during a session in which they feel emotionally vulnerable. There is therefore an urgent and unmet need for methods and systems to improve patient safety during mental health therapy (especially PAT) while ideally maintaining patient privacy.

Figure 14:
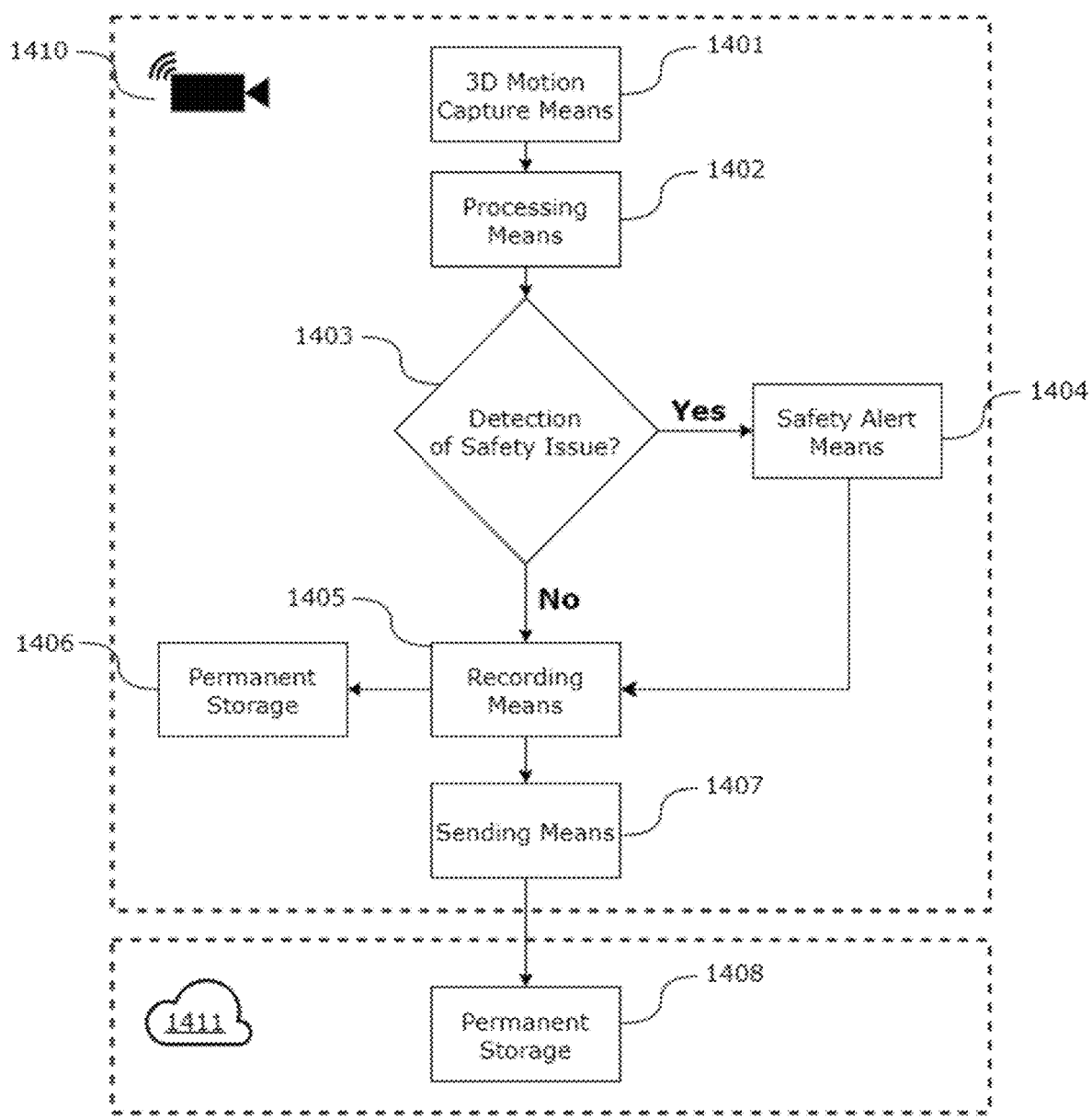
FIG. 14 is a flow diagram illustrating an exemplary system for improving patient safety during mental health therapy in accordance with embodiments of the invention.

In some embodiments, 3D movement data is used to improve patient safety during mental health therapy, such as psychedelic-assisted therapy (PAT) or related therapies like body-image therapy (BIT). To this end, an exemplary system is described herein, with reference to FIG. 14.

In these embodiments, a safety monitoring system includes a safety monitoring device 1410 having a 3D motion capture means 1401, processing means 1402, recording means 1405, and sending means 1407. The 3D motion capture means 1401, processing means 1402, recording means 1405, and sending means 1407 are components according to various embodiments described above.

In some embodiments, the safety monitoring system includes determining whether a safety issue is occurring (1403), for example by analysis of processed 3D movement data. In some embodiments, the detection of a safety issue is based on detecting inappropriate touch between a therapist and a patient, such as a therapist touching a patient in a non-consensual manner. The distinction between appropriate and inappropriate touch (i.e., a safety issue) can in some embodiments be predetermined before the therapy session. For example, the therapist and the patient can discuss whether platonic touching is allowed, and if so, what type of touching (e.g., therapist and patient may hold hands, therapist may touch the patient's forehead). In some embodiments, touching that goes beyond the scope of a predetermined set of acceptable platonic touch movements is considered inappropriate touch. Certain touches and movements will always be inappropriate during PAT, such as touching that is sexual in nature. In some embodiments, the accuracy of the system that identifies a safety issue can be improved by customizing the detection algorithm to account for predetermined positions for the therapist and the patient (e.g., the patient will be supine on a bed, and the therapist will be sitting in a chair facing the patient).

In some such embodiments, a safety issue can be identified by detecting the therapist out of their chair and in close proximity to the patient. In some embodiments, the accuracy of the system that identifies a safety issue can be improved by customizing the detection algorithm to account for the specific layout (e.g., furniture, such as soft furniture, such as a couch or bed; plants; high-resolution sound system) and/or lighting in the therapy environment. Where the light in the room is dimmed and/or light levels are kept or adjusted to be relatively low, the system will be adapted to such conditions, using ordinary skill. Other methods for determining whether a certain touch or movement constitutes a safety issue will be apparent to those of skill.

Regardless of what methods are used to define a safety issue, the safety monitoring system described in these embodiments comprises a safety alert means 1404 to perform one or more safety alert steps subsequent to detecting a safety issue.

In some embodiments, the safety alert is a communication to a third-party, such as a supervisor, another therapist, staff member, or somebody who can otherwise intervene and assist the patient, whether on- or off-site. In some embodiments, the safety alert is a communication to a predetermined person of the patient's choosing (e.g., an emergency contact). In some embodiments, the safety alert is a recording system (e.g., a photographic, video, and/or audio recording system) that records the interactions between the therapist and the patient and documents the safety issue. In some embodiments, the safety alert is an alarm.

In some embodiments, 3D movement data is stored on the safety monitoring device 1410 having a recording means 1405 and some form of permanent storage 1406, as described in various embodiments herein. In other embodiments, the safety monitoring device 1410 comprises a sending means 1407 that transmits the 3D movement data to a permanent storage 1408 in a location other than the safety monitoring device (e.g., cloud storage 1411, or another suitable remote storage device). In some embodiments, such as where no safety issue has been detected, or no safety issue has been detected of a certain predetermined type or of a predetermined threshold, patient consent may be obtained and the stored 3D movement data can be used for research purposes. In some embodiments, such as wherein a safety issue (such as a non-consensual touch or a sexual assault by the therapist) has been detected, the stored 3D movement data can be used to for investigative purposes and/or ultimately to hold the therapist accountable (e.g., for disciplinary action by an employer, credentialing organization, or licensing board, or as evidence in a civil or criminal lawsuit, depending on the severity and law).

These embodiments are merely exemplary; the safety monitoring system and any components thereof (e.g., the safety monitoring device 1410, the safety alert) may perform a combination of functions described herein, as well as additional or alternative functions based on the specific needs of the patient, the location of the therapy, and other factors that will be appreciated by one of skill in the art. For example, in some embodiments, the patient has an additional means for directly triggering a safety alert. In some embodiments, the patient has a "safe word" that upon utterance directly triggers a safety alert. In some embodiments, the patient has a remote control device with a "panic button" that directly triggers a safety alert.

Having now described various embodiments of the invention, the following is provided to further clarify the scope of the disclosure. First, it should be noted that the steps or stages of a method, process, or algorithm described in connection with embodiments disclosed herein may be embodied directly in hardware, in a software module executed by a processor, or in a combination of both and/or other components. To clearly illustrate this interchangeability of hardware and software, various illustrative components, blocks, modules, means, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the spirit or scope of this disclosure.

Thus, the various illustrative components, blocks, modules, means, and steps described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. In some implementations, processors may be communication processors or other such processors specifically designed for implementing functionality in communication devices or other mobile or portable devices.

A software module may reside in RAM memory, flash memory, ROM memory, EPROM or EEPROM memory, registers, hard drive, a SSD, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC, which may reside in a user terminal. The processor and the storage medium also may reside as discrete components in a user terminal.

Some embodiments of the invention may include computer software and/or computer hardware/software combinations configured to implement one or more methods or functions associated with the invention such as those described herein. These embodiments may be in the form of modules implementing functionality in software and/or hardware software combinations.

Embodiments may also take the form of a computer storage product with a computer-readable medium having computer code thereon for performing various computer-implemented operations, such as operations related to functionality as described herein. The media and computer code may be those specially designed and constructed for the purposes of the invention, or they may be of the kind well known and available to those having skill in the computer software arts, or they may be a combination of both.

Examples of computer-readable media within the spirit and scope of the invention include solid-state drives (SSDs), magnetic media such as hard drives; optical media such as CD-ROMs, DVDs and holographic devices; magneto-optical media; and hardware devices that are specially configured to store and execute program code, such as programmable microcontrollers, ASICs, programmable logic devices (PLDs), and ROM and RAM devices.

Examples of computer code may include machine code, such as produced by a compiler or other machine code generation mechanisms, scripting programs, PostScript programs, and/or other code or files containing higher-level code that are executed by a computer using an interpreter or other code execution mechanism. Computer code may be comprised of one or more modules executing a particular process or processes to provide useful results, and the modules may communicate with one another via means known or developed in the art. For example, some disclosed embodiments may be implemented using assembly language, Java, C, C#, C++, scripting languages, and/or other programming languages and software development tools as are known or developed in the art. Other embodiments may be implemented in hardwired circuitry in place of, or in combination with, machine-executable software instructions.

While the methods described and illustrated herein may include particular steps or stages, it should be apparent that other processes including fewer, more, or different stages than those described and shown are also within the spirit and scope of the invention. The methods and associated components, blocks, modules, means, and steps shown herein should therefore be understood as being provided for purposes of illustration, not limitation. It should be further understood that the specific order or hierarchy of steps or stages in the methods disclosed are only exemplary approaches. Based upon design preferences, the specific order or hierarchy of steps in the methods may be rearranged while remaining within the spirit and scope of the present disclosure. The accompanying method claims present elements of the various steps in a sample order, and are not meant to be limited to the specific order or hierarchy presented.

The foregoing description, for purposes of explanation, uses specific nomenclature to provide a thorough understanding of the invention. However, it will be apparent to one skilled in the art that specific details are not required in order to practice the invention. Thus, the foregoing description of specific embodiments of the invention is presented for purposes of illustration and description. It is not intended to be exhaustive or to limit the invention to the precise forms disclosed; obviously, many modifications and variations are possible in view of the above teachings. The embodiments were chosen and described in order to best explain the principles of the invention and its practical applications, and to thereby enable others skilled in the art to best utilize the invention and various embodiments with various modifications as are suited to the particular use contemplated. Accordingly, the scope of the invention shall be defined solely by the following claims and their equivalents.

Enumerated Exemplary Embodiments

Embodiment 1. A method for communication using 3D human movement data, the method comprising the steps of: (a) capturing 3D human movement input from a sender; (b) creating a 3D movement data package from the 3D human movement input; (c) sending the 3D movement data package to a recipient device; and (d) rendering a 3D movement object on the recipient device, from the 3D movement data package.

Embodiment 2. The method of embodiment 1 further comprising the step of saving a 3D movement data file to permanent storage, comprising the 3D movement data package.

Embodiment 3. The method of embodiment 2 wherein the permanent storage contains a searchable movement database indexed based on the metadata of 3D movement files.

Embodiment 4. The method of embodiment 2 wherein the permanent storage contains a searchable movement database indexed based on movement data analysis of 3D movement files.

Embodiment 5. The method of embodiment 1 wherein the 3D movement data package created from the 3D human movement input reflects additional input from one or more additional input means.

Embodiment 6. The method of embodiment 5 wherein the additional input is voice input or input from the touchscreen of a smartphone or tablet device or the controls of a VR device.

Embodiment 7. The method of embodiment 5 wherein the additional input includes physiological, physiometric, or biometric data.

Embodiment 8. The method of embodiment 1 wherein the sender receives feedback from an output means.

Embodiment 9. The method of embodiment 8 wherein the feedback from an output means is visual feedback, auditory feedback, haptic feedback, or any combination thereof.

Embodiment 10. The method of embodiment 8 wherein the feedback from an output means is generated using higher-level features of the 3D human movement input.

Embodiment 11. The method of embodiment 10 wherein the higher-level features include smoothness of motion, range of motion, reaction time to a cue, gait size and speed, limb flexibility, and closeness of match to a predefined 3D movement.

Embodiment 12. The method of embodiment 1 wherein the 3D movement object on the recipient device is viewable to a recipient.

Embodiment 13. The method of embodiment 12 wherein the 3D movement object viewable to a recipient is interactive.

Embodiment 14. The method of embodiment 1 further comprising capturing 3D human movement input from at least one additional sender.

Embodiment 15. The method of embodiment 14 wherein the 3D movement object rendered on the recipient device is a combined 3D movement object, an amalgamated 3D movement object, or an average 3D movement object, said 3D movement object based on the captured 3D human movement input from the sender and the at least one additional sender.

Embodiment 16. The method of embodiment 1 further comprising rendering a 3D movement object on at least one additional recipient device.

Embodiment 17. The method of embodiment 1 further comprising the step of using the 3D movement data package to operate a mechanical apparatus.

Embodiment 18. A non-transitory computer-readable storage medium storing executable instructions that, when executed by a processor, cause the processor to perform steps comprising: (a) capturing 3D human movement input from a sender; (b) creating a 3D movement data package from the 3D human movement input; (c) sending the 3D movement data package to a recipient device; (d) receiving a 3D movement data message from a sending device; and (e) rendering a 3D movement object from the 3D movement data message.

Embodiment 19. The non-transitory computer-readable storage medium of embodiment 18 further comprising the step of saving a 3D movement data file to permanent storage, comprising the 3D movement data package.

Embodiment 20. The non-transitory computer-readable storage medium of embodiment 18 further comprising the step of using the 3D movement data message to operate a mechanical apparatus.

Embodiment 21. A system for communication using 3D human movement data, comprising a processor and a non-transitory computer-readable storage medium storing executable instructions that, when executed by the processor, cause the processor to perform steps comprising: (a) capturing 3D human movement input from a sender; (b) creating a 3D movement data package from the 3D human movement input; (c) sending the 3D movement data package to a recipient device; (d) receiving a 3D movement data message from a sending device; and (e) rendering a 3D movement object from the 3D movement data message.

Embodiment 22. The system of embodiment 21 further comprising the step of saving a 3D movement data file to permanent storage, comprising the 3D movement data package.

Embodiment 23. The system of embodiment 21 further comprising the step of using the 3D movement data message to operate a mechanical apparatus.

Embodiment 24. A method for communication using 3D non-facial human movement data, the method comprising the steps of: (a) capturing 3D non-facial human movement input from a sender; (b) creating a 3D non-facial movement data package from the 3D non-facial human movement input; (c) sending the 3D non-facial movement data package to a recipient device; and (d) rendering a 3D non-facial movement object on the recipient device, from the 3D non-facial movement data package.

Embodiment 25. The method of embodiment 24, further comprising the step of saving a 3D non-facial movement data file to permanent storage, comprising the 3D non-facial movement data package.

Embodiment 26. The method of embodiment 25, wherein the permanent storage contains a searchable movement database indexed based on the metadata of 3D non-facial movement data files.

Embodiment 27. The method of embodiment 25, wherein the permanent storage contains a searchable movement database indexed based on movement data analysis of 3D non-facial movement data files.

Embodiment 28. The method of embodiment 24, wherein the 3D non-facial movement data package created from the 3D non-facial human movement input reflects additional input from one or more additional input means.

Embodiment 29. The method of embodiment 28, wherein the additional input is voice input or input from the touchscreen of a smartphone or tablet device or the controls of a VR device.

Embodiment 30. The method of embodiment 28, wherein the additional input includes pulmonary, respiratory, or blood oxygenation data.

Embodiment 31. The method of embodiment 24, wherein the sender receives feedback from an output means.

Embodiment 32. The method of embodiment 31, wherein the feedback from an output means is visual feedback, auditory feedback, haptic feedback, or any combination thereof.

Embodiment 33. The method of embodiment 31, wherein the feedback from an output means is generated using higher-level features of the 3D non-facial human movement input and the higher-level features include smoothness of motion, range of motion, reaction time to a cue, gait size and speed, limb flexibility, kinetic energy, or closeness of match to a predefined 3D movement.

Embodiment 34. A method for communication using 3D human movement data, the method comprising the steps of: (a) capturing 3D human movement input from a sender; (b) creating a 3D movement data package from the 3D human movement input; (c) sending the 3D movement data package to a recipient device; and (d) rendering a 3D movement object on the recipient device, from the 3D movement data package; wherein the sender receives feedback from an output means, wherein the feedback from the output means is generated using high-level features of the 3D human movement input, and wherein the higher-level features include any of smoothness of motion, range of motion, reaction time to a cue, gait size and speed, limb flexibility, kinetic energy, and closeness of match to a predefined 3D movement.

Embodiment 35. The method of embodiment 24 wherein the 3D non-facial movement object on the recipient device is viewable to a recipient.

Embodiment 36. The method of embodiment 35 wherein the 3D non-facial movement object viewable to a recipient is interactive.

Embodiment 37. The method of embodiment 24 further comprising capturing 3D non-facial human movement input from at least one additional sender.

Embodiment 38. The method of embodiment 37 wherein the 3D non-facial movement object rendered on the recipient device is a combined 3D movement object, an amalgamated 3D movement object, or an average 3D movement object, said 3D non-facial movement object based on the captured 3D non-facial human movement input from the sender and the at least one additional sender.

Embodiment 39. The method of embodiment 24 further comprising rendering a 3D non-facial movement object on at least one additional recipient device.

Embodiment 40. The method of embodiment 24 further comprising the step of using the 3D non-facial movement data package to operate a mechanical apparatus.

Embodiment 41. A non-transitory computer-readable storage medium storing executable instructions that, when executed by a processor, cause the processor to perform steps comprising: (a) capturing 3D non-facial human movement input from a sender; (b) creating a 3D non-facial movement data package from the 3D non-facial human movement input; (c) sending the 3D non-facial movement data package to a recipient device; (d) receiving a 3D non-facial movement data message from a sending device; and (e) rendering a 3D non-facial movement object from the 3D non-facial movement data message.

Embodiment 42. The non-transitory computer-readable storage medium of embodiment 41 further comprising the step of saving a 3D non-facial movement data file to permanent storage, comprising the 3D non-facial movement data package.

Embodiment 43. The non-transitory computer-readable storage medium of embodiment 41 further comprising the step of using the 3D non-facial movement data message to operate a mechanical apparatus.

Embodiment 44. A system for communication using 3D non-facial human movement data, comprising a processor and a non-transitory computer-readable storage medium storing executable instructions that, when executed by the processor, cause the processor to perform steps comprising: (a) capturing 3D non-facial human movement input from a sender; (b) creating a 3D non-facial movement data package from the 3D non-facial human movement input; (c) sending the 3D non-facial movement data package to a recipient device; (d) receiving a 3D non-facial movement data message from a sending device; and (e) rendering a 3D non-facial movement object from the 3D non-facial movement data message.

Embodiment 45. The system of embodiment 44 further comprising the step of saving a 3D non-facial movement data file to permanent storage, comprising the 3D non-facial movement data package.

Embodiment 46. The system of embodiment 44 further comprising the step of using the 3D non-facial movement data message to operate a mechanical apparatus.

Embodiment 47. A method for psychedelic-assisted therapy (PAT) using 3D human movement data, the method comprising the steps of: (a) capturing a first 3D human movement input from a patient during a preparation session for PAT; (b) creating a first 3D movement data package from the first 3D human movement input; (c) saving a first 3D movement data file to permanent storage, comprising the first 3D movement data package; (d) capturing a second 3D human movement input from a patient during a psychedelic dosing session; (e) creating a second 3D movement data package from the second 3D human movement input; (f) saving a second 3D movement data file to permanent storage, comprising the second 3D movement data package; and (g) comparing the first 3D movement data file and the second 3D movement data file during an integration session.

Embodiment 48. The method of embodiment 47 wherein the permanent storage contains a searchable movement database indexed based on the metadata of 3D movement files.

Embodiment 49. The method of embodiment 48 wherein the searchable movement database contains metadata based on protocols developed for the standardization of procedures used with PAT.

Embodiment 50. A method for PAT using 3D human movement data, the method comprising the steps of: (a) capturing a first 3D human movement input from a therapist during a preparation session for PAT; (b) creating a first 3D movement data package from the first 3D human movement input; (c) saving a first 3D movement data file to permanent storage, comprising the first 3D movement data package; (d) capturing a second 3D human movement input from a patient during a psychedelic dosing session; (e) creating a second 3D movement data package from the second 3D human movement input; (f) sending the second 3D movement data package to a first recipient device; (g) rendering a 3D movement object on the first recipient device, from the second 3D movement data package; (h) sending the first 3D movement data package to a second recipient device; and (i) rendering a 3D movement object on the second recipient device, from the first 3D movement data package.

Embodiment 51. The method of embodiment 50 further comprising the step of saving a second 3D movement data file to permanent storage, comprising the second 3D movement data package.

Embodiment 52. The method of embodiment 51, wherein the permanent storage contains a searchable movement database indexed based on the metadata of 3D movement files.

Embodiment 53. The method of embodiment 50, wherein the second 3D movement data package created from the second 3D human movement input contains additional input from one or more additional input means.

Embodiment 54. A method for communication using 3D human movement data, the method comprising the steps of: (a) capturing 3D human movement input from a sender; (b) creating a 3D movement data package from the 3D human movement input, wherein the 3D movement data package includes 3D coordinate data; (c) sending the 3D movement data package to a recipient device; and (d) rendering a 3D movement object on the recipient device using 3D coordinate data, from the 3D movement data package.

Embodiment 55. The method of embodiment 1, wherein the 3D movement data package includes 3D coordinate data and is saved to permanent storage.

Embodiment 56. The method of embodiment 1, wherein the 3D movement data package includes 3D coordinate data and is saved for asynchronous use.

Embodiment 57. The method of embodiment 1, wherein the 3D movement data package is comprised only of 3D coordinate data.

Embodiment 58. The method of embodiment 1, wherein 3D coordinate data is used to render a 3D movement object, in 3D space in any of augmented-reality, mixed-reality, and virtual-reality environments, on the recipient device.

Embodiment 59. The method of embodiment 58, wherein the 3D coordinate data is saved to permanent storage.

Embodiment 60. A method for providing biomarker-augmented mental health therapy to a user, comprising: (a) obtaining a set of collected data from the user; (b) creating a set of processed data from the collected data; (c) using the processed data to determine a set of personalized biomarkers and protocol for mental health therapy; and (d) utilizing the personalized biomarkers and protocol in mental health therapy for the user.

Embodiment 61. A method for providing biomarker-augmented mental health therapy to user, comprising: (a) obtaining a set of collected data from the user; (b) creating a set of processed data from the collected data; (c) obtaining a set of reference data from a reference population; (d) using the processed data together with the reference data to determine a set of personalized biomarkers and protocol for mental health therapy; and (e) utilizing the personalized biomarkers and protocol in mental health therapy for the user.

Embodiment 62. The method of embodiment 60 or 61, wherein the mental health therapy comprises PAT.

Embodiment 63. The method of embodiment 60 or 61, wherein the mental health therapy comprises body-image therapy.

Embodiment 64. The method of any one of embodiments 60-63, wherein the personalized biomarkers and protocol are used for mental health diagnosis.

Embodiment 65. The method of any one of embodiments 60-64, wherein the collected data comprises any of body pose or posture data, body sway or sway data, body balance or balance data, body rhythm or rhythm data, body asymmetries or asymmetry data, smoothness of motion data of the body or body parts, jerkiness of motion data of the body or body parts, motion data of a user as a user moves towards or away from a cue, kinetic energy data of the body or body parts, flexibility data of the body or body parts, reaction time of the body or body parts, or total amount of body movement.

Embodiment 66. The method of embodiment 65, wherein the collected data further comprises any of a user's mental health history, heart rate, heart rate variability (HRV), electroencephalography measurement (EEG), pulmonary function, respiratory rate, brain entropy, genetic biomarkers, voice characteristics, or eye movement.

Embodiment 67. The method of any one of embodiments 60-66, wherein the collected data is obtained using an electronic means, such as a mobile electronic device, personal electronic device, or interactive electronic device.

Embodiment 68. The method of any one of embodiments 60-64, wherein the personalized biomarkers and protocol are used in clinical research on mental health.

Embodiment 69. The method of embodiment 68, wherein one or more sets of personalized biomarkers and protocol are used with an artificial neural network or machine learning program.

Embodiment 70. The method of embodiment 63, wherein the body-image therapy is used to treat any of anorexia nervosa, body image dysmorphia, or an eating disorder.

Embodiment 71. The method of any one of embodiments 60-70, wherein the biomarker-augmented mental health therapy is conducted through a virtual reality or augmented reality electronic means.

Embodiment 72. The method of embodiment 71, wherein the biomarker-augmented mental health therapy includes the user doing actions in an avatar that is dissimilar to the user's body.

Embodiment 73. The method of any one of embodiments 60-72, wherein the biomarker-augmented mental health therapy results in an improvement to the user of a mental disease or disorder, an improvement to the user of a health condition, or an improvement to the user of overall health and well-being.

Embodiment 74. A system for providing biomarker-augmented mental health therapy to a user, comprising a processor and a non-transitory computer-readable storage medium storing executable instructions that, when executed by the processor, cause the processor to perform steps comprising: (a) obtaining a set of collected data from the user; (b) creating a set of processed data from the collected data; (c) using the processed data to determine a set of personalized biomarkers and protocol for mental health therapy; and (d) utilizing the personalized biomarkers and protocol in mental health therapy for the user.

Embodiment 75. A system for providing biomarker-augmented mental health therapy to a user, comprising a processor and a non-transitory computer-readable storage medium storing executable instructions that, when executed by the processor, cause the processor to perform steps comprising: (a) obtaining a set of collected data from the user; (b) creating a set of processed data from the collected data; (c) obtaining a set of reference data from a reference population; (d) using the processed data together with the reference data to determine a set of personalized biomarkers and protocol for mental health therapy; and (e) utilizing the personalized biomarkers and protocol in mental health therapy for the user.

Embodiment 76. The system of embodiment 74 or 75, further comprising: (a) putting the personalized biomarkers and protocol into an artificial neural network or machine learning program; and (b) utilizing the artificial neural network or machine learning program to create improvements to mental health therapy or clinical research on mental health.

Embodiment 77. A method for improving patient safety during mental health therapy, comprising: (a) capturing a first 3D human movement input from a therapist; (b) creating a first 3D movement data package from the first 3D human movement input; (c) capturing a second 3D human movement input from a patient; (d) creating a second 3D movement data package from the second 3D human movement input; (e) detecting a safety issue with a detection algorithm; and (f) triggering a safety alert.

Embodiment 78. The method of embodiment 77, wherein the detection algorithm comprises analyzing the first 3D movement data package and the second 3D movement data package.

Embodiment 79. The method of embodiment 77 or 78, wherein the detection algorithm comprises receiving an auditory input from a patient.

Embodiment 80. The method of any one of embodiments 77-79, wherein the detection algorithm comprises receiving an electronic signal input from a patient.

Embodiment 81. The method of any one of embodiments 77-80, wherein the safety issue is inappropriate touch.

Embodiment 82. The method of any one of embodiments 77-81, wherein the safety issue is sexual assault.

Embodiment 83. The method of any one of embodiments 77-82, wherein the safety alert comprises an alarm.

Embodiment 84. The method of any one of embodiments 77-83, wherein the safety alert comprises recording a photograph, a video, or an audio recording.

Embodiment 85. The method of any one of embodiments 77-84, wherein the safety alert comprises transmitting an emergency message.

Embodiment 86. The method of any one of embodiments 77-85, further comprising storing the first 3D human movement input, first 3D human movement data package, second 3D human movement input, or second 3D human movement input in permanent storage.

Embodiment 87. The method of embodiment 86, wherein the permanent storage is on a remote storage device.

Embodiment 89. The method of any one of embodiments 77-87, wherein the mental health therapy is PAT.

Embodiment 90. The method of embodiment 3, further comprising determining characteristic movement markers associated with a positive or negative patient experience in the first or second 3D movement data file.

Embodiment 91. A method for PAT using 3D human movement data, the method comprising the steps of: (a) capturing a first 3D human movement input from a patient during a session of PAT; (b) creating a first 3D movement data package from the first 3D human movement input; and (c) determining characteristic movement markers associated with a positive or negative patient experience.

Embodiment 92. The method of embodiment 91, wherein the characteristic movement markers are associated with a positive patient experience.

Embodiment 93. The method of embodiment 91 or 92, further comprising utilizing the characteristic movement markers to predict or promote a positive patient experience Embodiment 94. The method of embodiment 91, wherein the characteristic movement markers are associated with a negative patient experience.

Embodiment 95. The method of embodiment 91 or 94, further comprising utilizing the characteristic movement markers to predict or prevent a negative patient experience.

Embodiment 96. The method of any one of embodiments 91-95, wherein the first 3D human movement input is captured during a preparation session for PAT.

Embodiment 97. The method of any one of embodiments 91-95, wherein the first 3D human movement input is captured during a psychedelic dosing session.

Embodiment 98. The method of any one of embodiments 91-97, further comprising capturing a second 3D human movement input from a patient, and creating a second 3D movement data package from the second 3D human movement input.

Embodiment 99. The method of embodiment 98, wherein the second 3D human movement input is captured during a psychedelic dosing session.

Embodiment 100. The method of embodiment 98, wherein the second 3D human movement input is captured after a psychedelic dosing session.

Embodiment 101. The method of any one of embodiments 91-100, further comprising evaluating the efficacy of the therapy by comparing the first 3D movement data package and the second 3D movement data package.

Embodiment 102. The method of embodiment 101, wherein evaluating the efficacy comprises comparing the characteristic movement markers in the first 3D movement data package and the characteristic movement markers in the second 3D movement data package.

The invention claimed is:

1. A method for psychedelic-assisted therapy using 3D human movement data, the method comprising the steps of:
   a. capturing a first 3D human movement input from a patient during a preparation session for psychedelic-assisted therapy;
   b. creating a first 3D movement data package from the first 3D human movement input;
   c. saving a first 3D movement data file to permanent storage, comprising the first 3D movement data package;
   d. capturing a second 3D human movement input from a patient during a psychedelic dosing session;
   e. creating a second 3D movement data package from the second 3D human movement input;
   f. saving a second 3D movement data file to permanent storage, comprising the second 3D movement data package; and
   g. comparing the first 3D movement data file and the second 3D movement data file during an integration session.

2. The method of claim 1, wherein the permanent storage contains a searchable movement database indexed based on the metadata of 3D movement files.

3. The method of claim 2, wherein the searchable movement database contains metadata based on protocols developed for the standardization of procedures used with psychedelic-assisted therapy.

4. The method of claim 1, further comprising determining characteristic movement markers associated with a positive or negative patient experience in the first or second 3D movement data file.

5. The method of claim 4, wherein the characteristic movement markers are associated with a positive patient experience.

6. The method of claim 5, further comprising utilizing the characteristic movement markers to predict or promote a positive patient experience.

7. The method of claim 4, wherein the characteristic movement markers are associated with a negative patient experience.

8. The method of claim 7, further comprising utilizing the characteristic movement markers to predict or prevent a negative patient experience.

9. The method of claim 1, wherein comparing the first 3D movement data file and the second 3D movement data file is used to predict or promote a positive patient experience, to predict or prevent a negative patient experience, or to evaluate the efficacy of the therapy.

10. A method for psychedelic-assisted therapy using 3D human movement data, the method comprising the steps of:
    a. capturing a first 3D human movement input from a therapist during a preparation session for psychedelic-assisted therapy;
    b. creating a first 3D movement data package from the first 3D human movement input;
    c. saving a first 3D movement data file to permanent storage, comprising the first 3D movement data package;
    d. capturing a second 3D human movement input from a patient during a psychedelic dosing session;
    e. creating a second 3D movement data package from the second 3D human movement input;
    f. sending the second 3D movement data package to a first recipient device;
    g. rendering a 3D movement object on the first recipient device, from the second 3D movement data package;
    h. sending the first 3D movement data package to a second recipient device; and
    i. rendering a 3D movement object on the second recipient device, from the first 3D movement data package.

11. The method of claim 10, further comprising the step of saving a second 3D movement data file to permanent storage, comprising the second 3D movement data package.

12. The method of claim 11, wherein the permanent storage contains a searchable movement database indexed based on the metadata of 3D movement files.

13. The method of claim 10, wherein the second 3D movement data package created from the second 3D human movement input contains additional input from one or more additional input means.

14. The method of claim 10, further comprising determining characteristic movement markers associated with a positive or negative patient experience from the second 3D human movement input or the second 3D movement data package.

15. The method of claim 14, wherein the characteristic movement markers are associated with a positive patient experience.

16. The method of claim 15, further comprising utilizing the characteristic movement markers to predict or promote a positive patient experience.

17. The method of claim 14, wherein the characteristic movement markers are associated with a negative patient experience.

18. The method of claim 17, further comprising utilizing the characteristic movement markers to predict or prevent a negative patient experience.

19. The method of claim 10, further comprising evaluating the efficacy of the therapy by comparing the first 3D movement data package and the second 3D movement data package.

20. The method of claim 19, wherein evaluating the efficacy comprises comparing characteristic movement markers of the therapist in the first 3D movement data package and characteristic movement markers of the patient in the second 3D movement data package.

* * * * *